US009901636B2

(12) United States Patent
Berg et al.

(10) Patent No.: US 9,901,636 B2
(45) Date of Patent: Feb. 27, 2018

(54) CONJUGATE OF A PHOTOSENSITISER AND CHITOSAN AND USES THEREOF

(71) Applicant: PCI BIOTECH AS, Lysaker (NO)

(72) Inventors: Kristian Berg, Heggedal (NO); Anders Hogset, Oslo (NO); Mar Masson, Reykjavik (IS); Vivek S. Gaware, Reykjavik (IS)

(73) Assignee: PCI BIOTECH AS, Oslo (NO)

( * ) Notice: Subject to any disclaimer, the term of this patent is extended or adjusted under 35 U.S.C. 154(b) by 0 days.

(21) Appl. No.: 14/401,215

(22) PCT Filed: May 14, 2013

(86) PCT No.: PCT/EP2013/059968
§ 371 (c)(1),
(2) Date: Nov. 14, 2014

(87) PCT Pub. No.: WO2013/189663
PCT Pub. Date: Dec. 27, 2013

(65) Prior Publication Data
US 2015/0202293 A1 Jul. 23, 2015

(30) Foreign Application Priority Data

May 15, 2012 (GB) .................... 1208548.6

(51) Int. Cl.
*A61K 41/00* (2006.01)
*A61K 47/48* (2006.01)
*C08B 37/08* (2006.01)

(52) U.S. Cl.
CPC ...... *A61K 41/0057* (2013.01); *A61K 41/0076* (2013.01); *A61K 47/4823* (2013.01); *C08B 37/003* (2013.01)

(58) Field of Classification Search
CPC .......................... A61K 41/0057; C08B 37/003
USPC ....................................................... 544/145
See application file for complete search history.

(56) References Cited

U.S. PATENT DOCUMENTS

| 2002/0022032 A1 | 2/2002 | Curry et al. |
| 2009/0209508 A1 | 8/2009 | Lange et al. |
| 2010/0129432 A1 | 5/2010 | Chen et al. |
| 2010/0222538 A1 | 9/2010 | Kwon et al. |
| 2012/0035180 A1 | 2/2012 | Park et al. |
| 2012/0087859 A1 | 4/2012 | Tae et al. |

FOREIGN PATENT DOCUMENTS

| CN | 101024087 | 8/2007 |
| JP | 2008-506675 | 3/2008 |
| KR | 1020090047872 | 5/2009 |
| KR | 10-0918811 | 9/2009 |
| KR | 10-2010-0051163 | 5/2010 |
| KR | 20120045155 | 5/2012 |
| WO | 96/07432 | 3/1996 |
| WO | 00/54802 | 9/2000 |
| WO | 03/020309 | 3/2003 |
| WO | 2006/005924 | 1/2006 |
| WO | 2008/130181 | 10/2008 |
| WO | 2009/077908 | 6/2009 |
| WO | 2010/143942 | 12/2010 |
| WO | 2011/018635 | 2/2011 |

OTHER PUBLICATIONS

McMahon et al. (2000).*
Pinedo et al. (2000).*
Gaware, V.S. et al., Tetraphenylporphyrin Tethered Chitosan Based Carriers for Photochemical Transfection, Journal of Medicinal Chemistry, 2013, vol. 56, No. 3, pp. 807-819.
Jorgensen, J.A.L. et al., Potent Gene Silencing in vitro at Physiological pH Using Chitosan Polymers, Nucleic Acid Therapeutics, 2012, vol. 22, No. 2, pp. 96-102.
Lee, S.J. et al., Comparative Study of Photosensitizer Loaded and Conjugated Glycol Chitosan Nanoparticles for Cancer Therapy, Journal of Controlled Release, 2011, vol. 152, No. 1, pp. 21-29.
Huang, C.H. et al., Preparation and Characterization of Ternary Composite Composed by Chitosan, Porphyrin Derivative and Single-Walled Carbon Nanotubes, Advanced Materials Research, 2012, vols. 535-537, pp. 1591-1596.
International Search Report and Written Opinion for PCT/EP2013/059968, dated Jul. 25, 2013.
Rúnarsson et al., "Antibacterial Activity of N-quaternary Chitosan Derivatives: Synthesis, Characterization and Structure Activity Relationship (SAR) Investigations", European Polymer Journal, vol. 46, 2010, pp. 1251-1267.
Song et al., "Functionalized Superhydrophobic Biomimetic Chitosan-based Films", Carbohydrate Polymers, vol. 81, 2010, pp. 140-144.
Zaharoff et al., "Chitosan Solution Enhances both Humoral and Cell-Mediated Immune Responses to Subcutaneous Vaccinations", Vaccine, vol. 25(11), 2007, pp. 2085-2094.
Zaharoff et al., "Intravesical Immunotherapy of Superficial Bladder Cancer with Chitosan/Interleukin-12", Cancer Res., vol. 69(15), 2009, pp. 6192-6199.
Benediktsdóttir et al., "Synthesis of N,N,N-trimethyl Chitosan Homopolymer and Highly Substituted N-alkyl-N,N-dimethyl Chitosan Derivatives with the Aid of di-tert-butyldimethylsilyl Chitosan", Carbohydrate Polymers, vol. 86, 2011, pp. 1451-1460.
Berg et al., "Disulfonated Tetraphenyl Chlorin (TPCS$_{2a}$), a Novel Photosensitizer Developed for Clinical Utilization of Photochemical Internalization", Photochem. Photobio. Sci., vol. 10, 2011, pp. 1637-1651.

(Continued)

*Primary Examiner* — Paul V Ward
(74) *Attorney, Agent, or Firm* — Wenderoth, Lind & Ponack, L.L.P.

(57) ABSTRACT

The present invention relates to novel chitosan-based conjugates, e.g. nanocarriers, comprising a derivative of the biocompatible polymer chitosan conjugated to a photosensitizing agent, and uses thereof in photochemical internalization (PCI) and photodynamic therapy (PDT). The invention also relates to the use of the novel conjugates of the invention in treatment or prevention of diseases, particularly cancer, and for vaccination purposes.

28 Claims, 28 Drawing Sheets

(56) References Cited

OTHER PUBLICATIONS

Berg et al., "Lysosomes and Microtubules as Targets for Photochemotherapy of Cancer", Photochemistry and Photobiology, vol. 65(3), 1997, pp. 403-409.
Lee et al., "Tumor-homing Photosensitizer-conjugated Glycol Chitosan Nanoparticles for Synchronous Photodynamic Imaging and Therapy Based on Cellular On/Off System", Biomaterials, vol. 32, 2011, pp. 4021-4029.
Park et al., "Targeted Delivery of Low Molecular Drugs Using Chitosan and its Derivatives", Advanced Drug Delivery Reviews, vol. 62, 2010, pp. 28-41.
Rúnarsson et al., "tert-Butyldimethylsilyl O-protected Chitosan and Chitooligosaccharides: Useful Precursors for N-modifications in Common Organic Solvents", Carbohydrate Research, vol. 343, 2008, pp. 2576-2582.
Lee et al., "Comparative Study of Photosensitizer Loaded and Conjugated Glycol Chitosan Nanoparticles for Cancer Therapy", vol. 152, 2011, pp. 21-29.
Bonnett et al., "Water disinfection using photosensitizers immobilized on chitosan", Water Research, 40: 1269-1275 (2006).
Moczek et al., "Novel Water-Soluble Photosensitizers from Chitosan", Biomacromolecules, 8: 433-438 (2007).
Nowakowska et al., "Photoactive Modified Chitosan", Biomacromolecules, 9: 1631-1636 (2008).
Park et al., "A Smart Polysaccharide/Drug Conjugate for Photodynamic Therapy", Angew. Chem. In. Ed., 50: 1644-1647 (2011).
Victorsson, E.O., "Chitosan nanocarriers for light activated cancer therapy—Synthesis and characterization", Graduate Thesis, University of Iceland, School of Health Sciences, Jun. 2012.
Japanese Office Action, dated Jun. 20, 2017 in corresponding Japanese Patent Application No. 2015-512042, with English language translation.

* cited by examiner

Compound 16A, 16B - 10%, 90%
Compound 17A, 17B - 25%, 75%

Compound 18A, 18B - 10%, 90%
Compound 19A, 19B - 25%, 75%

Compound 37

Compound 38

Compound 32

10%  90%  Compound 33

R$_1$-10%,  R$_2$-90%  Compound 54

R$_3$- 4%, R$_4$-23%  Compound 57

Scheme 1

Scheme 2

Scheme 3

21
TPC-NH-Pip compound 20 is a mixture of inseparable isomers.
One possible isomer is shown Scheme 4

A

B

Compound 26 is a mixture of inseparable isomers. Here and onwards only one of the possible isomers is shown.

28
TPC-CO-pip

Scheme 5

Scheme 6A compound 32 & 33 are derivatives of the TPCa1 and TPCa2 isomers. Only structure of theTPCa1 isomer is shown in the stucture drawing Scheme 6B compound 37 & 38 are derivatives of the TPCc1 and TPCc2 isomers. Only structure of theTPCc1 isomer is shown in the stucture drawing ■ GFP+ cells. ○ Cell survival.

■ GFP+ cells. ○ Cell survival.

■ GFP positive cells.  ○ Cell survival

Scheme 7

Scheme 8

Scheme 9

A

B where,

X - Br

CONJUGATE OF A PHOTOSENSITISER AND CHITOSAN AND USES THEREOF

The present invention relates to novel chitosan-based conjugates, e.g. nanocarriers, comprising a derivative of the biocompatible polymer chitosan conjugated to a photosensitising agent, and uses thereof in photochemical internalisation (PCI) and photodynamic therapy (PDT). The invention also relates to the use of the novel conjugates of the invention in treatment or prevention of diseases, particularly cancer, and for vaccination purposes.

Nanomaterials have special physiochemical properties that include small size and large surface area to mass ratio and high activity compared to bulk materials of the same composition. These unique properties can improve and overcome some of the limitations found in traditional medicine. The application of nanomaterials provides an opportunity to modify properties such as solubility, diffusivity, blood circulation half-life, drug release characteristics and immunogenicity. In the last two decades, a number of nanoparticle-based agents for therapeutic and diagnostic applications have been developed for treatment of diseases.

The use of nanomaterials may provide more effective and more convenient routes of administration, lower toxicity, minimized side effects, increased bioavailability and extended life-cycle of the product in the system. As drug-delivery systems, nanoparticles or nanocarriers can provide targeted delivery and controlled release. Furthermore, they can be used for diagnostic purposes. They may, for example, allow the detection of pre-cancerous cells, virus fragments and disease markers that cannot be detected by established traditional approaches.

Currently, natural- and synthetic polymers along with liposomes are the main nanoparticle platforms encountered in the literature (Peer et al., 2007, Natl., 2(12), p 751-760). Other popular platforms include dendrimers, oil nanoemulsions, mesoporous silica nanoparticles and iron oxide nanoparticles.

The novel conjugates of the present invention, which may be nanocarriers, comprise derivatives of the biocompatible polymer chitosan, which is derived from chitin. Chitin (poly(β-(1→4)-N-acetyl-D-glucosamine)) is a naturally occurring polysaccharide and the supporting material of insects and crustaceans. Chitin is the second most natural abundant polysaccharide on earth after cellulose. It is generally derived from sources such as crab and shrimp cells. Structurally, chitin is similar to cellulose but has an acetamide group instead of a hydroxyl group on the C2 position of the polymer backbone.

Chitosan is the most important derivative of chitin, normally produced by removing the acetyl groups by alkaline methods. Whilst most naturally occurring polymers are neutral or acidic in nature, chitosan is a highly basic polysaccharide. The nitrogen atom in the C2 position provides an opportunity to modify the polymer by synthetic strategies to tailor the molecule towards certain desirable properties, for example increased solubility and improved biological properties.

The chitosan polymer consists of β-(1→4) linked D-glucosamine units with various degrees of deacetylation (DD), wherein the remaining acetyl groups are distributed in blocks or randomly throughout the linear polymer chain. Chitosan is soluble in diluted acids such as acetic acid due to the positive charge of the amino group at acidic conditions. Although the DD can be very variable it is almost never 100%. Distinctive nomenclature of chitin versus chitosan regarding DD has not been defined but the DD for chitosan can vary from 40-100%. Molecular weights can be up to 2000 kDa but those below 50 kDa are sometimes considered as oligochitosans.

Attention has been paid to chitin and chitosan in the last decades in regard to their application potential in medicine. Various chitosan derivatives have been designed and synthesized in order to enhance solubility and to further improve its physical, chemical, and biological properties.

In addition to the chitosan derivative, the conjugates of the present invention also comprise a photosensitising agent, which is conjugated to the chitosan. The conjugates thus have particular use in methods involving photosensitisation.

Photosensitisation is a process of transferring the energy of absorbed light. After absorption, the energy is transferred to the (chosen) reactants. Photosensitisers are compounds that are capable of translating the energy of light into type II chemical reactions. The highly reactive end products of these processes result in cyto- and vascular toxicity.

Photosensitisers may exert their effects by a variety of mechanisms, directly or indirectly. Thus for example, certain photosensitisers become directly toxic when activated by light, whereas others act to generate toxic species, e.g. oxidising agents such as singlet oxygen or other oxygen-derived free radicals, which are extremely destructive to cellular material and biomolecules such as lipids, proteins and nucleic acids.

There are many known photosensitising agents, including porphyrins, phthalocyanines, purpurins, chlorins, benzoporphyrins, lysomotropic weak bases, naphthalocyanines, cationic dyes and tetracyclines or derivatives thereof (Berg et al., (1997), J. Photochemistry and Photobiology, 65, 403-409). Other photosensitising agents include texaphyrins, pheophorbides, porphycenes, bacteriochlorins, ketochlorins, hematoporphyrin derivatives, and endogenous photosensitizers induced by 5-aminolevulinic acid. As discussed below, in the chitosan-based molecules of the present invention, porphyrins and chlorins, particularly tetraphenylporphyrin (TPP) and tetraphenylchlorin (TPC), are employed.

Porphyrins are the most extensively studied photosensitising agents. Their molecular structure includes four pyrrole rings linked together via methine bridges. They are natural compounds which are often capable of forming metal-complexes. For example in the case of the oxygen transport protein hemoglobin, an iron atom is introduced into the porphyrin core of heme B.

Chlorins are large heterocyclic aromatic rings consisting, at the core, of three pyrroles and one pyrroline coupled through four methine linkages. Unlike porphyrin, a chlorin is therefore largely aromatic, but not aromatic through the entire circumference of the ring.

Photosensitising agents are used in photodynamic therapy (PDT) and photochemical internalisation (PCI) methods. PDT is a two-step process involving the administration of a photosensitizer systematically or topically, followed by light illumination of an appropriate wavelength. For cytotoxic effects to take place, molecular oxygen must also be present. When these three factors are combined successfully (i.e. photosensitizer, light and oxygen), a photodynamic reaction occurs. The photodynamic reaction leads to generation of cytotoxic species, which cause cell death and tissue damage.

PDT is used for the treatment of, for example, cancer. Radical intermediates from photodynamic reactions are scavenged by oxygen in biological tissues to yield reactive oxygen species (ROS) such as singlet oxygen ($^1O_2$). $^1O_2$ is a short lived form of oxygen with highly cytotoxic potential.

Therefore, the highly selective cytotoxic treatment where systemic side effects are avoided to a large extent can be achieved.

PCI is based on the same principle as PDT, but produces fewer ROS (e.g. by using lower light doses) to induce release of trapped drugs and macromolecules from endosomes into the cytosol without significant cell death due to ROS. In PCI the light excitation leads to ROS mediated damage selectively of the lysosomal and/or endosomal membranes and the release of entrapped hydrophilic drugs and macromolecules. Thereby endocytosed molecules can be released to reach their target of action before being degraded in lysosomes.

PCI has been shown to enhance biological activity of a large variety of macromolecules and other molecules that do not readily penetrate through plasma membrane including type-I ribosome-inactivating proteins, immunotoxins, chemotherapeutic agents such as Bleomycin (Blenoxane®) and Doxorubicin, gene encoding plasmids and oligonucleotides. It has been found to induce cytotoxicity in deeper tissue layers than the corresponding PDT. Due to the combination of targeted therapeutics with light-activated cytosolic delivery induced by photosensitisers preferentially accumulating in solid tumors, PCI can be highly specific and this also contributes to enhanced antitumor efficacy.

One of the common problems associated with PDT in clinical application is skin photosensitivity and unfavorable biodistribution of photosensitizer. Nanocarriers such as dendrimers, liposomes and polymeric micelles have been introduced as an approach to reduce side effects and to improve pharmacokinetics in PDT.

There remains a need for improved nanocarriers and photosensitizing agents for use in PCI and PDT methods. The present invention addresses this need. The present inventors have developed novel compounds, which are based on a conjugate of a photosensitiser and chitosan. The novel molecules have surprisingly high efficacy in PCI methods, as illustrated in the Examples below which demonstrate surprisingly good efficacy both in vitro and in vivo.

Thus, in a first aspect the present invention provides a compound e.g. a nanocarrier, comprising a conjugate of a photosensitiser and chitosan, wherein said compound is a compound of Formula (I):

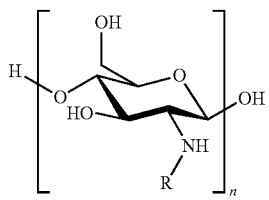

wherein
n is an integer greater than or equal to 3,
R appears n times in said compound and
in 0.1%-99.9% of said total Rn groups, each R is a group A selected from:
H,

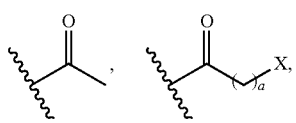

wherein a is 1, 2, 3, 4 or 5; and X is Br, Cl or OH;

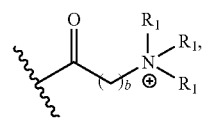

wherein each $R_1$, which may be the same or different, is selected from H, $CH_3$ and —$(CH_2)_c$—$CH_3$; b is 1, 2, 3, 4 or 5; and c is 0, 1, 2, 3, 4 or 5 (in which the counter-ion may be, for example, $Cl^-$);

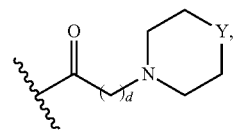

wherein Y is O; S; $SO_2$, —$NCH_3$, or —$N(CH_2)_eCH_3$, d=1, 2, 3, 4 or 5; and e=1, 2, 3, 4 or 5;

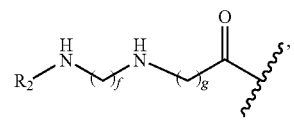

wherein $R_2$ is —$(CH_2)_h$—$CH_3$ or —CO—$(CH_2)_h$—$CH_3$; f is 1, 2, 3, 4 or 5; g is 1, 2, 3, 4 or 5; and h is 0, 1, 2, 3, 4 or 5;

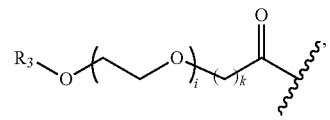

wherein $R_3$ is —$(CH_2)_j$—$CH_3$, i is an integer from 1 to 200, preferably from 1-50 or 1-10, e.g. 1, 2, 3, 4, 5, 6, 7, 8, 9 or 10, or at least 10, 20, 30, 40, 50, 60, 70, 80, 90, 100 or 200; j is 0, 1, 2, 3, 4 or 5; and k is 1, 2, 3, 4 or 5;

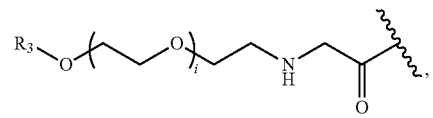

wherein $R_3$ is —$(CH_2)_j$—$CH_3$, i is an integer as defined above; and j is 0, 1, 2, 3, 4 or 5;

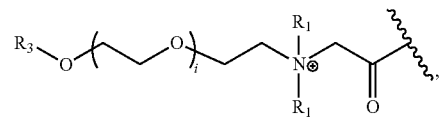

wherein $R_3$ is —$(CH_2)_j$—$CH_3$, i is an integer as defined above; j is 0, 1, 2, 3, 4 or 5; and each $R_1$, which may be the same or different, is selected from H, CH₃ and —(CH₂)$_c$—CH₃; and c is 0, 1, 2, 3, 4 or 5;

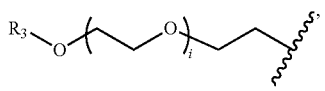

wherein $R_3$=—(CH₂)$_j$—CH₃, i is an integer as defined above; and j is 0, 1, 2, 3, 4 or 5;

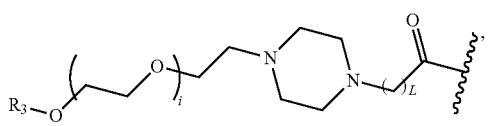

wherein $R_3$=—(CH₂)$_j$—CH₃, i is an integer as defined above; L is 1, 2, 3, 4, 5, 6, 7, 8, 9 or 10; and j is 0, 1, 2, 3, 4 or 5;

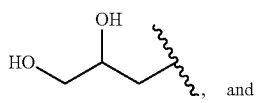, and

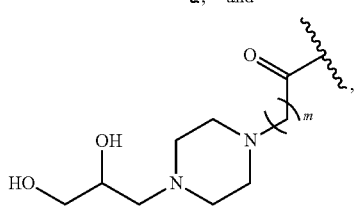

wherein m is 1, 2, 3, 4 or 5;

wherein each R group may be the same or different; and in 0.1%-99.9% of said total Rn groups, each R is a group B selected from:

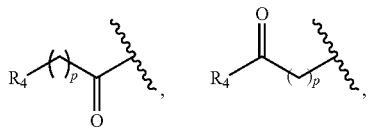

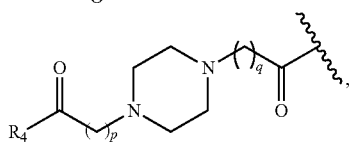

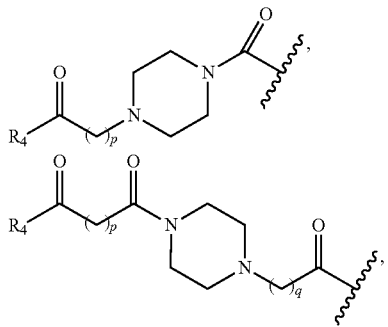

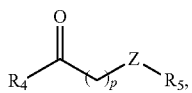

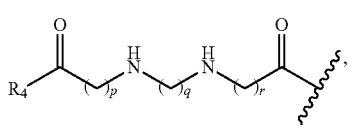

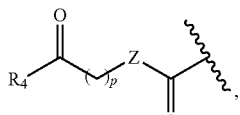

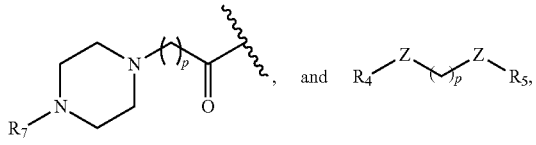

wherein
p is 0, 1, 2, 3, 4 or 5; q is 1, 2, 3, 4 or 5; and r is 1, 2, 3, 4 or 5;

$R_4$ is a group selected from:

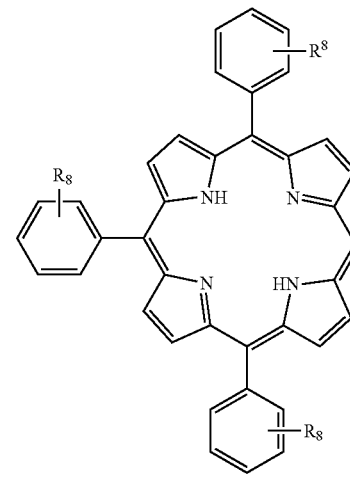

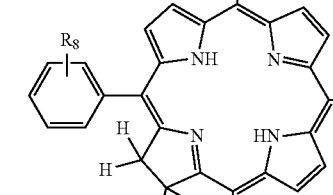

and

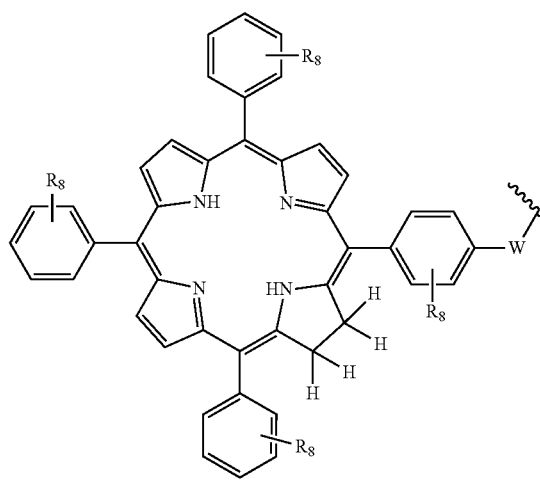
(preferably $R_4$ is selected from:
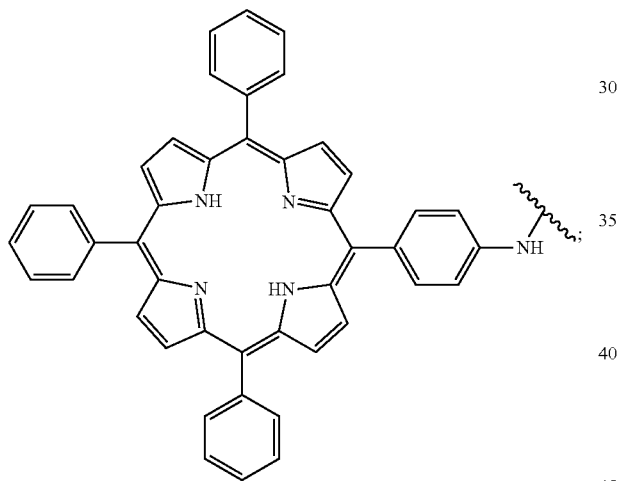
TPPa
TPCa₁
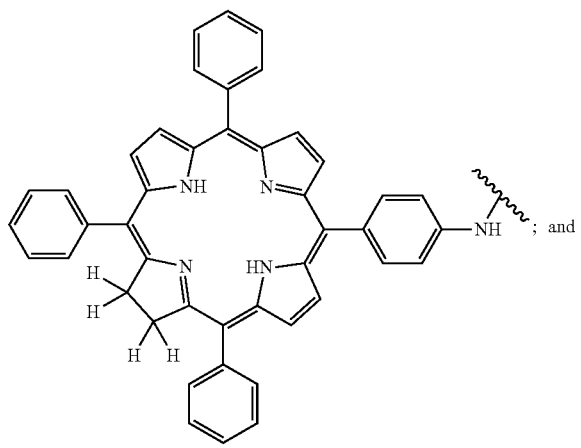
; and
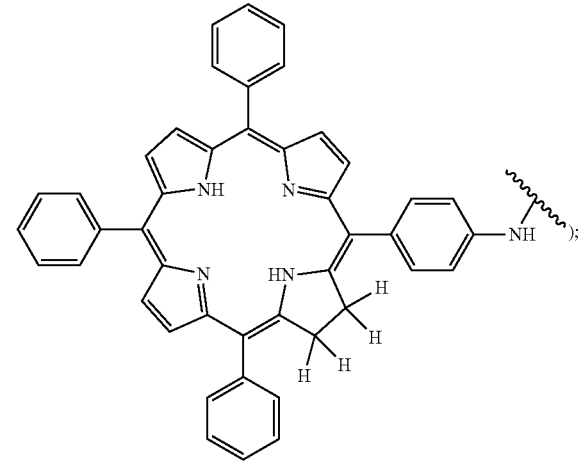
W is a group selected from O, S, NH or N(CH₃);
$R_5$ is a group selected from: —(CH₂)ₛ—CO—; —(CH₂)ₛ—Z—(CH₂)ₜ—CO— and —(CH₂)ₛ—Z—(CH₂)ₜ—Z—CO—; wherein s is 0, 1, 2, 3, 4 or 5; t is 0, 1, 2, 3, 4 or 5;
Z is NH, O, S, or SO₂,
$R_6$ is a group selected from —CN and CH₃,
$R_7$ is a group selected from:
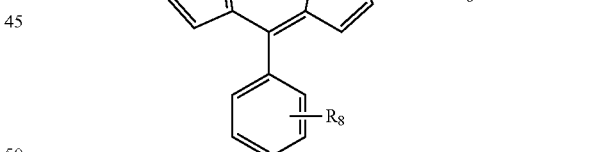
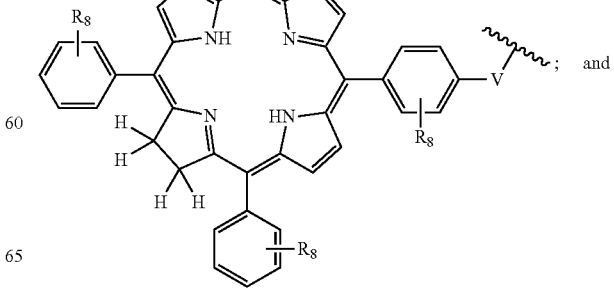
; and

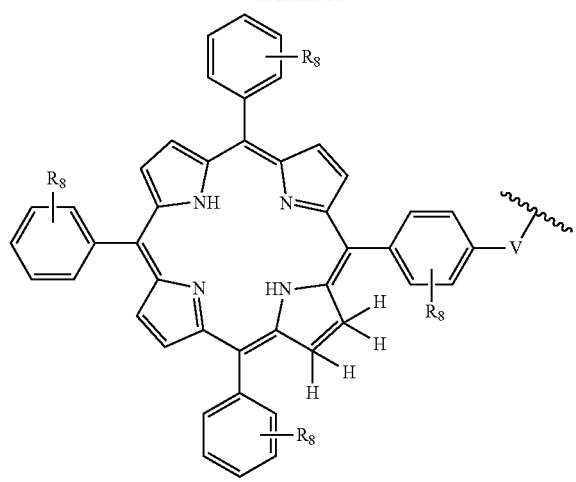

V is a group selected from CO, SO$_2$, PO, PO$_2$H or CH$_2$; (preferably R$_7$ is selected from:

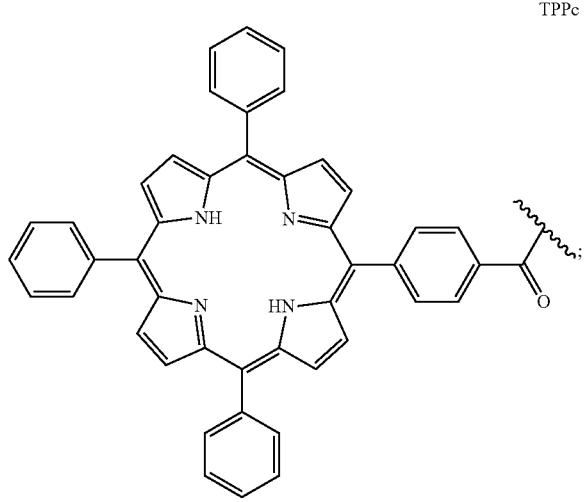

TPPc

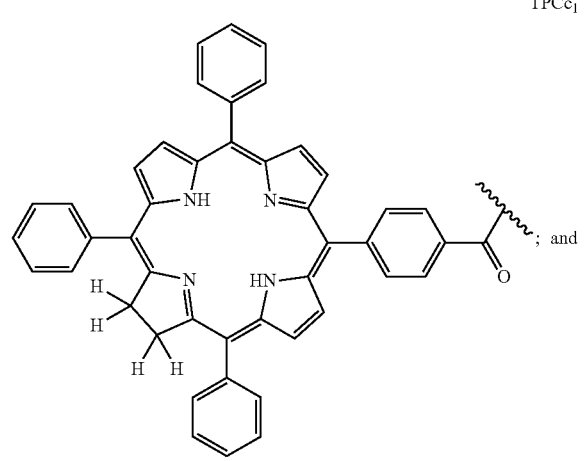

TPCc$_1$ ; and

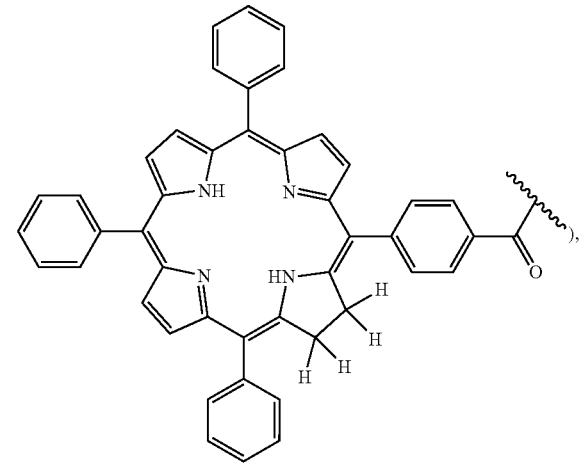

TPCc$_2$

R$_8$ is a group (substituted in the o, m or p position), which may be the same or different, selected from H, —OH, —OCH$_3$, —CH$_3$, —COCH$_3$, C(CH$_3$)$_4$, —NH$_2$, —NHCH$_3$, —N(CH$_3$)$_2$ and —NCOCH$_3$ (wherein preferably each R$_8$ is H or at least one R$_8$ is not H)
wherein each R group may be the same or different.

The chitosan polymer has at least 3 units (n=3). However, preferably n is at least 10, 20, 50, 100, 500, 1000 e.g. from 10 to 100 or 10 to 50.

As mentioned above, the photosensitisers employed in the conjugates are porphyrin and chlorin derivatives, in particular TPP$_a$, TPC$_{a1}$, TPC$_{a2}$, TPP$_{a2}$, TPC$_{c1}$ and TPC$_{c2}$. Preferably, said photosensitizer derivative R$_4$ or R$_7$ is TPC$_{a1}$, TPC$_{a2}$, TPC$_{c1}$ or TPC$_c$, especially preferably TPC$_{a1}$ or TPC$_{a2}$.

The chitosan derivative of the conjugate can have various degrees of substitution (DS) with the above R groups. For example, where present, one or more of the R groups described above may comprise less than 1%, preferably from 0.1 to 1.0%, or more than 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.5 or 99.9% of the chitosan substitutions. As noted above, group A and group B R groups each provide 0.1%-99.9% (preferably 0.5 to 99.5%) of the total Rn groups. Preferably group A provides at least 50%, preferably at least 60, 70, 80, 90 or 95% of the total Rn groups. Especially preferably group A provides between 50 and 95%, e.g. 70 and 95% of the total Rn groups. Preferably group B provides less than 50%, e.g. less than 40, 30, 20, 10 or 5% of the total Rn groups. Especially preferably, group B provides between 5 and 30%, e.g. 10-25% of the total Rn groups.

The group A R groups (or group B R groups) may be the same or different. In preferred aspects where different groups are present, e.g. in the group A R groups, the proportion of each group may vary. For example, one R group may be present in a range of e.g. 75 to 95% (of the total Rn groups) as a major component, whereas the other R group may be present in a range of e.g. 0.1 to 10% (of the total Rn groups) as a minor component. However, in the alternative, the major component may be present at lower levels (e.g. 50 to 90%) and the minor component may be present at higher levels (e.g. 0.1 to 50%). Preferably when the A R groups which are present reflect acetylation of the chitosan molecule, i.e. R is

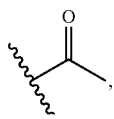

it is present at <1% of the total Rn groups. This R group tends to reflect the degree of acetylation (DA) of the starting chitosan molecules used for the generation of compounds of the invention and hence its prevalence may vary. Preferably it provides <60% of the total Rn groups, preferably less than 30% or 20%, e.g. between 0.1 and 30% of the total Rn groups.

As will be appreciated, the total % provided by all of the group A and B R groups is 100% and selection from within the above ranges is made accordingly.

It will be noted that depending on the method of synthesis used, some impurities or alternative products may be present at low levels, e.g. trace amounts of other R groups or residual protecting groups (e.g. TBDMS) may remain in the final product. However, such trace components or compounds, if present, are present at <1% of the total (preferably <0.1%) and do not affect functionality. Compounds or compositions including such trace components or compounds fall within the scope of the invention.

In the preferred aspects described herein, the % of the selected R group as a proportion of the total Rn groups is provided. In such cases, a range of % is preferred (e.g. to reflect variation in manufacturing). Preferably the range is 5%, i.e. when reference is made to 90% of A R groups having a certain structure, this extends to compounds with 85 to 95% of that A R group, and so forth.

Preferred A R groups are:

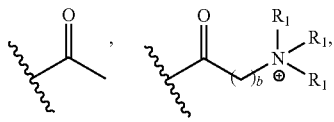

wherein preferably each $R_1$ is $CH_3$ and b is 1;

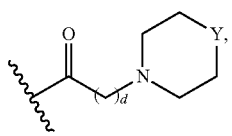

wherein preferably Y is —$NCH_3$ and d is 1;

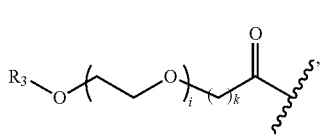

wherein preferably j is 0 or 1; i is 3 or 6 and k is 1;

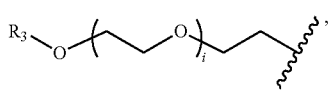

wherein preferably j is 1 and i is 2;

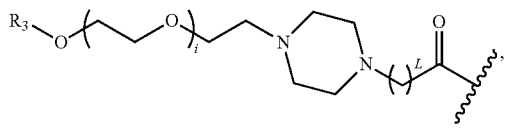

wherein preferably j is 0 or 1 and i is 2, 4 or 5 (e.g. 2 or 4) and L is 1;

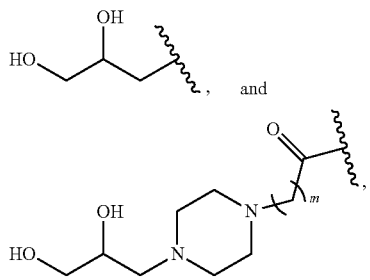

wherein preferably m is 1.

Preferably the above R groups are present as major components (i.e. greater than 75% of the total Rn groups (as discussed above) or minor components (i.e. less than 10% of the total Rn groups (as discussed above)). Preferably the group

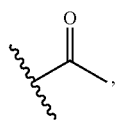 [SMILES: *C(C)=O]

is present only as a minor component.

Preferred B R groups are:

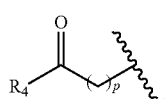

wherein preferably p is 1;

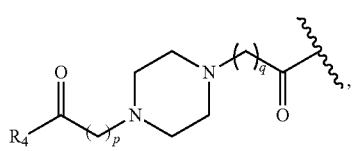

wherein preferably p is 1 and q is 1;

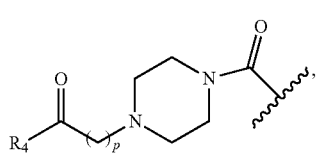

wherein preferably p is 1;

and

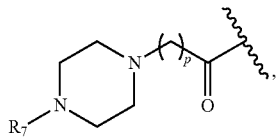

wherein preferably p is 1.
Especially preferred A R groups are:

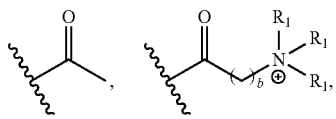

wherein preferably each $R_1$ is $CH_3$ and b is 1;

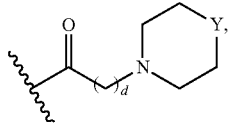

wherein preferably Y is —$NCH_3$ and d is 1;

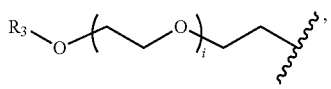

wherein preferably j is 1 and i is 2; and

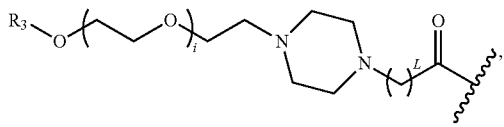

wherein preferably j is 0 or 1 and i is 2, 4 or 5 (e.g. 2 or 4) and L is 1.
Especially preferred B R groups are:

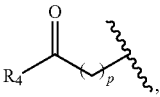

wherein preferably p is 1;

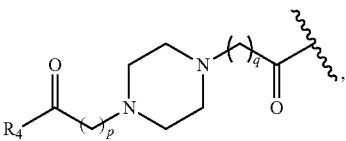

wherein preferably p is 1 and q is 1; and

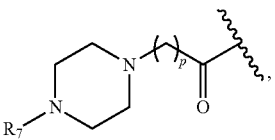

wherein preferably p is 1.

Preferred R groups and their relative prevalence in the total Rn groups are provided in the table below in which the different possible R groups are shown which conjugate with the chitosan. The predominance of each type of R group is indicated in brackets and may vary within 5% either side of the indicated value. Group B R groups have attached photosensitizer groups $R_4$ or $R_7$.

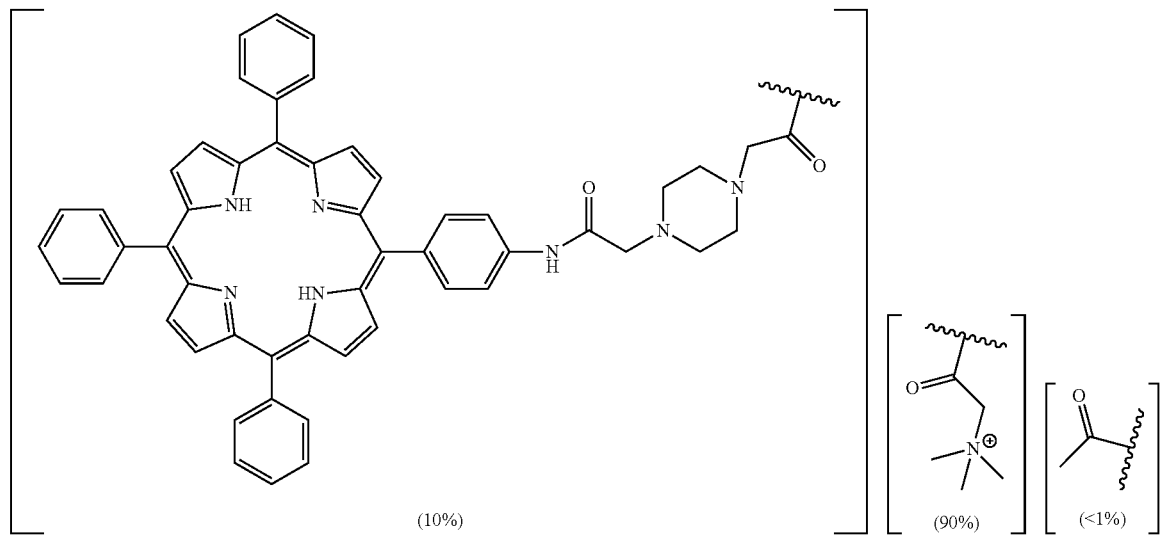

-continued
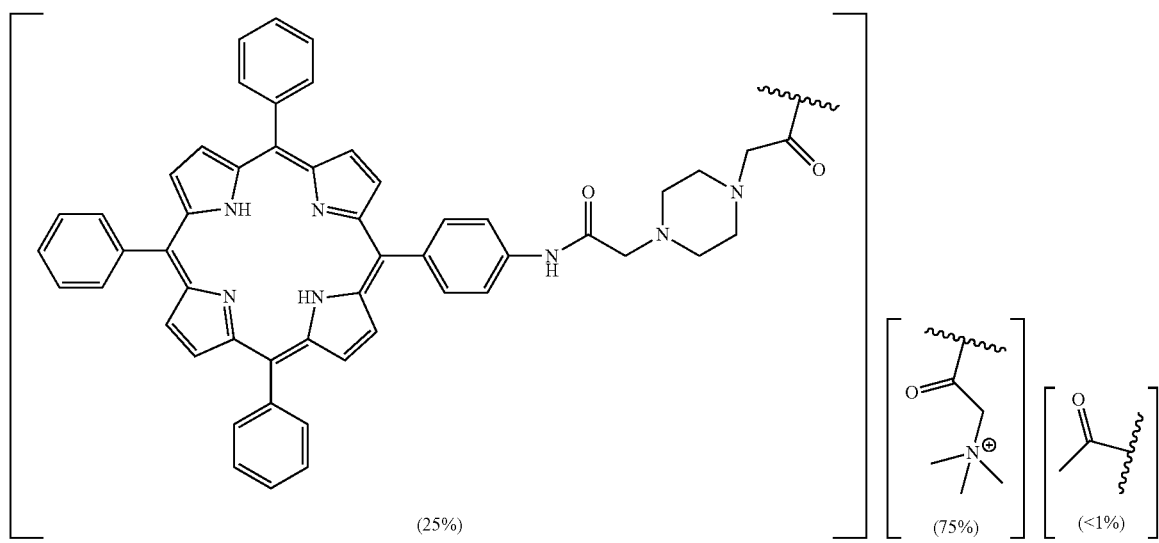
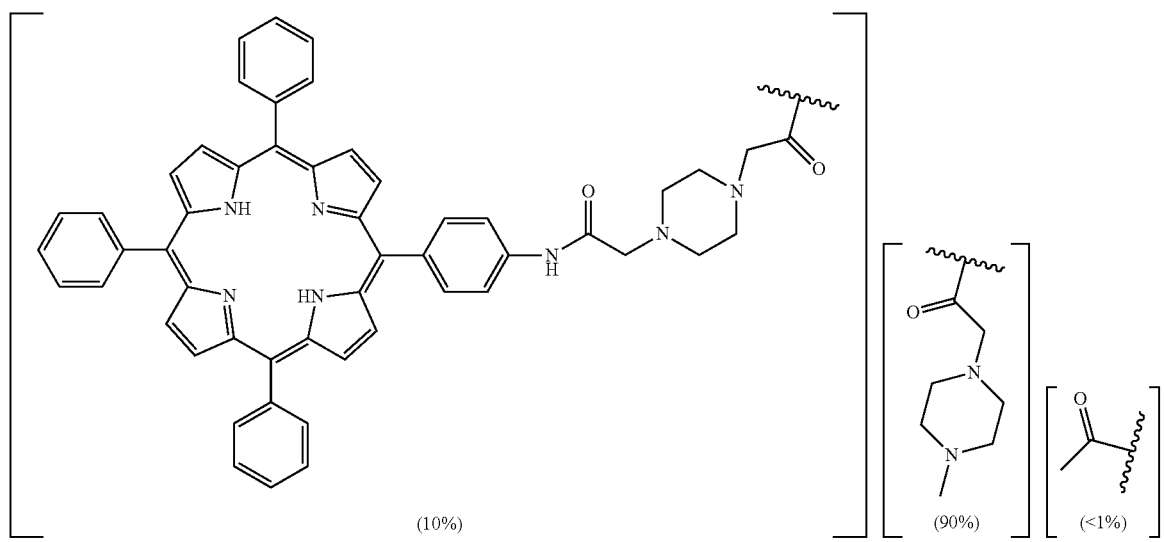
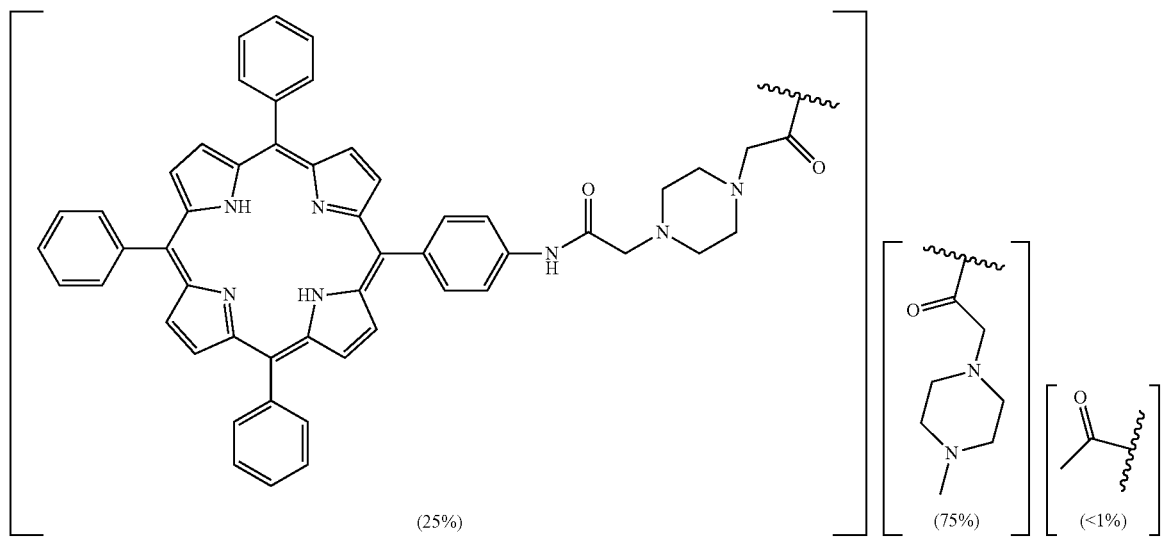

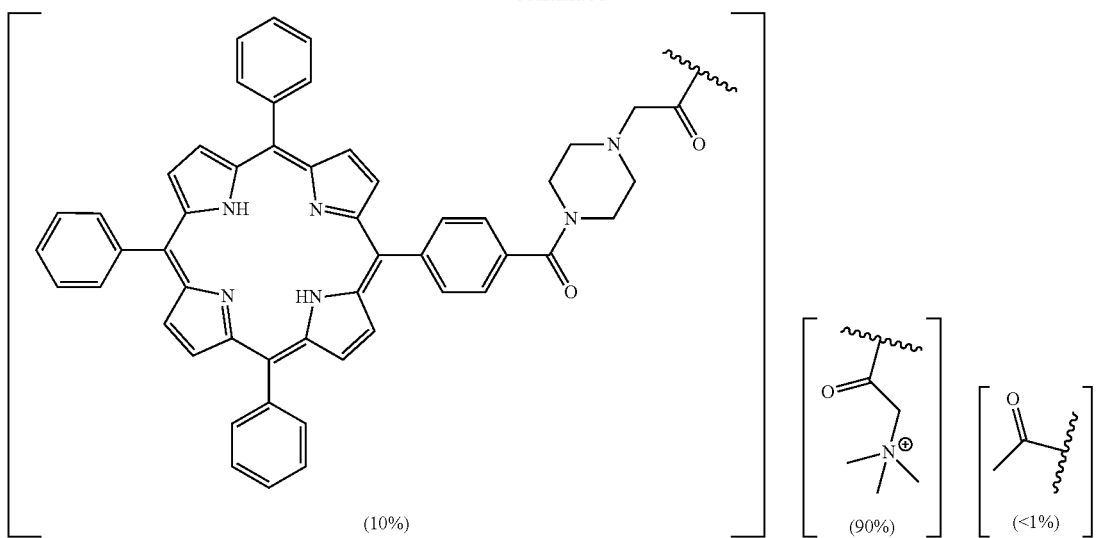
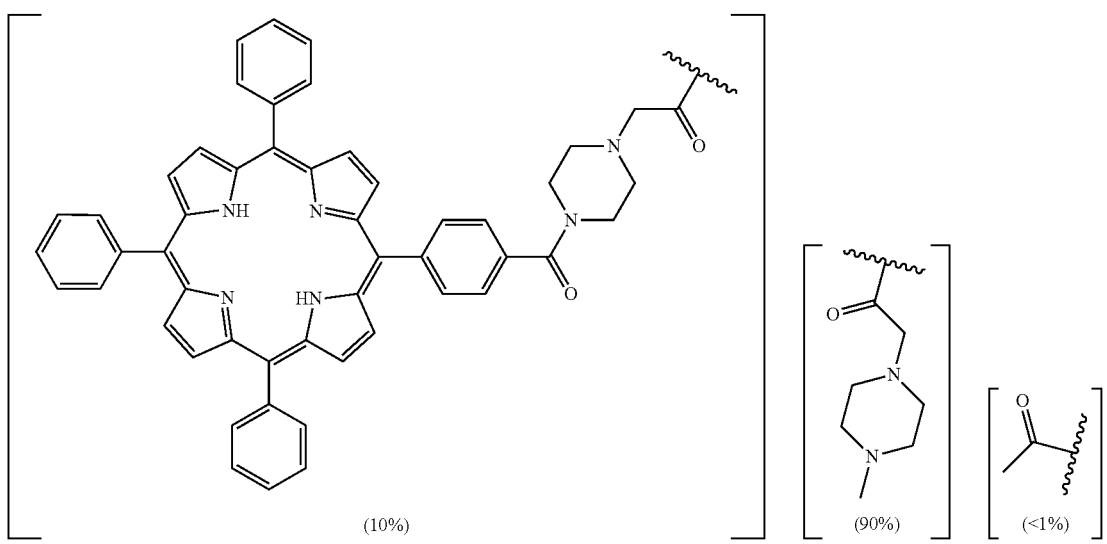
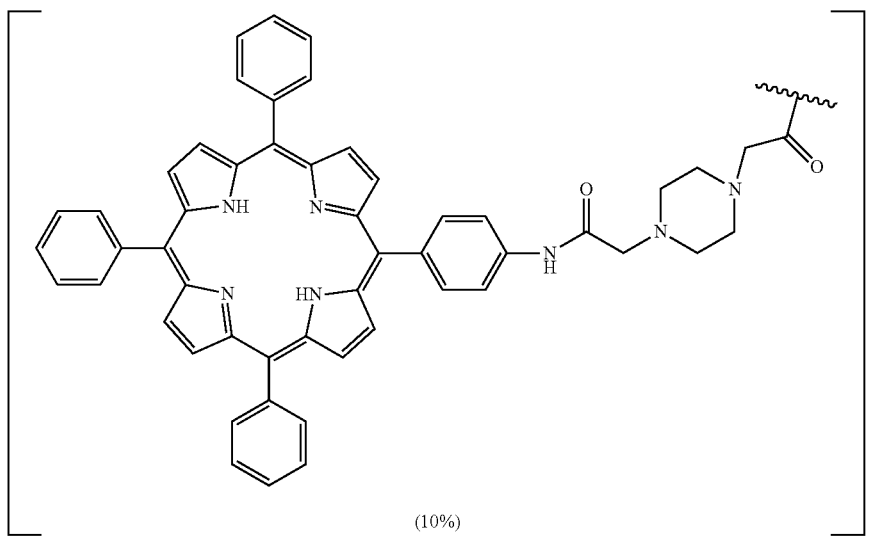

-continued
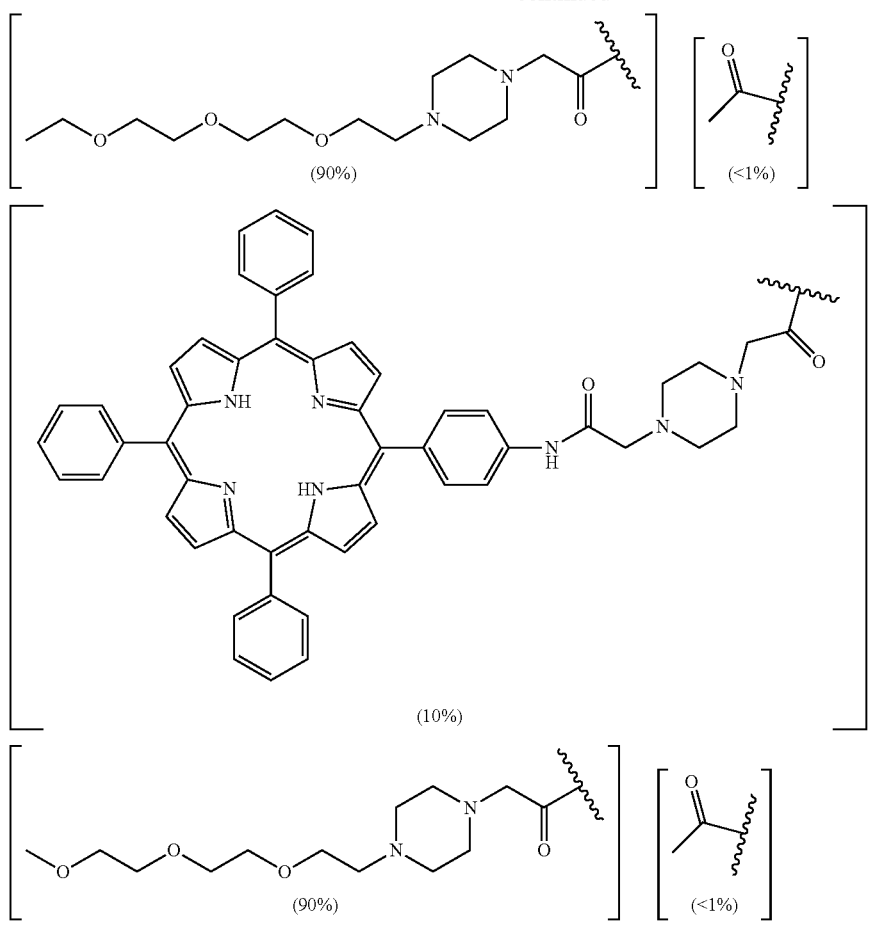
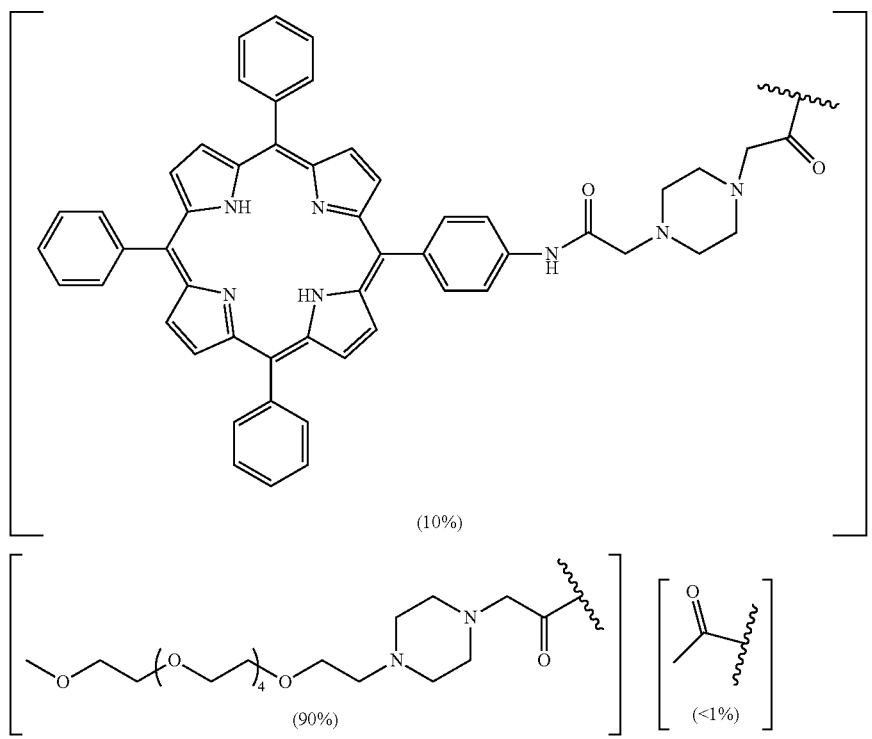

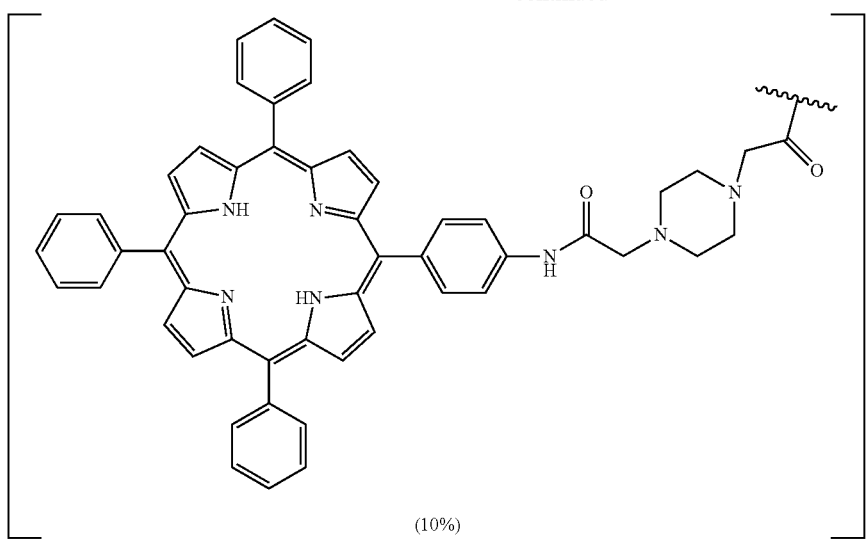
(10%)
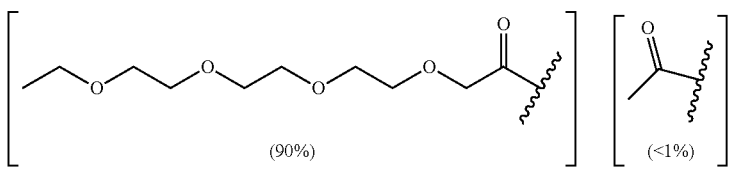
(90%) (<1%)
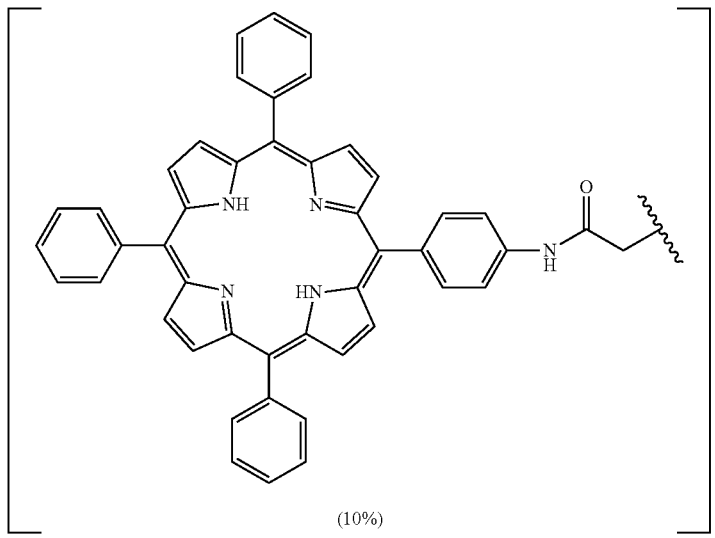
(10%)
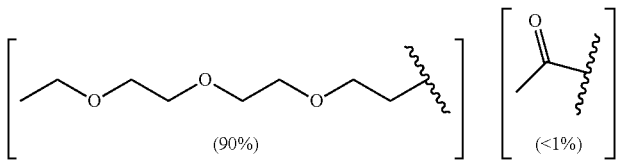
(90%) (<1%)

-continued
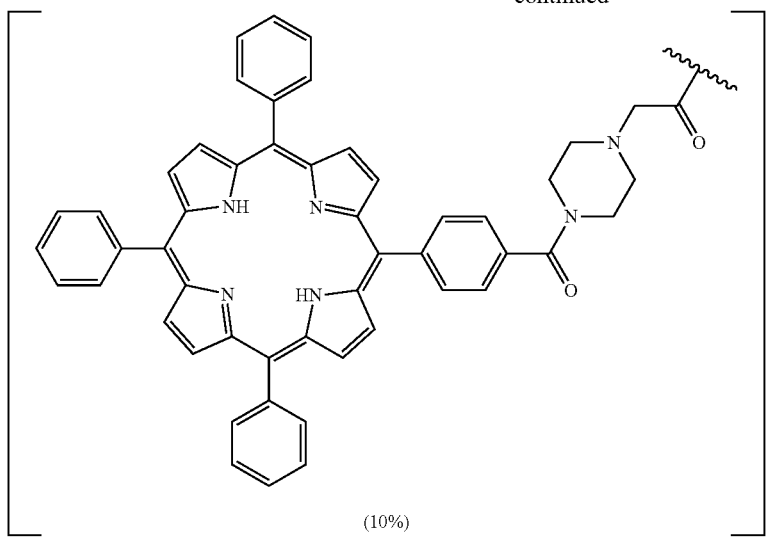
(10%)
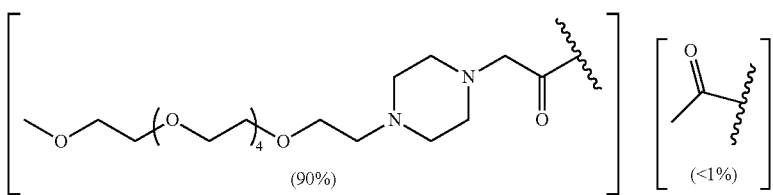
(90%)    (<1%)
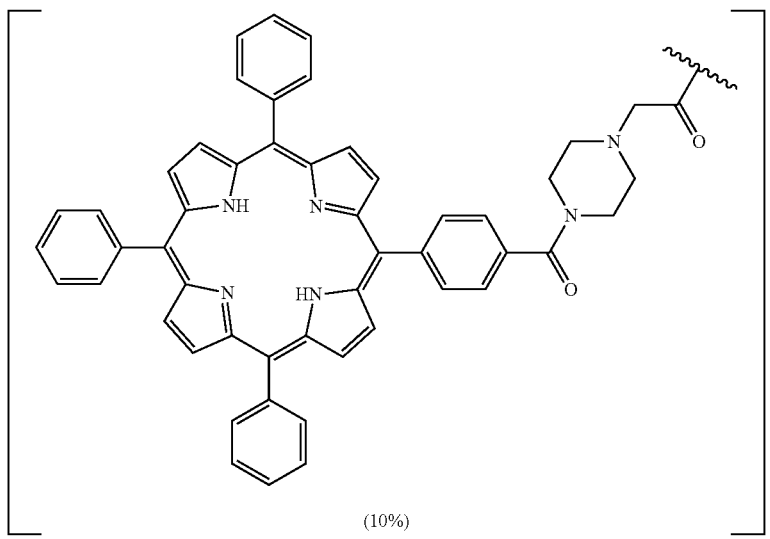
(10%)
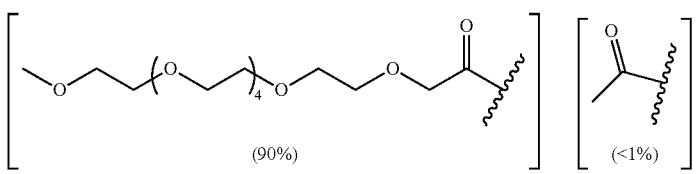
(90%)    (<1%)

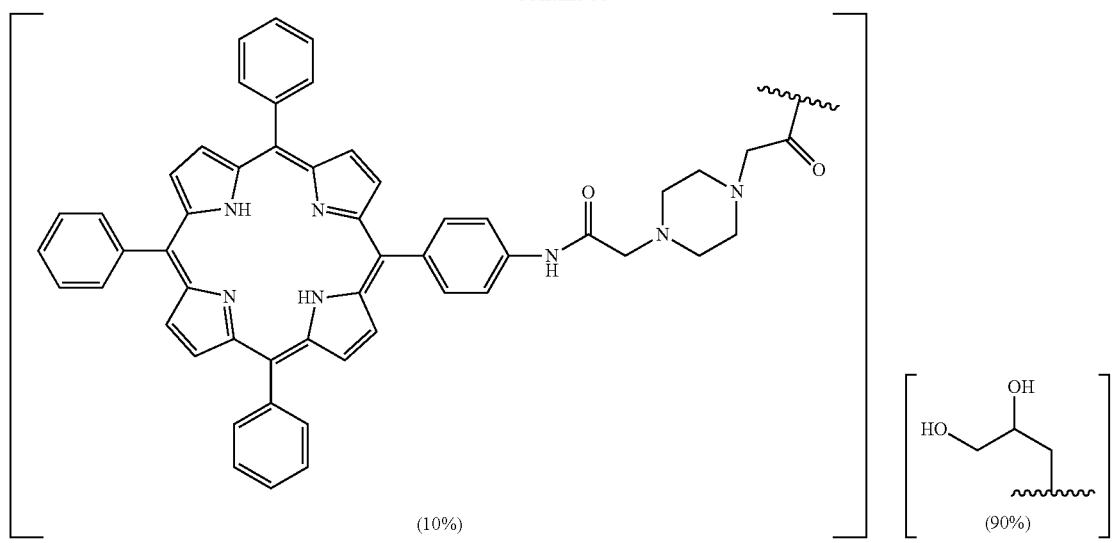
(10%) (90%)
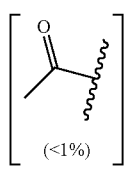
(<1%)
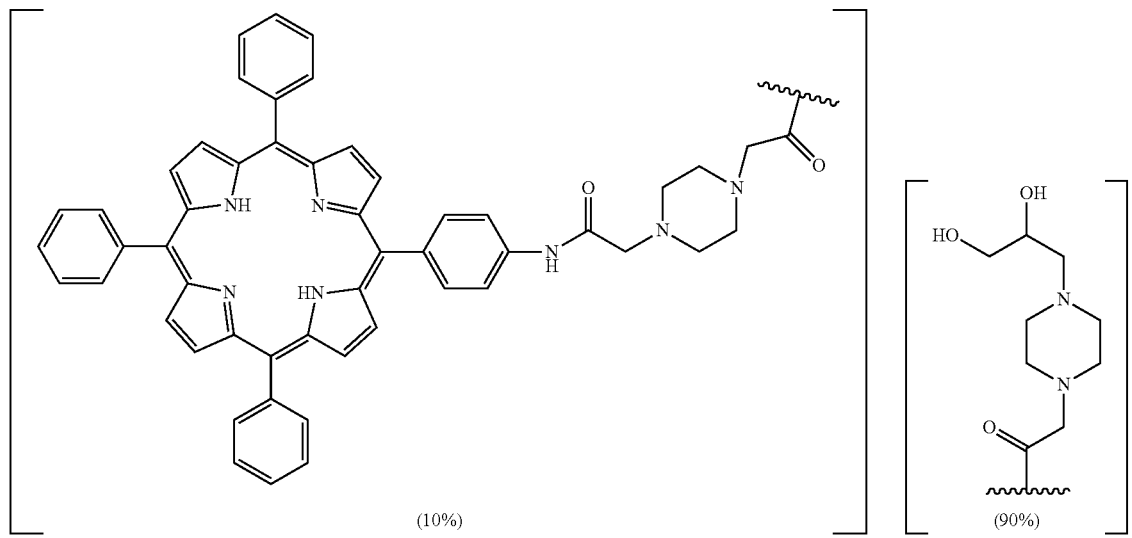
(10%) (90%)
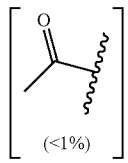
(<1%)

-continued
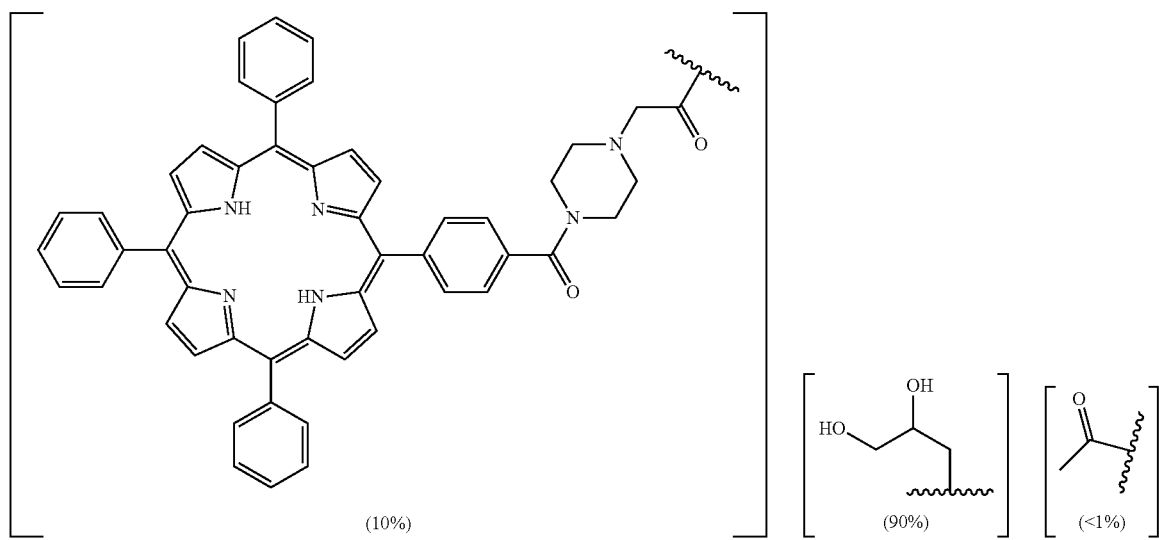
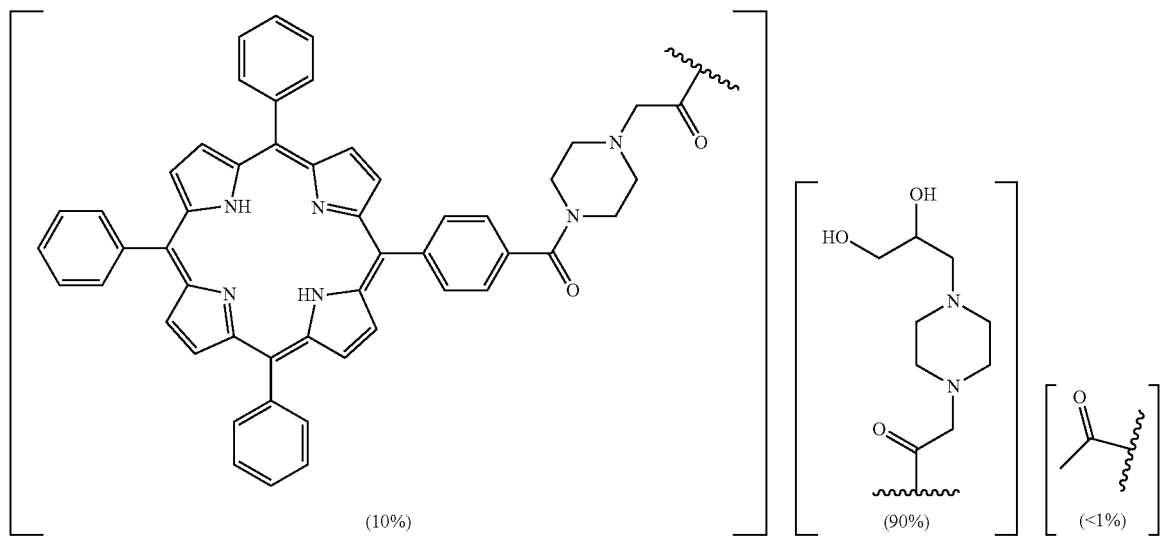
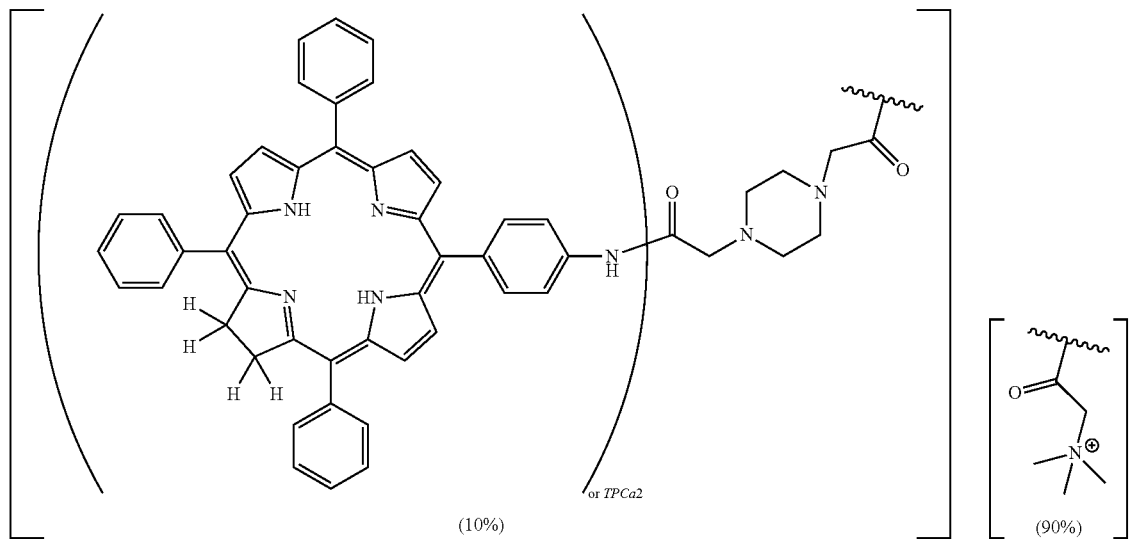

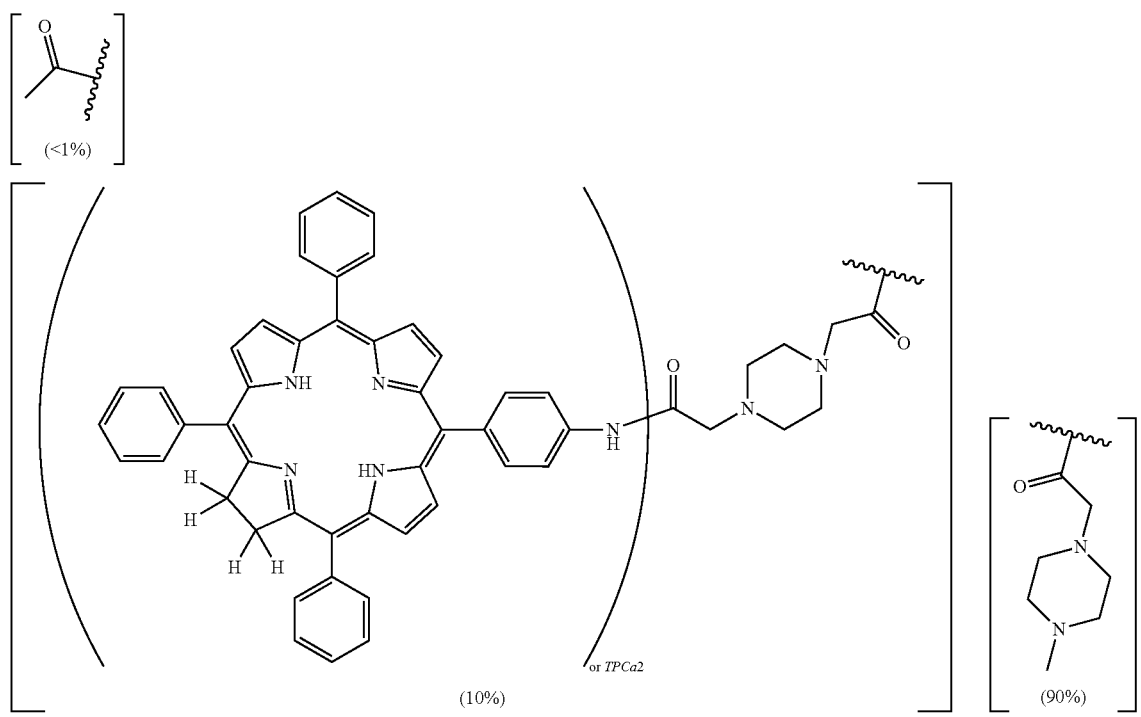
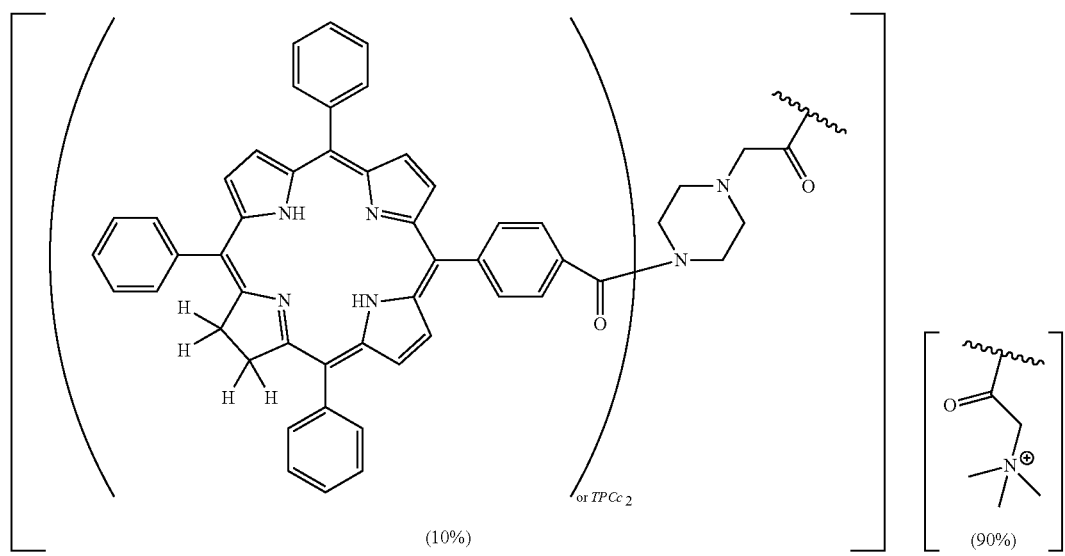

-continued
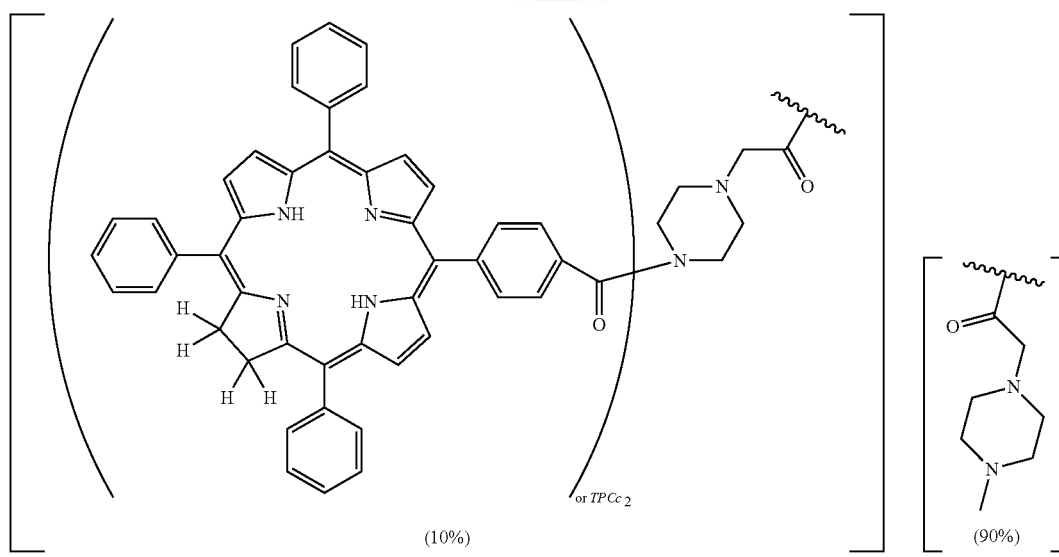
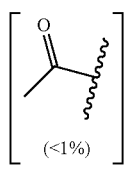
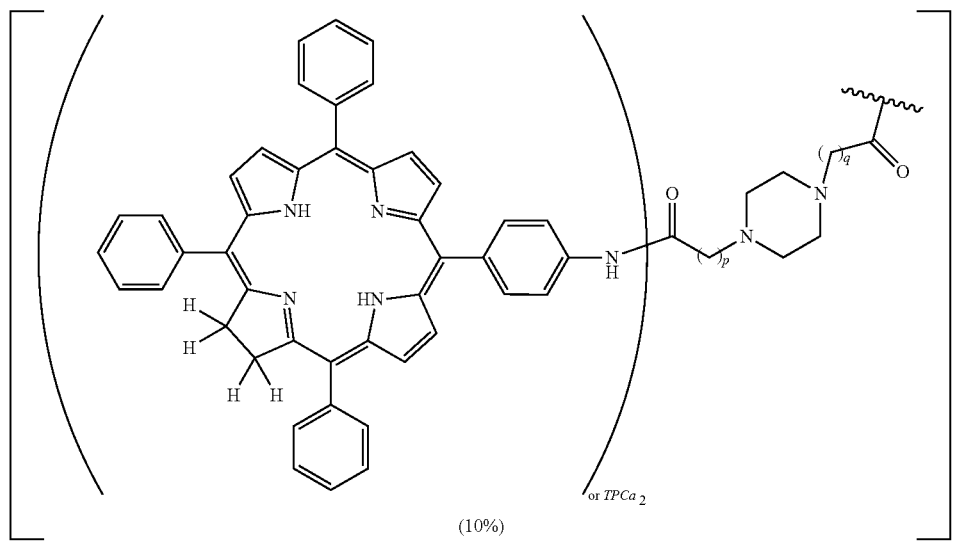
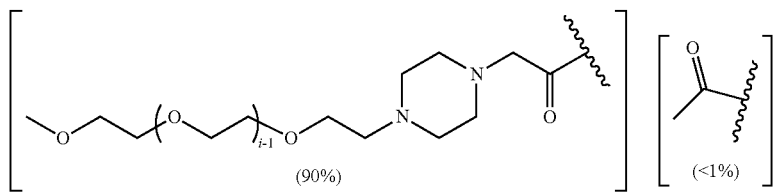

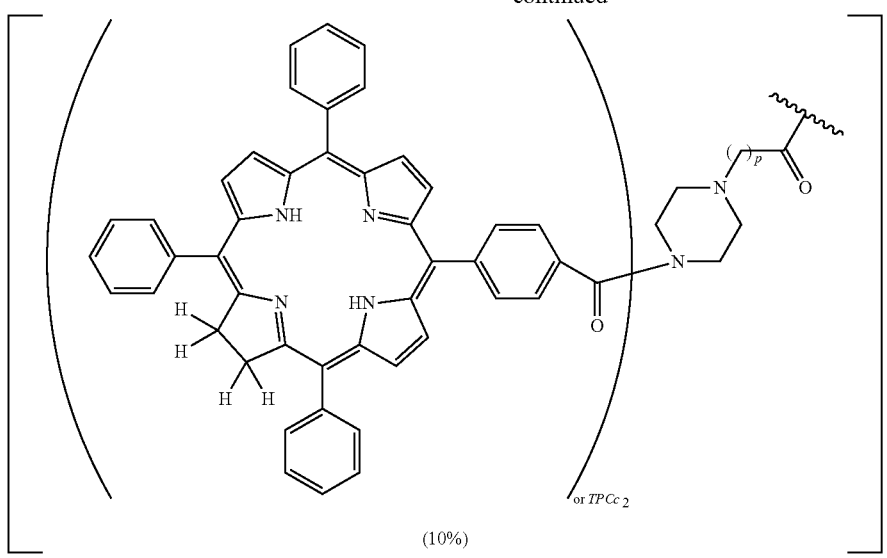
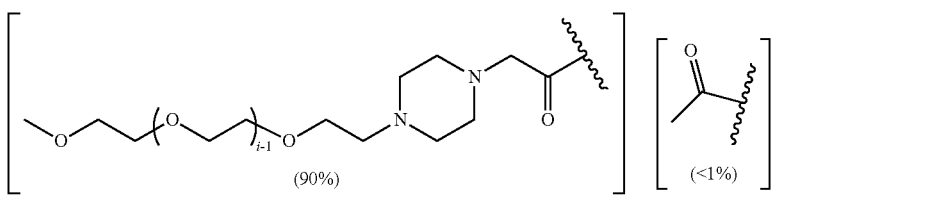
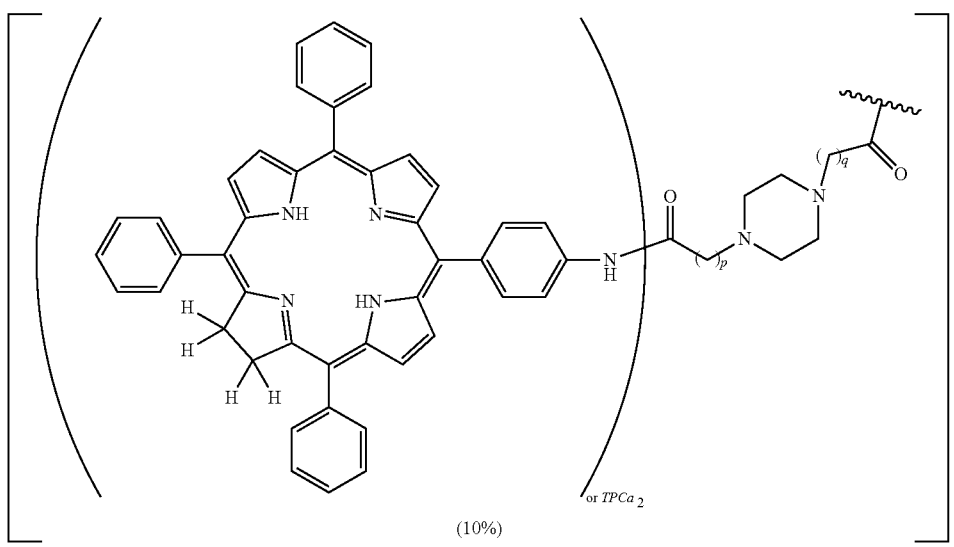
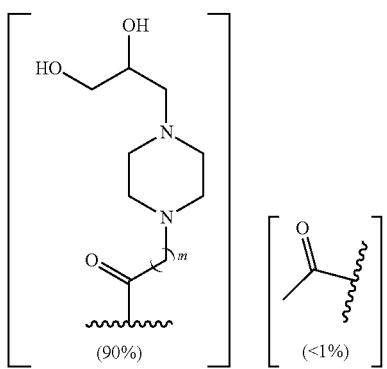

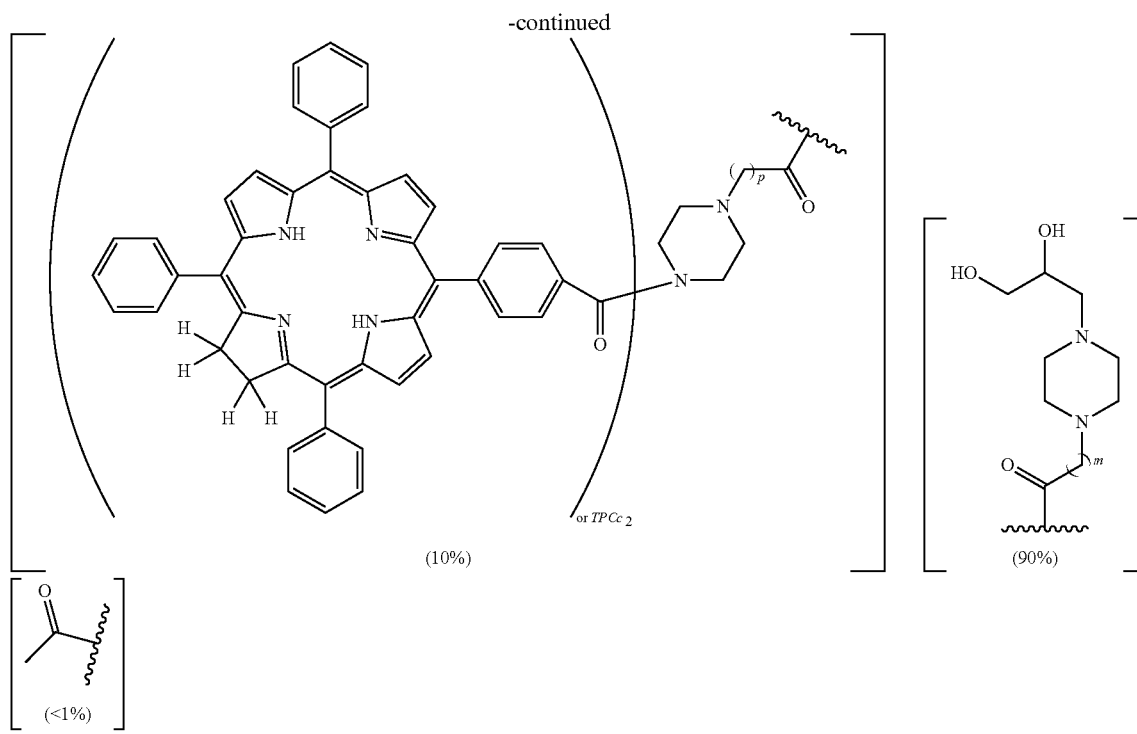

Particularly preferred compounds of the invention are also as shown in FIG. 1 in which the prevalence of the R groups is indicated but this may vary by up to 5% either side of the indicated value. In each case the R group with the attached photosensitizer has the lower indicated prevalence.

The compounds of the invention may be prepared as described herein in the Examples. The synthesis methods use procedures standard in the art, which will be familiar to the skilled man, and which are described in the below Examples. PEGylation and TEGylation to provide relevant R groups can be carried out according to standard methods in the art. The present invention also extends to methods of preparing the compounds of the invention, for example as described in the Examples and schemes described herein.

The compounds of the invention have low toxicity and therefore are suitable for a variety of medical indications.

The compounds of the present invention are particularly suitable for use in PCI methods. As exemplified in the present Examples, it has been shown that compounds of the present invention have surprisingly good efficacy in internalising molecules into a cell. In Example 3 it is shown that the efficacy of a compound of the invention was considerably better than the efficacy achieved with a sensitizer alone (in this case the photosensitizer $TPCS_{2a}$ was used which has been specially designed for use in PCI, and which is under clinical development for cancer treatment (Berg et al. 2011, Photochem. Photobiol. Sci., 10, p 1637-1651)). When compared to $TPCS_{2a}$ the compounds of the invention were up to at least 10 times more active, i.e. even when used at a 10 times lower concentration the conjugates gave a substantially greater enhancement of transfection than that observed with $TPCS_{2a}$ (see FIGS. 19 and 20).

The basic method of photochemical internalisation (PCI), is described in WO 96/07432 and WO 00/54802, which are incorporated herein by reference. In summary, the molecule to be internalised and a photosensitising agent, in the present case a photosensitiser as part of a compound of the present invention, are brought into contact with a cell. The photosensitising agent and the molecule to be internalised are taken up into a cellular membrane-bound subcompartment within the cell. On exposure of the cell to light of the appropriate wavelength, the photosensitizing agent is activated which directly or indirectly generates reactive species which disrupt the intracellular compartment membranes. This allows the internalized molecule to be released into the cytosol.

These methods use the photochemical effect as a mechanism for introducing otherwise membrane-impermeable (or poorly permeable) molecules into the cytosol of a cell in a manner which does not result in widespread cell destruction or cell death if the methodology is suitably adjusted to avoid excessive toxic species production, e.g. by lowering illumination times or photosensitizer dose.

As such, the invention also provides a method for introducing a molecule into the cytosol of a cell, comprising contacting said cell with the molecule to be introduced and a compound of the invention, and irradiating the cell with light of a wavelength effective to activate the photosensitising agent of the compound. Once activated, intracellular compartments within said cell containing said compound release the molecule contained in these compartments into the cytosol. Use of a compound of the invention for internalising a molecule which it is desired to internalise also forms part of the invention.

PCI can effect transfection of a number of different types of molecules into a cell. For example the molecule may be selected from DNA or antisense DNA; oligo(deoxy)nucleotides; RNA, such as mRNA, siRNA, double stranded (ds)RNA, single stranded (ss)RNA or antisense RNA; PNA, sugars; proteins; peptides; membrane impermeable drugs; other membrane impermeable molecules, or covalently or non covalently bound combinations of the above mentioned molecules. Preferably the molecules to be introduced are not internalized (i.e. into the cytosol) significantly without the assistance of PCI, e.g. their internalization is limited such that fewer than 50% (e.g. less than 30 or 10%) of cells to which they are applied internalize one or more of the molecules into the cytosol in a 4 hour time period.

The molecule to be internalised may be selected to achieve various results, e.g. to alter, e.g. reduce or increase expression of a target gene or to have an effect on the properties or viability of the cells. To affect gene expression, the molecule to be transferred may be a sense or antisense oligo or poly-nucleotide, e.g. a gene sequence for example in a plasmid or an antisense oligonucleotide or siRNA molecule. Such methods may be useful in treating or preventing diseases and disorders, such as cancer, and may also be useful in gene therapy applications.

The method of the invention achieves translocation of the molecule to be internalised into the cytosol. It will be appreciated, however, that uptake of each and every molecule contacted with the cell into the cytosol is not achievable. Significant and improved internalization relative to background levels in which no PCI or compound of the invention is used is, however, achievable.

Preferably methods of the invention allow the internalization of molecules at sufficient levels that their effect is evident for example in the expressed products of those cells or by the effects on the cell. The appropriate concentration of the molecule to be contacted with the cell may be adjusted to achieve this aim, for example in some applications it may be desirable to achieve an elevation or reduction in expression of a target gene (or introduced gene) or cell death after introduction of a cytotoxic molecule. The reduction or cell death may be of at least 10%, e.g. at least 20, 30, 40 50, 60, 70, 80 or 90% reduction (e.g. in the expression of one or more proteins encoded by the target gene) or cell death after incubation with cells for e.g. 24, 48, 72 or 96 hours (e.g. 24 to 48 hours). Elevation of expression may be assessed relative to existing levels which may be zero when an non-endogenous molecule is used and numerically similar levels to those mentioned above for reduction may be achieved. Similarly, the compound (of the invention) type and/or concentration, and the irradiation time can be adjusted to achieve the reduction set out above.

Levels of expressed products can be measured, for example, by determining the level of protein in the cell, using standard techniques known in the art such as Western Blotting. The level of reduction of the protein is dependent on the half-life of the protein, i.e. pre-existing protein will be removed in accordance with its half-life. Cell death may be determined by any appropriate means.

The effects of introduced genetic material can also be measured in terms of expression levels of e.g. mRNA that is present in the cell, e.g. the method can be carried out to achieve an elevation or reduction in mRNA levels of at least 10%, e.g. at least 20, 30, 40, 50, 60, 70, 80 or 90% elevation or reduction after incubation with cells for e.g. 24, 48, 72 or 96 hours e.g. 24 to 48 hours, relative to mRNA levels of the target or introduced sequence at the same time point without addition of the genetic material. This can also be measured using standard techniques known in the art such as hybridisation or blotting techniques and RT-PCR.

The term "cell" is used herein to include all eukaryotic cells (including insect cells and fungal cells). Representative "cells" thus include all types of mammalian and non-mammalian animal cells, plant cells, insect cells, fungal cells and protozoa. Preferably, however, the cells are mammalian, for example cells from cats, dogs, horses, donkeys, sheep, pigs, goats, cows, mice, rats, rabbits, guinea pigs, but most preferably from humans.

As used herein "contacting" refers to bringing the cells and the photosensitizing agent containing compound of the invention and/or the molecule to be introduced into physical contact with one another under conditions appropriate for internalization into the cells, e.g. preferably at 37° C. in an appropriate nutritional medium, e.g. from 25-39° C.

"Irradiation" of the cell to activate the photosensitising agent refers to the administration of light directly or indirectly as described hereinafter. Thus cells may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells.

The light irradiation step to activate the photosensitising agent may take place according to techniques and procedures well known in the art. The wavelength and intensity of the light is selected according to the photosensitising agent used. Suitable artificial light sources are well known in the art, e.g. using blue (450-475 nm) or red (620-750 nm) wavelength light.

The time for which the cells are exposed to light in the methods of the present invention may vary. The efficiency of the internalisation of a molecule into the cytosol increases with increased exposure to light to a maximum beyond which cell damage and hence cell death increases.

A preferred length of time for the irradiation step depends on factors such as the target, the photosensitizer (in the compound of the invention), the amount of the photosensitizer accumulated in the target cells or tissue and the overlap between the absorption spectrum of the photosensitizer and the emission spectrum of the light source. Generally, the length of time for the irradiation step is in the order of seconds to minutes or up to several hours, e.g. preferably up to 60 minutes e.g. from 0.25 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Shorter irradiation times may also be used, for example 1 to 60 seconds, e.g. 10-50, 20-40 or 25-35 seconds.

Appropriate light doses can be selected by a person skilled in the art and again will depend on the photosensitizer (in the compound of the invention) used and the amount of photosensitizer accumulated in the target cells or tissues. For example, the light dose typically used for photodynamic treatment of cancers with the photosensitizer Photofrin and the protoporphyrin precursor 5-aminolevulinic acid is in the range 50-150 J/cm$^2$ at a fluence range of less than 200 mW/cm$^2$ in order to avoid hyperthermia. The light doses are usually lower when photosensitizers with higher extinction coefficients in the red area of the visible spectrum are used. For PCI methods lower doses may be used, e.g. a light dose in the range of 5-25 J/cm$^2$ at a fluence range of 75-150 mW/cm$^2$. Furthermore, for treatment of non-cancerous tissues with less photosensitizer accumulated the total amount of light needed may be substantially higher than for treatment of cancers. Furthermore, if cell viability is to be maintained, the generation of excessive levels of toxic species is to be avoided and the relevant parameters may be adjusted accordingly.

The PCI methods of the invention may inevitably give rise to some cell killing by virtue of the photochemical treatment i.e. by PDT effects through the generation of toxic species on activation of the photosensitizing agent. Depending on the proposed use, this cell death may not be of consequence and may indeed be advantageous for some applications (e.g. cancer treatment).

In one embodiment the invention provides a method of achieving death of a cell comprising contacting said cell with a compound of the invention, and irradiating the cell with light of a wavelength effective to activate the photosensitising agent of the compound to generate reactive oxygen species which cause death of said cell. When cell death (by PDT) is to be achieved, the timing, intensity and wavelength for the irradiation step is selected appropriately to optimally achieve cell death of the target cells.

In some embodiments of the present invention, however, cell death is avoided for example when inhibition of expression of a gene in the absence of cell toxicity is desirable or if cell death is instead to be achieved by the introduced molecule. For example, in some uses it is highly advantageous to achieve inhibition of gene expression or expression in the absence of general cell toxicity or an effect on cell viability, for example in some gene therapy approaches. The methods of the invention may be modified such that the fraction or proportion of the surviving cells is regulated by selecting the light dose in relation to the concentration of the photosensitizing agent (in the compounds of the invention). Again, such techniques are known in the art.

In applications in which viable cells are desirable, substantially all of the cells, or a significant majority (e.g. at least 50%, more preferably at least 60, 70, 80 or 90% of the cells) are not killed. Cell viability following PCI treatment can be measured by standard techniques known in the art such as the MTS test.

Regardless of the amount of cell death induced by the activation of the photosensitiser, in some applications it is important that the light dose is regulated such that some of the individual cells wherein the PCI effect is manifested are not killed by the photochemical treatment alone (although they may subsequently be killed by molecules introduced into the cells if those molecules have a cytotoxic effect).

Cytotoxic effects may be achieved by using for example introducing a cytotoxic molecule (e.g. a cytotoxic peptide such as gelonin or bleomycin) or gene therapy in which an agent, for example a gene, antisense oligonucleotide or siRNA molecule, is internalized into a tumour cell by the method of the invention.

The compounds and methods of the invention may be used in vitro or in vivo, for example either for in situ treatment or for ex vivo treatment followed by the administration of the treated cells to the body, for various purposes including inhibition or elevation of expression of specific gene products e.g. in gene therapy methods.

Thus, a further aspect of the invention provides a composition (e.g. a pharmaceutical composition) containing a compound or conjugate of the invention, and optionally separately a molecule to be internalised. When said composition is a pharmaceutical composition it contains one or more pharmaceutically acceptable diluents or excipients.

In a further aspect the invention provides said compound or composition for use in therapy.

The present invention provides a kit comprising a compound or composition of the present invention as described herein and a molecule to be internalised. Preferably said kit (or product) is for simultaneous, separate or sequential use in a medical treatment, preferably for treating cancer or, as described in further detail below, for vaccination purposes.

Thus a further aspect provides the compound or composition and optionally a molecule to be internalized as defined herein for use in treating or preventing a disease, disorder or infection in a subject, preferably in which abnormal or excessive cell growth is evident or in which abnormal elevated or suppressed gene expression is evident, especially preferably wherein said disease is cancer. Methods of treatment or prevention of a disease, disorder or infection in a subject (which correspond to the uses described herein) by administering a compound or composition of the invention and optionally a molecule to be internalized are also encompassed. Preferably said treatment or prevention is achieved using a method described herein.

This method may be carried out using PCI methods or when cell death is the ultimate goal, PCI or PDT methods may be used.

Thus, the PCI method may be carried out as described above, i.e. by contacting cells in the subject with a molecule to be introduced and said compound or composition, and irradiating the cells with light of a wavelength effective to activate the photosensitising agent of the compound. Preferably the molecule to be introduced is a cytotoxic molecule, preferably bleomycin.

A PDT method may be carried out by contacting cells in the subject with said compound or composition, and irradiating the cell with light of a wavelength effective to activate the photosensitising agent of the compound to generate reactive oxygen species which cause death of said cells.

Alternatively described, the present invention provides the use of a compound or composition as described herein and optionally a molecule to be internalised into a cell in the preparation of a medicament for treating or preventing a disease, disorder or infection. Also provided is use of said compound or composition in the preparation of a medicament for said treatment or prevention wherein said treatment or prevention is as described herein. The disease, disorder or infection preferably exhibits abnormal or excessive cell growth or abnormal elevated or suppressed gene expression and/or would benefit from reduction in cell growth or suppression or elevation of expression of one or more genes.

As referred to herein, abnormal or excessive refers to what is considered normal in age and sex-matched normal individuals or other normal parts of the same individual's body. Abnormal growth may thus refer to cancers, benign tumours and excessive cell growth may refer to skin conditions such as actinic keratosis, warts and moles etc. Cancers to which the methods may be applied include head and neck cancer, cancer of the bile duct, brain cancer, melanoma, skin metastases (from different cancers), lung cancer, mesothelioma, pancreatic cancer, gastric cancer, rectal cancer, anal cancer, penis cancer, vulva cancer and oesophageal cancer. Thus the medicament may be used to treat cancer. When a molecule to be internalised is used it may be an anti-cancer chemotherapeutic agent.

Abnormal elevated or suppressed gene expression may be treated by altering expression of one or more target genes in said subject, for example when the molecule to be internalised is a gene, antisense oligonucleotide or siRNA molecule. Preferably said medicament is for gene therapy, i.e. for treating or preventing a disease, disorder or infection which is typified by abnormal gene expression or which would benefit from suppression of one or more genes. Said alteration includes down regulation of said expression.

When a PCI method is used, the compound (or composition of the invention) and the molecule to be internalised can be contacted with cells or tissues of a patient (or subject) simultaneously or sequentially and said cells are irradiated with light of a wavelength effective to activate the photosensitizing agent of said compound and irradiation is performed prior to, during or after the cellular uptake of said compound and molecule into an intracellular compartment containing said photosensitizing agent, preferably prior to cellular uptake of said transfer molecule into any intracellular compartment.

Also contemplated are methods in which cells are treated which are administered to the subject. Thus in an alternative aspect the invention provides a method of treating or preventing a disease, disorder or infection in a patient comprising introducing a compound (or composition) of the invention and optionally a molecule to be internalized into one or more cells in vitro, in vivo or ex vivo according to the methods as described hereinbefore and where necessary (i.e. when transfection is conducted in vitro or ex vivo) administering said cells to said patient. Thus the cells generated may be used in therapy or for a specific use as described hereinbefore.

As referred to herein a subject is an animal, preferably a mammalian animal, e.g. a cow, horse, sheep, pig, goat, rabbit, cat, dog, especially preferably a human.

As defined herein "treatment" refers to reducing, alleviating or eliminating one or more symptoms of the disease, disorder or infection which is being treated, relative to the symptoms prior to treatment. "Prevention" refers to delaying or preventing the onset of the symptoms of the disease, disorder or infection.

Compositions of the present invention may also comprise a cell containing an molecule which has been internalised into the cytosol of said cell by a method of the invention. The invention further extends to such compositions for use in therapy, particularly cancer or gene therapy.

Thus, a yet further aspect of the invention provides a cell or a population of cells containing a molecule which has been internalised into the cytosol of said cell, which cell is obtainable by a method of the present invention.

A yet further aspect of the invention provides the use of such a cell or population of cells for the preparation of a composition or a medicament for use in therapy as described hereinbefore, preferably cancer or gene therapy.

The invention further provides a method of treatment or prophylaxis of a patient comprising administering to said patient cells or compositions of the present invention, i.e. a method comprising the steps of introducing a molecule into a cell as described hereinbefore and administering said cell thus prepared to said patient. Preferably said methods are used to treat cancer or in gene therapy (or for vaccination as described hereinafter).

In vivo, any mode of administration common or standard in the art may be used, e.g. injection, infusion, topical administration, transdermal administration, both to internal and external body surfaces etc. For in vivo use, the invention can be used in relation to any tissue which contains cells to which the photosensitising agent containing compound or the molecule to be internalized is localized, including body fluid locations, as well as solid tissues. All tissues can be treated as long as the photosensitiser is taken up by the target cells, and the light can be properly delivered.

Thus, the compositions of the invention may be formulated in any convenient manner according to techniques and procedures known in the pharmaceutical art, e.g. using one or more pharmaceutically acceptable diluents, carriers or excipients. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule, purpose of treatment, age of patient, mode of administration etc. In connection with the photosensitizing agent the potency/ability to disrupt membranes on irradiation, should also be taken into account.

A further use of the compounds and compositions of the present invention is in vaccination protocols, as PCI methods can be used to present or express antigens on the surface of a cell. Thus, following transport and release of a molecule to be internalised into the cell cytosol by PCI, it may be transported to the surface where it may be presented on the outside of the cell, i.e. on the cell surface. This method has particular utility in the field of vaccination, where vaccine components i.e. antigens or immunogens may be introduced into a cell for presentation on the surface in order to induce, facilitate or augment an immune response.

The present invention thus provides a method of expressing an antigenic molecule (e.g. an antigen) or part thereof on the surface of a cell, preferably an antigen-presenting cell, said method comprising introducing a molecule into the cell cytosol by PCI using the compounds and methods as described herein, wherein said molecule, or part thereof, is subsequently presented on the surface of said cell.

Alternatively expressed, the present invention provides a method of expressing an antigenic molecule or a part thereof on the surface of a cell, comprising contacting said cell with said antigenic molecule and a compound as defined herein, and irradiating the cell with light of a wavelength effective to activate the photosensitising agent of the compound, wherein said antigenic molecule is released into the cytosol of the cell and the antigenic molecule or a part thereof of sufficient size to stimulate an immune response is presented on the cell's surface.

As used herein "expressing" refers to the presence of the antigenic molecule or a part thereof on the surface of said cell such that at least a portion of that molecule is exposed and accessible to the environment surrounding the cell. Expression on the "surface" may be achieved in which the molecule to be expressed is in contact with the cell membrane and/or components which may be present or caused to be present in that membrane.

Such antigenic presentation may advantageously result in the stimulation of an immune response, preferably an immune response which confers protection against subsequent challenge by an entity comprising or containing said antigenic molecule or part thereof, and consequently the invention finds particular utility as a method of vaccination.

More particularly, this aspect of the invention provides a method of expressing an antigenic molecule or a part thereof on the surface of a cell, said method comprising:

contacting said cell with said antigenic molecule and with a compound of the present invention, wherein said molecule and said compound are each taken up into an intracellular membrane-restricted compartment of said cell; and irradiating said cell with light of a wavelength effective to activate the photosensitizing agent of the compound, such that the membrane of said intracellular compartment is disrupted, releasing said molecule into the cytosol of the cell, without killing the cell, wherein, said released antigenic molecule, or a part thereof, is subsequently presented on the surface of said cell.

As used herein, a "disrupted" compartment refers to destruction of the integrity of the membrane of that compartment either permanently or temporarily, sufficient to allow release of the antigenic molecule contained within it.

Alternatively viewed, this aspect of the invention also provides a compound or composition for use in expressing an antigenic molecule or a part thereof on the surface of a cell, e.g. to treat or prevent a disease, disorder or infection in a subject, preferably to generate or stimulate an immune response, preferably a method of vaccination. Said composition preferably comprises an antigenic molecule and a compound of the present invention. Preferably said composition is pharmaceutically acceptable and contains also a pharmaceutically acceptable excipient, carrier or diluent as described hereinbefore. Preferably said treatment or prevention is achieved using a method described herein.

In a further aspect, the invention also provides the use of an antigenic molecule and/or a compound of the present invention agent in the preparation of a medicament for use in expressing said antigenic molecule or a part thereof on the surface of a cell, e.g. to treat or prevent a disease, disorder or infection in a subject, preferably to generate or stimulate an immune response, preferably a method of vaccination. Preferably said treatment or prevention is achieved using a method described herein. A corresponding method of treatment or prevention by administration of said antigenic molecule and compound of the present invention is also provided.

A still further aspect of the invention provides a product comprising an antigenic molecule and a compound of the present invention as a combined preparation for simultaneous, separate or sequential use in expressing said antigenic molecule or a part thereof on the surface of a cell, e.g. to treat or prevent a disease, disorder or infection in a subject, preferably to stimulate an immune response.

A yet further aspect of the invention provides a kit for use in expressing an antigenic molecule or a part thereof on the surface of a cell, said kit comprising a first container containing said antigenic molecule; and
a second container containing a compound of the present invention.

In the invention, the antigenic molecule may be any molecule wherein that molecule or a part thereof is capable of stimulating an immune response, when presented to the immune system in an appropriate manner. Advantageously, therefore the antigenic molecule will be a vaccine antigen or vaccine component, such as a polypeptide containing entity.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) i.e. whole cell vaccines, in addition sub-unit vaccines, i.e. vaccines based on particular antigenic components of organisms e.g. proteins or peptides, or even carbohydrates, have been widely investigated and reported in the literature. Any such "sub-unit"-based vaccine component may be used as the antigenic molecule according to the present invention.

However, the invention finds particular utility in the field of peptide vaccines. Thus, a preferred antigenic molecule according to the invention is a peptide (which is defined herein to include peptides of both shorter and longer lengths i.e. peptides, oligopeptides or polypeptides, and also protein molecules or fragments thereof e.g. peptides of 5-500 e.g. 10 to 250 such as 15 to 75, or 8 to 25 amino acids). Parts of antigenic molecules which are presented or expressed preferably comprise parts which are generated by antigen-processing machinery within the cell. Parts may however be generated by other means which may be achieved through appropriate antigen design (e.g. pH sensitive bands) or through other cell processing means. Conveniently such parts are of sufficient size to generate an immune response, e.g. in the case of peptides greater than 5, e.g. greater than 10 or 20 amino acids in size.

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., Asian Pac. J. Allergy. Immunol. 1997, 15(1), 41-8; Naruse, Hokkaido Igaku Zasshi 1994, 69(4), 811-20; Casal et al., J. Virol., 1995, 69(11), 7274-7; Belyakov et al., Proc. Natl. Acad. Sci. USA, 1998, 95(4), 1709-14; Naruse et al., Proc. Natl. Sci. USA, 1994 91(20), 9588-92; Kabeya et al., Vaccine 1996, 14(12), 1118-22; Itoh et al., Proc. Natl. Acad. Sci. USA, 1986, 83(23) 9174-8.

Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting as antigens in the simulation of cytotoxic T-lymphocytes. (Schirrmacher, Journal of Cancer Research and Clinical Oncology 1995, 121, 443-451; Curtis Cancer Chemotherapy and Biological Response Modifiers, 1997, 17, 316-327). A synthetic peptide vaccine has also been evaluated for the treatment of metastatic melanoma (Rosenberg et al., Nat. Med. 1998, 4(3), 321-7). A T-cell receptor peptide vaccine for the treatment of multiple sclerosis is described in Wilson et al., J. Neuroimmunol. 1997, 76(1-2), 15-28. Any such peptide vaccine component may be used as the antigenic molecule of the invention, as indeed may any of the peptides described or proposed as peptide vaccines in the literature. The peptide may thus be synthetic or isolated or otherwise derived from an organism.

The cell which is subjected to the methods, uses etc. of the invention may be any cell which is capable of expressing, or presenting on its surface a molecule which is administered or transported into its cytosol.

The cell is conveniently an immune effector cell i.e. a cell involved in the immune response. However, other cells may also present antigen to the immune system and these also fall within the scope of the invention. The cells according to the present invention are thus advantageously antigen-presenting cells. The antigen-presenting cell may be involved in any aspect or "arm" of the immune response, including both humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them.

The stimulation of cytotoxic cells or antibody-producing cells, requires antigens to be presented to the cell to be stimulated in a particular manner by the antigen-presenting cells, for example MHC Class I presentation (e.g. activation of $CD8^+$ cytotoxic T-cells requires MHC-1 antigen presentation).

Antigen-presenting cells are known in the art and described in the literature and include for example, lymphocytes (both T and B cells), dendritic cells, macrophages etc. Others include for example cancer cells e.g. melanoma cells.

For antigen presentation by an antigen-presenting cell to a cytotoxic T-cell (CTL) the antigenic molecule needs to enter the cytosol of the antigen-presenting cell (Germain, Cell, 1994, 76, 287-299). The present invention provides an efficient means of delivery of the antigenic molecule into the cytosol.

Once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the antigenic molecule expressed or presented on the surface of the cell according to the present invention may be a part or fragment of the antigenic molecule which is internalised (endocytosed).

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded, e.g. by proteasomes and transported into endoplasmic reticulum by means of TAP (transporter associated with antigen presentation) where the peptides may bind to MHC class I molecules and be transported to the cell surface (Yewdell and Bennink, 1992, Adv. Immunol. 52: 1-123). If the peptide is of foreign antigen origin, the peptide-MHC class I complex will be recognised by CD8+ cytotoxic T-cells (CTLs). The CTLs will bind to the peptide-MHC (HLA) class I complex and thereby be activated, start to proliferate and form a clone of CTLs. The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, 1996, Immunology Today 17: 131-137). This is the basis for development of inter alia cancer vaccines.

One of the largest practical problems is to introduce sufficient amounts of antigens (or parts of the antigen) into the cytosol. This may be solved according to the present invention.

These methods may be used in vitro or in vivo, as described hereinbefore.

Thus, a further aspect of the invention provides an antigen-presenting cell expressing an antigenic molecule, or a part thereof, on its surface, which cell is obtainable (or obtained) by a method as hereinbefore defined. Other aspects of the invention provide a population or culture of such cells, especially a viable and functionally intact population or culture of such cells, and also the use of such a cell (or population or culture of cells) in therapy, particularly for stimulating an immune response, and especially for stimulating CTLs.

Also provided is the use of such a cell (or population or culture of cells) for the preparation of a medicament (e.g. a vaccine composition) for stimulating an immune response, and especially for stimulating CTLs.

The invention will now be described in more detail in the following non-limiting Examples with reference to the following drawings in which:

FIG. 1 shows particularly preferred compounds of the present invention (TPC=tetraphenylchlorin).

FIG. 2 shows Scheme 1: synthetic route for synthesis of compound 5. Reagents and conditions: (a) propionic acid, reflux, 1 h (20%); (b) NaNO$_2$ (1.8 eq), TFA, rt, 3 min. 67%); (c) SnCl$_2$.2H$_2$O, conc. HCl, 60° C., 1 h (88%); (d) Bromoacetyl bromide, Et$_3$N, CH$_2$Cl$_2$, rt, 1 h (64%) (e) Piperazine, CH$_2$Cl$_2$, rt, 1 h (94%).

FIG. 3 shows Scheme 2. Synthesis of N-modified Chitosan derivatives (TPP—CS-TMA & TPP—CS-MP). Here A-represents 1$^{st}$ batch compounds and B-presents 2$^{nd}$ batch compounds. Reagents and conditions: (a) MeSO$_3$H/H$_2$O, 10° C.-rt, 1 h, (90%); (b) TBDMSCI, imidazole, DMSO, rt, 24 h (96%); (c) Bromoacetyl bromide, Et$_3$N, CH$_2$Cl$_2$, −20° C., 1 h (92%); (d) compound 5 i.e. TPP—NH-Pip (0.1 or 0.25 eq), Et$_3$N, CHCl$_3$, rt, 2 h (92-90%) (e) NMe$_3$ or 1-methyl piperazine, CHCl$_3$, rt, 24 h (f) TBAF, NMP, 55° C., 24 h or conc. HCl/MeOH, rt, 24 h.

Figure 8:
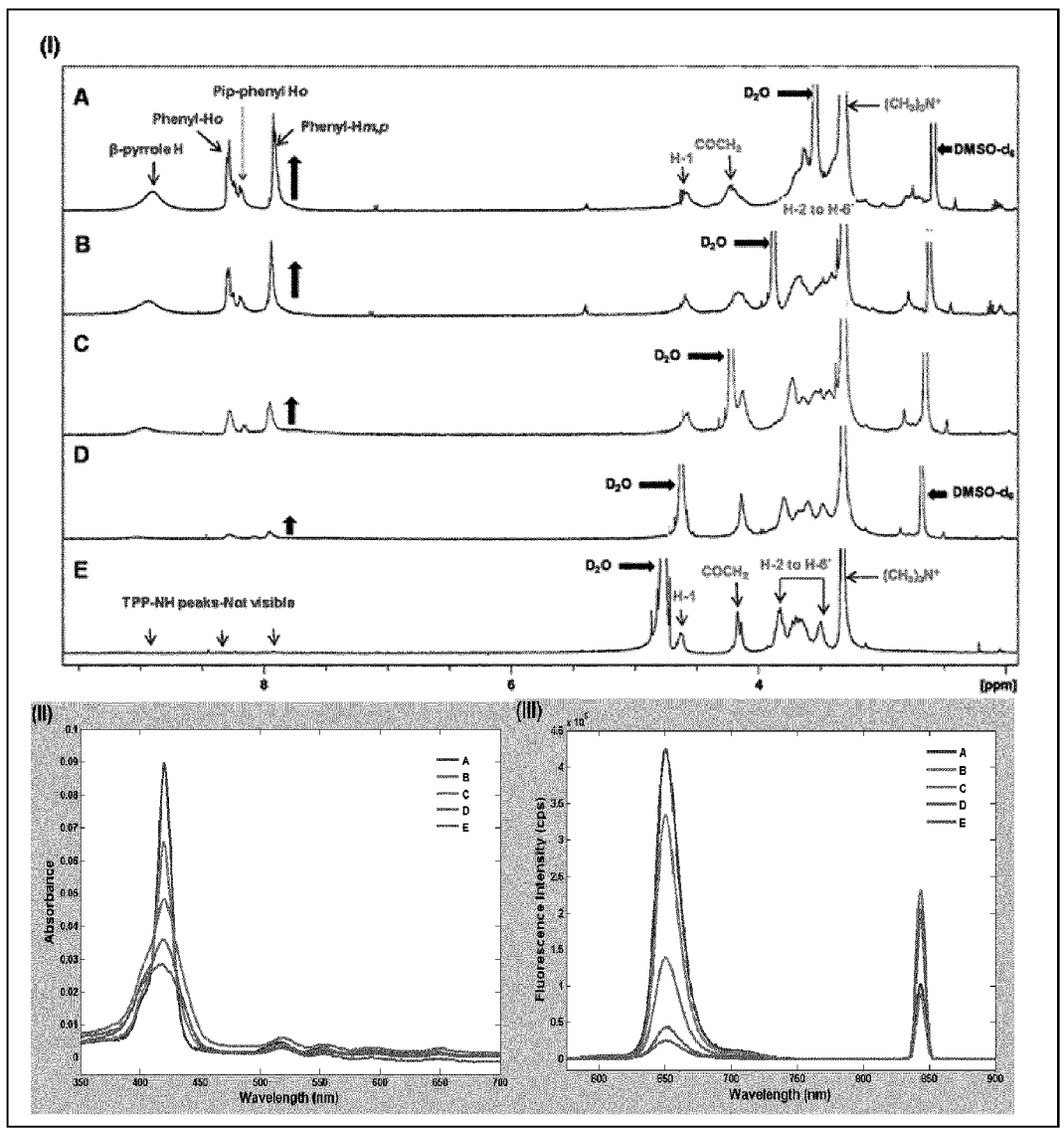

FIG. 8 shows I) $^1$H NMR spectra of TPPp$_{0.25}$-CS-TMA$_{0.75}$ 17B in solvents: (A) DMSO-d$_6$: D$_2$O (98:2); (B) DMSO-d$_6$: D$_2$O (75:25); (C) DMSO-d$_6$: D$_2$O (50:50); (D) DMSO-d$_6$: D$_2$O (25:75); (E) DMSO-d$_6$: D$_2$O (0:100); (II) UV-vis. Absorption Spectra overlay of TPPp$_{0.25}$-CS-TMA$_{0.75}$ 17B at constant concentration (0.3 mg/L) in co-solvents: (A) DMSO: H$_2$O (100:0); (B) DMSO: H$_2$O (75:25); (C) DMSO: H$_2$O (50:50); (D) DMSO: H$_2$O (25:75); (E) DMSO: H$_2$O (0:100); (III) Fluorescence Emission Spectra overlay of TPPp$_{0.25}$-CS-TMA$_{0.75}$ 17B at constant absorbance (0.85-0.90; data not shown) and when excited at 419 nm (3-3 slit) in co-solvents: (A) DMSO: H$_2$O (100:0); (B) DMSO: H$_2$O (75:25); (C) DMSO: H$_2$O (50:50); (D) DMSO: H$_2$O (25:75); (E) DMSO: H$_2$O (0:100).

Figure 9:
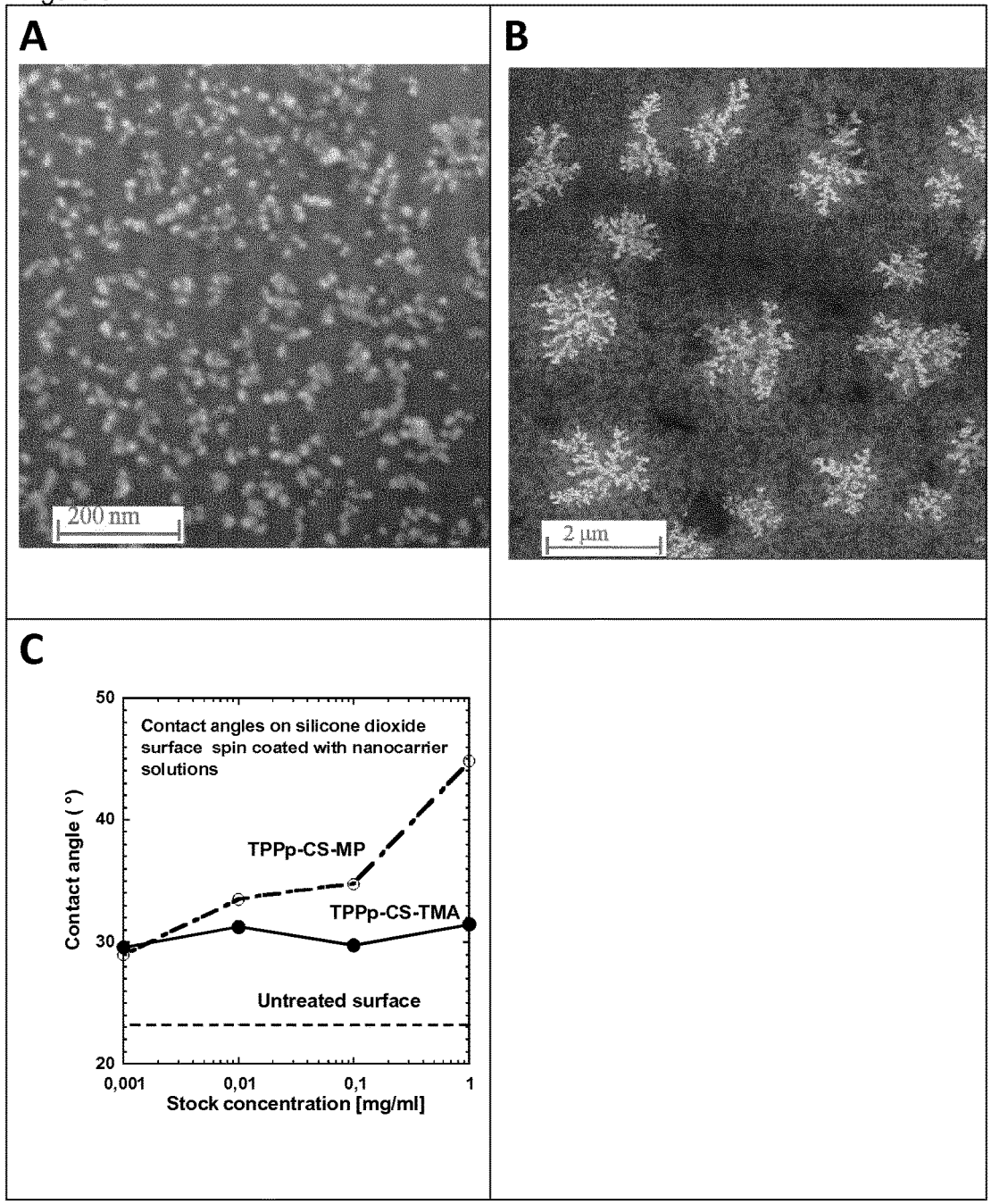

FIG. 9 shows (A) SEM image of TPP—CS-TMA isolated nanoparticles (B) SEM image of TPP—CS-TMA dendratic nanoaggregates (C) Graph of the contact angles of TPP—CS derivatives.

Figure 10:
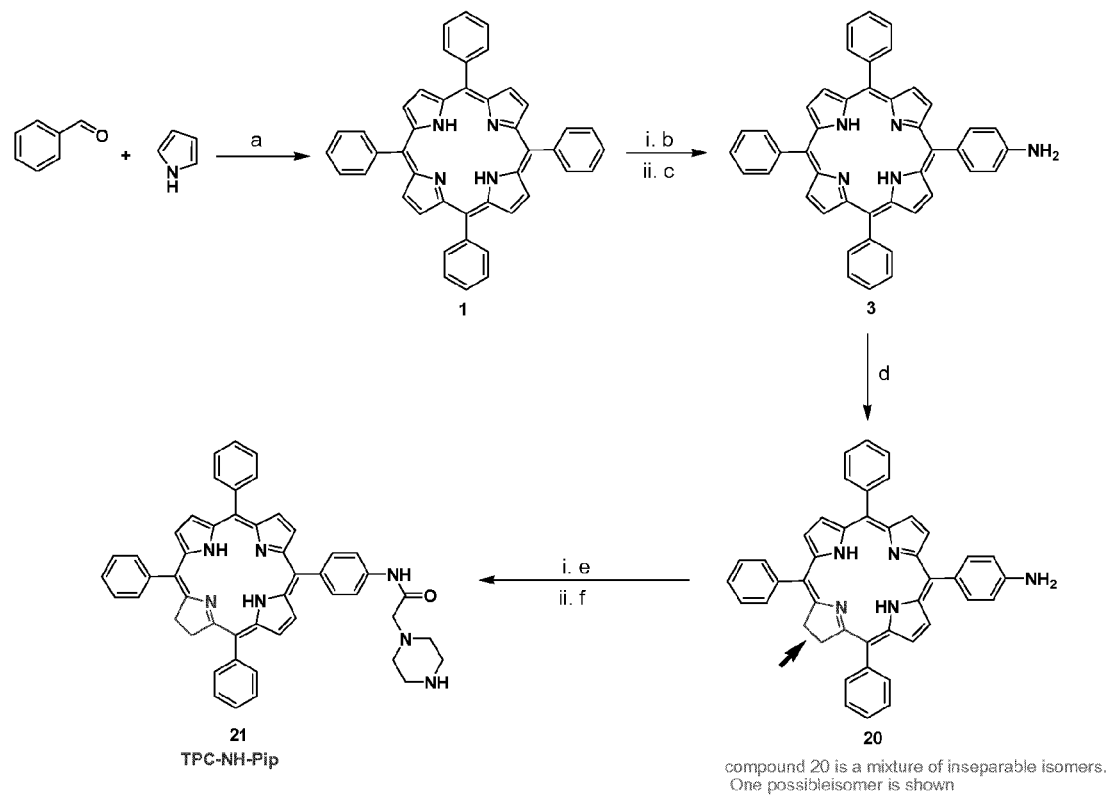

FIG. 10 shows Scheme 3—Synthesis scheme for compounds 1, 3 20 and 21. Reactions and conditions: ((a) Propionic acid, reflux, 1 h, (20%); (b) NaNO$_2$ (1.8 eq.), TFA, rt, 3 min.; (c) SnCl$_2$.2H$_2$O, conc. HCl, 60° C., 1 h, (54%); (d$_1$) p-Toluenesulfonylhydrazide, K$_2$CO$_3$, pyridine, reflux, 24 h; (d$_2$) o-Chloranil, CH$_2$Cl$_2$, rt, (80%); (e) Chloroacetyl chloride, Et$_3$N, CH$_2$Cl$_2$, rt, 2 h, in situ-(f) Piperazine, CH$_2$Cl$_2$, rt, 12 h, (61%). All derivatives of compound 20 and 21 will contain the TPCa$_1$ and the TPCa$_2$ isomer. However only the TPCa$_1$ structure is shown in schemes and in the structure drawings.

Figure 11:
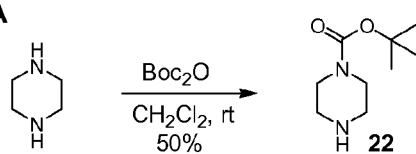
Figure 11:
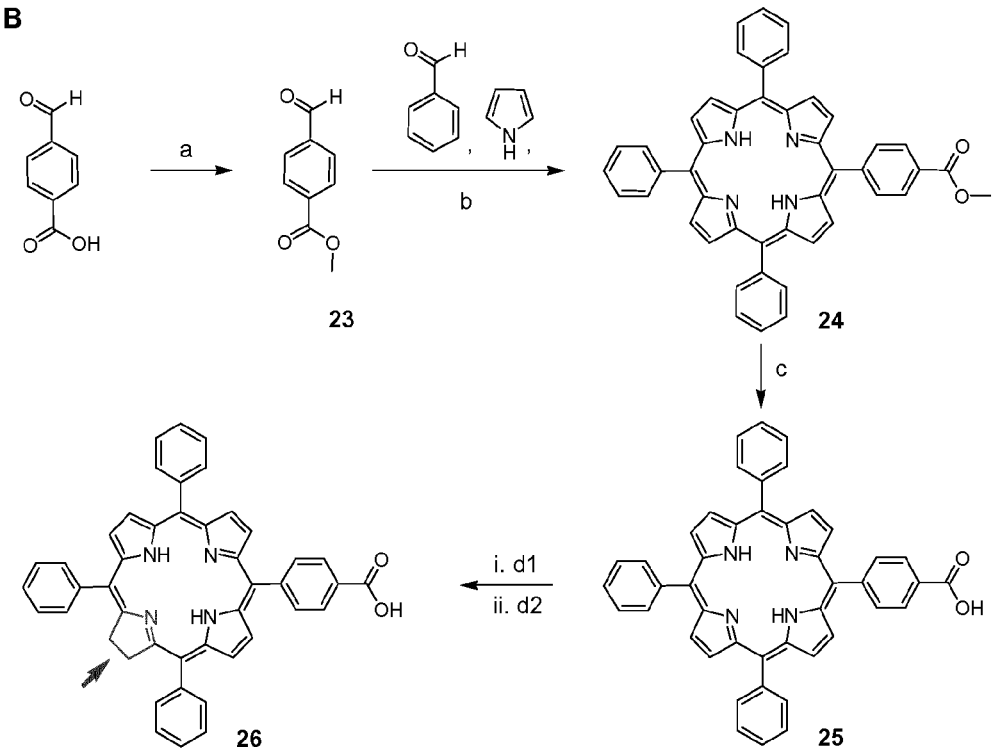
Figure 11:
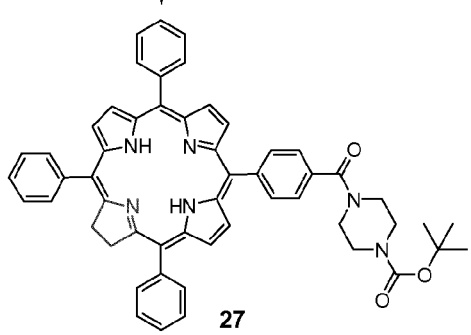
Figure 11:
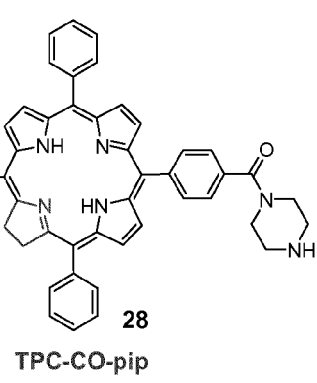

FIG. 11 shows Scheme 4—synthesis scheme for compounds 22-28. Reactions and conditions: (a) Acetyl chloride, MeOH, reflux, 24 h, (87%); (b) BF$_3$.Et$_2$O, CHCl$_3$, rt, p-chloranil, 48 h, (14%); (c) 2N KOH (in MeOH), THF: Pyridine (10:1), reflux, 24 h (71%); (d$_1$) p-Toluenesulfonylhydrazide, K$_2$CO$_3$, Pyridine, reflux, 24 h; (d$_2$) o-chloranil, CH$_2$Cl$_2$: MeOH (75:25), rt, (70%); (e) EDCl.HCl, HOBT, Et$_3$N,N-Boc-piperazine 5, DMF, rt, 24 h (54%) (f) TFA, CH$_2$Cl$_2$, rt, 1 h (89%). All derivatives of compound 26-28 will contain the TPCc$_1$ and the TPCc$_2$ isomer. However, only the TPCc$_1$ structure is shown in schemes and in the structure drawings.

Figure 12:
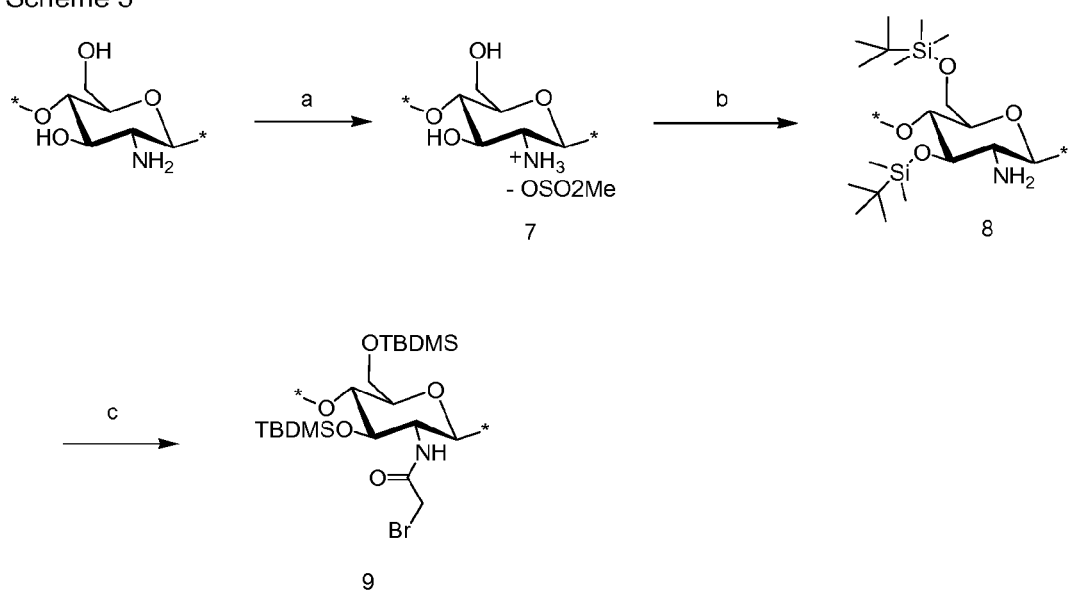

FIG. 12 shows Scheme 5—synthesis of compounds 7-9. Reagents and conditions: (a) MeSO$_3$H/H$_2$O, 10° C.-rt, 1 h, (90%); (b) TBDMSCI, imidazole, DMSO, rt, 24 h, (96%); (c) Bromoacetyl bromide, Et$_3$N, CH$_2$Cl$_2$, −20° C., 1 h, (92%).

Figure 13:
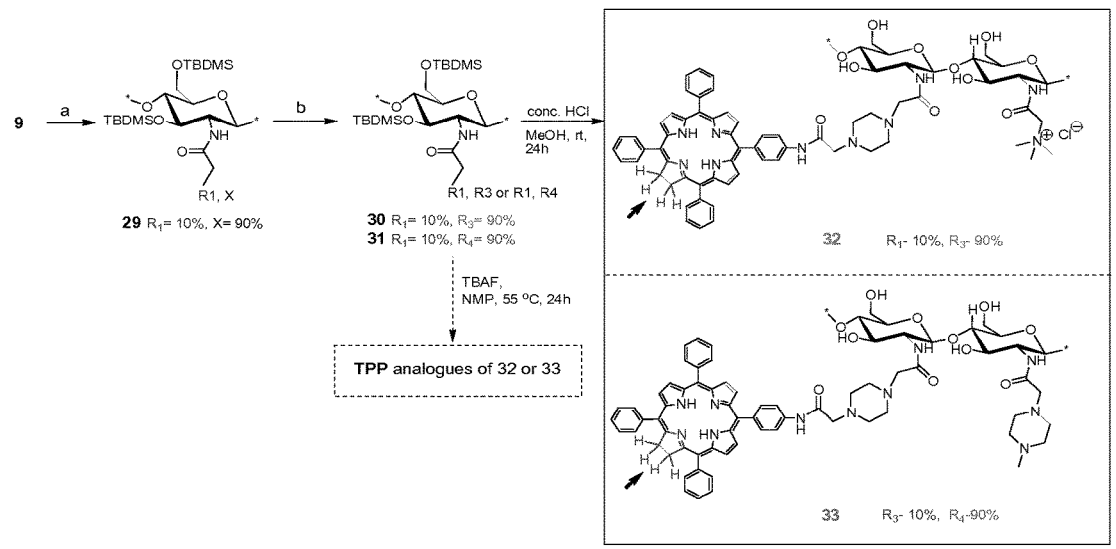
Figure 13:
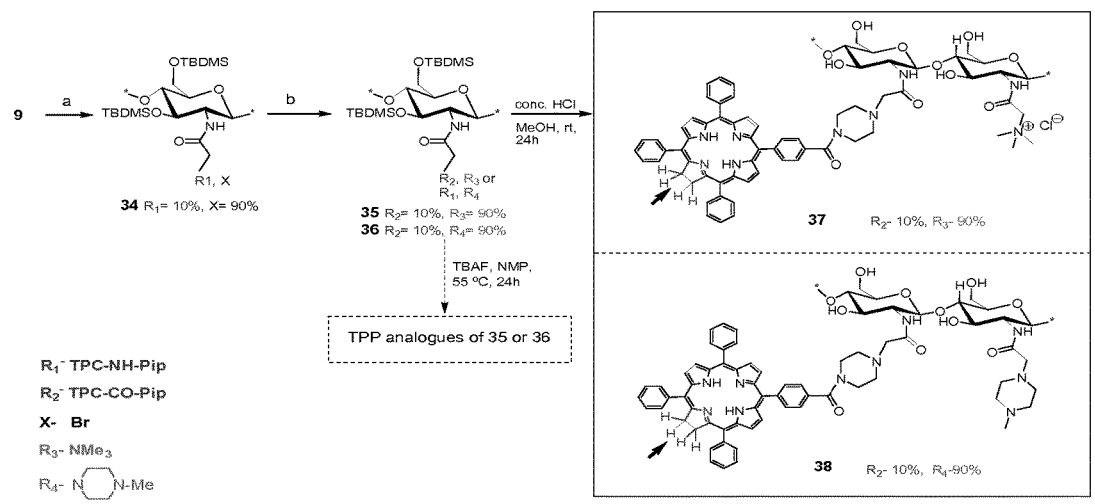

FIG. 13 shows Scheme 6A and 6B. Reagents and conditions (6A): (a) compound 21 i.e. TPC—NH-Pip (0.1 eq), Et$_3$N, CHCl$_3$, rt, 2 h (78%) (b) NMe$_3$ or 1-methyl piperazine, CHCl$_3$, rt, 24 h. Reagents and conditions (6b): a) compound 28 i.e. TPC—CO-Pip (0.1 eq), Et$_3$N, NMP, 75° C., 12 h (89%) (b) NMe$_3$ or 1-methyl piperazine, CHCl$_3$, rt, 24 h.

Figure 14:
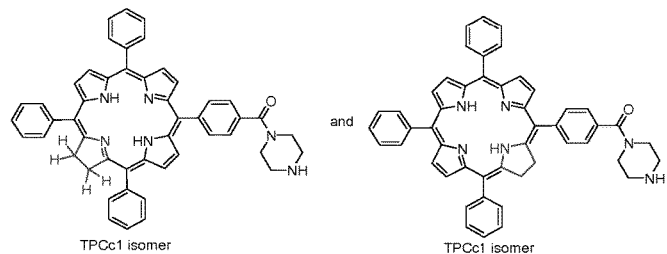
Figure 14:
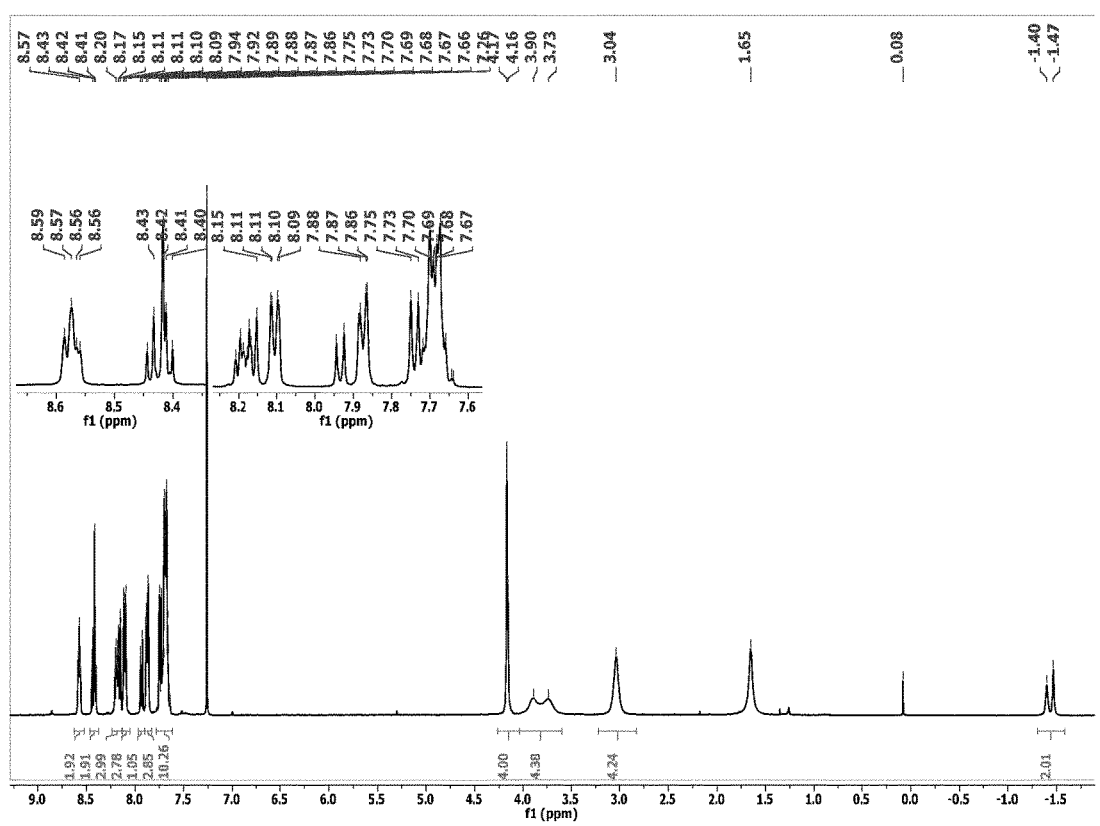

FIG. 14 shows the $^1$H NMR spectrum of TPC—CO-Pip (28) in CDCl$_3$. The two isomers are shown.

Figure 15:
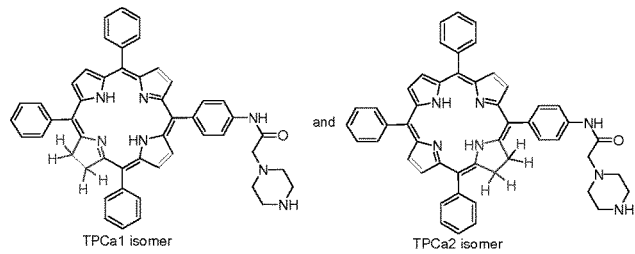
Figure 15:
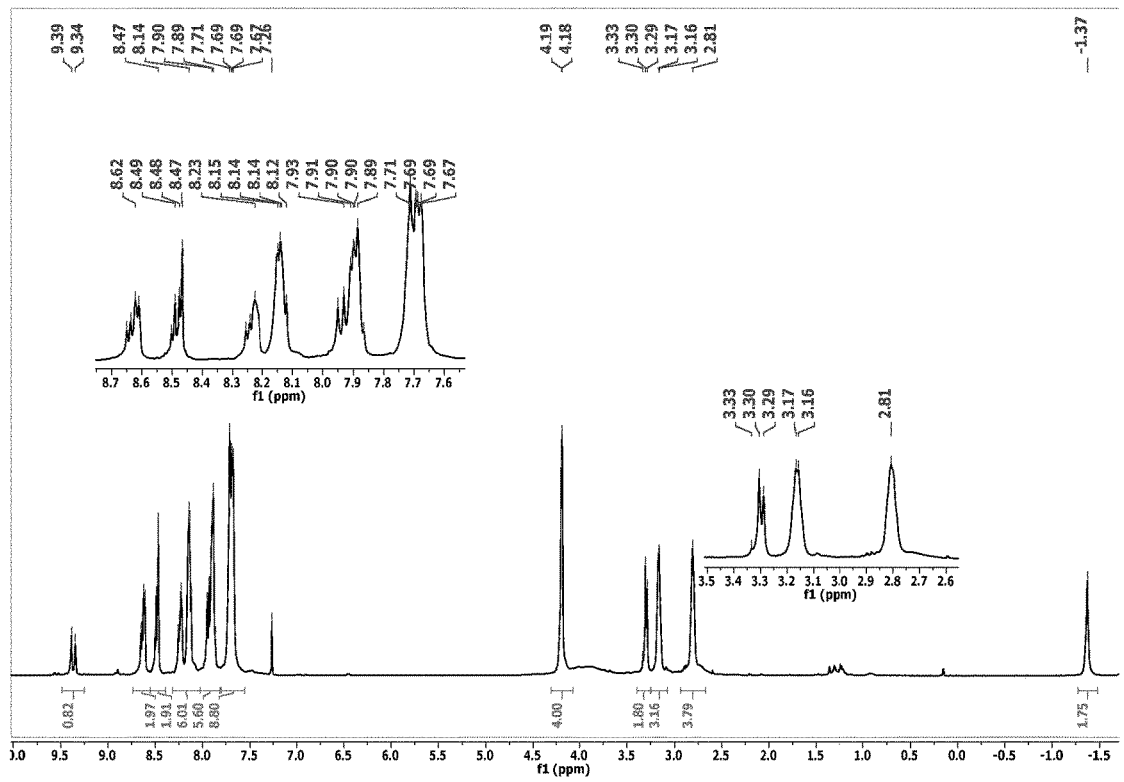

FIG. 15 shows the $^1$H NMR spectrum of compound 21 (TPC—NH-Pip) in CDCl$_3$ (The two isomers are shown).

Figure 16:
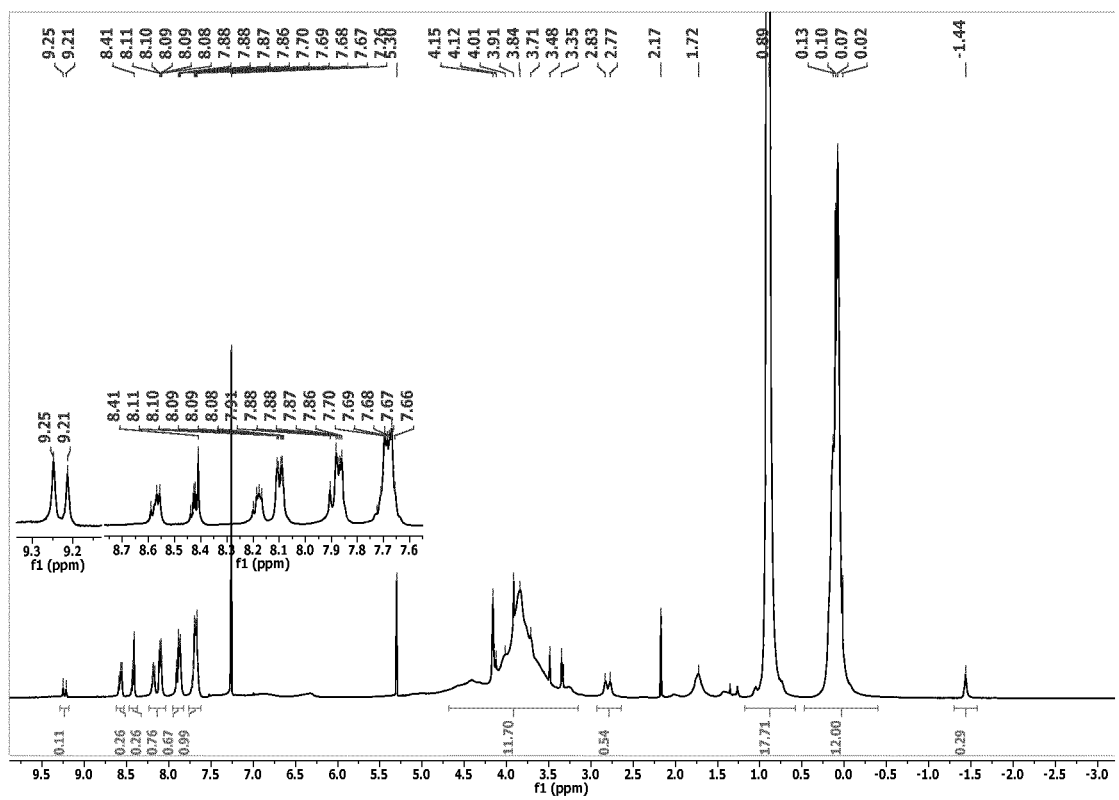

FIG. 16 shows the $^1$H NMR spectrum of compound 29 in CDCl$_3$. This compound contains the TPCa1 and the TPCa2 isomers.

Figure 17:
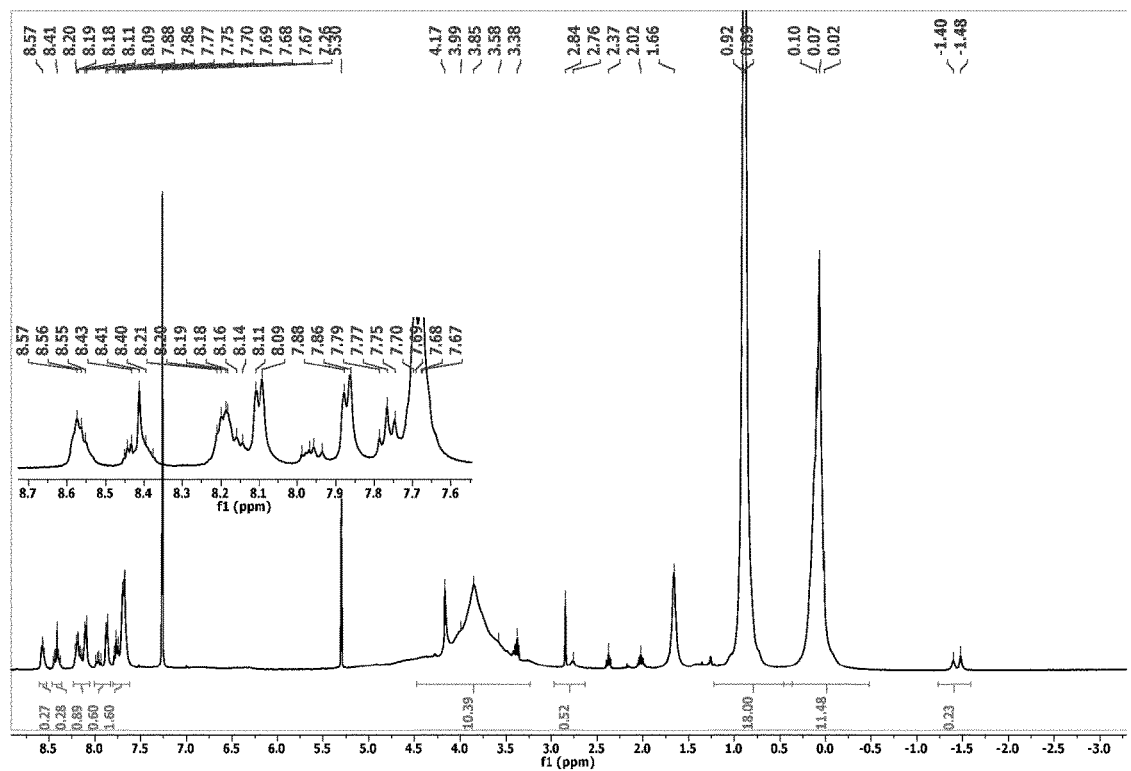

FIG. 17 shows $^1$H NMR spectrum of compound 34 in CDCl$_3$. This compound contains the TPCc1 and the TPCc2 isomers.

Figure 18:
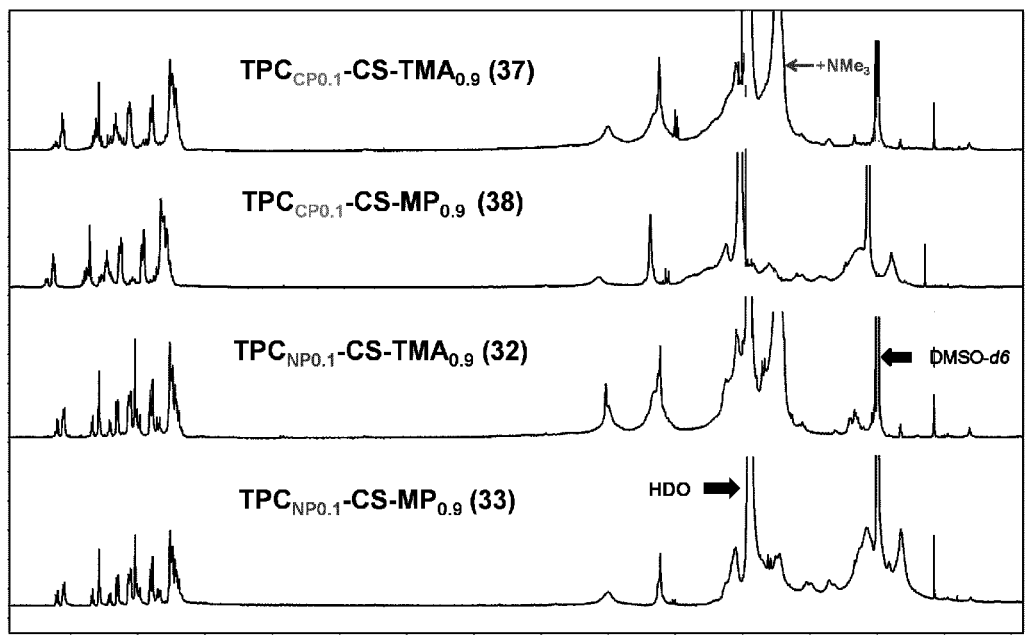

FIG. 18 shows the NMR spectra of the final carrier compounds (37, 38, 32 and 33) in d$_6$-DMSO/D$_2$O.

Figure 19:
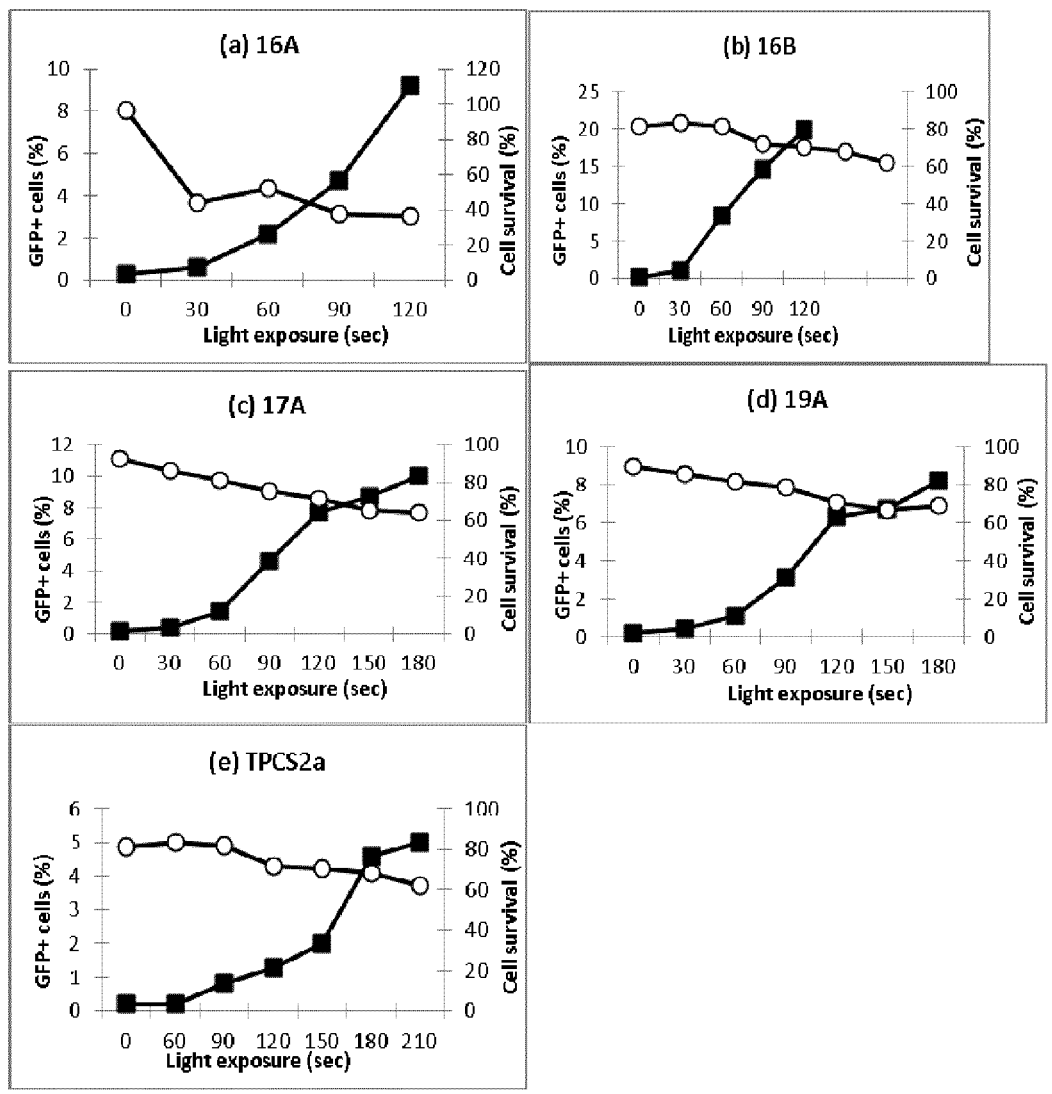

FIG. 19 shows transfection with pEGFP-N1 in HCT116/LUC cells. Transfection was measured 48 h after illumination by flow cytometry. Cell survival was measured by the MTT assay. (a) 16A. 0.1 μg/ml TPP. (b) 16B. 0.1 μg/ml TPP. (c) 17A. 0.01 μg/ml TPP. (d) 19A. 0.01 μg/ml TPP. (e) TPCS$_{2a}$. 0.1 μg/ml.

Figure 20:
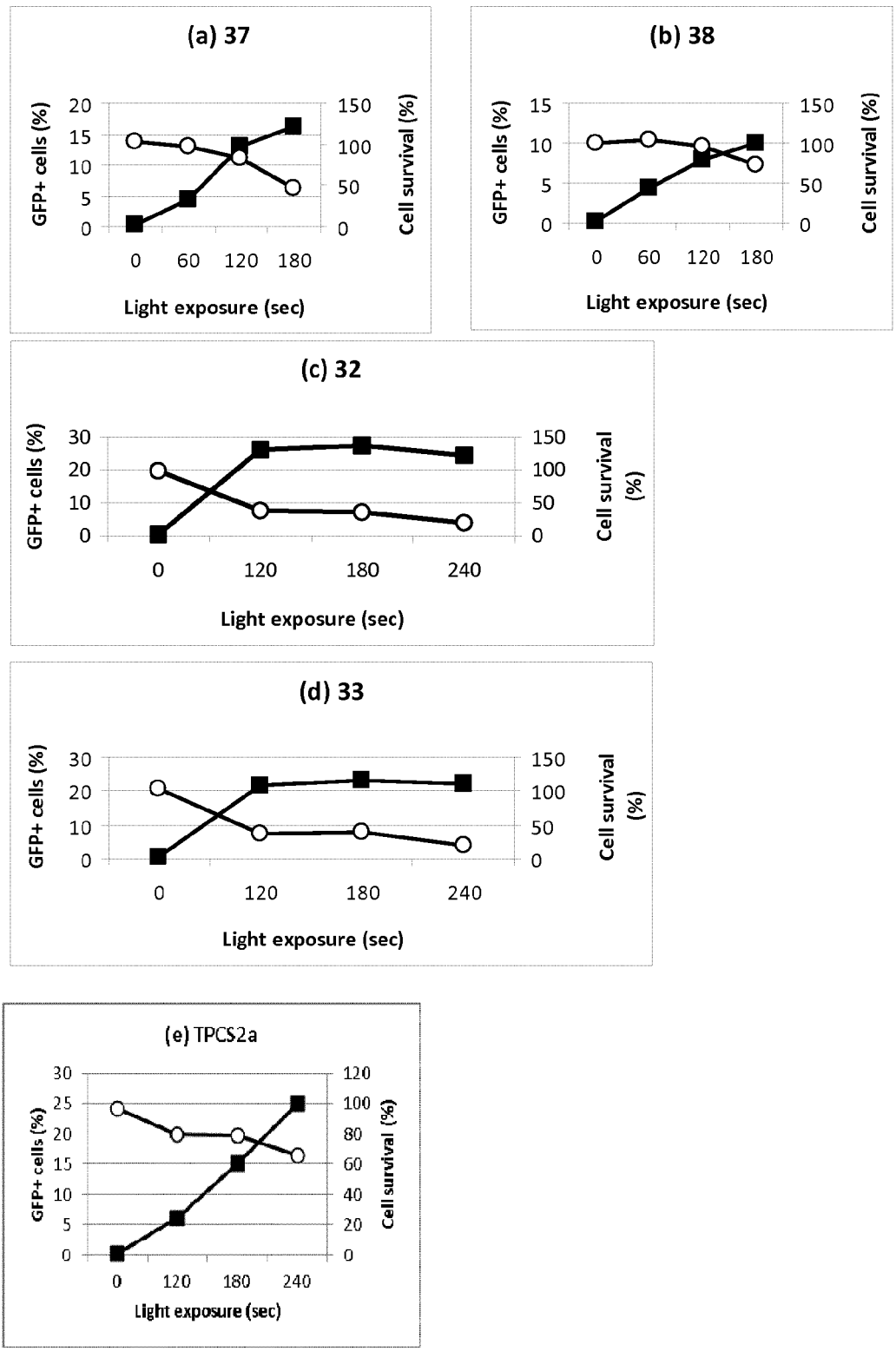

FIG. 20 shows transfection with pEGFP-N1 in HCT116/LUC cells. Transfection was measured 48 h after illumination by flow cytometry. Cell survival was measured by the MTT assay. (a) compound 37. 0.05 μg/ml TPC. (b) compound 38. 0.05 μg/ml TPC. (c) compound 32. 0.05 μg/ml TPC. (d) compound 33. 0.05 μg/ml TPC. (e) TPCS$_{2a}$. 0.1 μg/ml.

Figure 21:
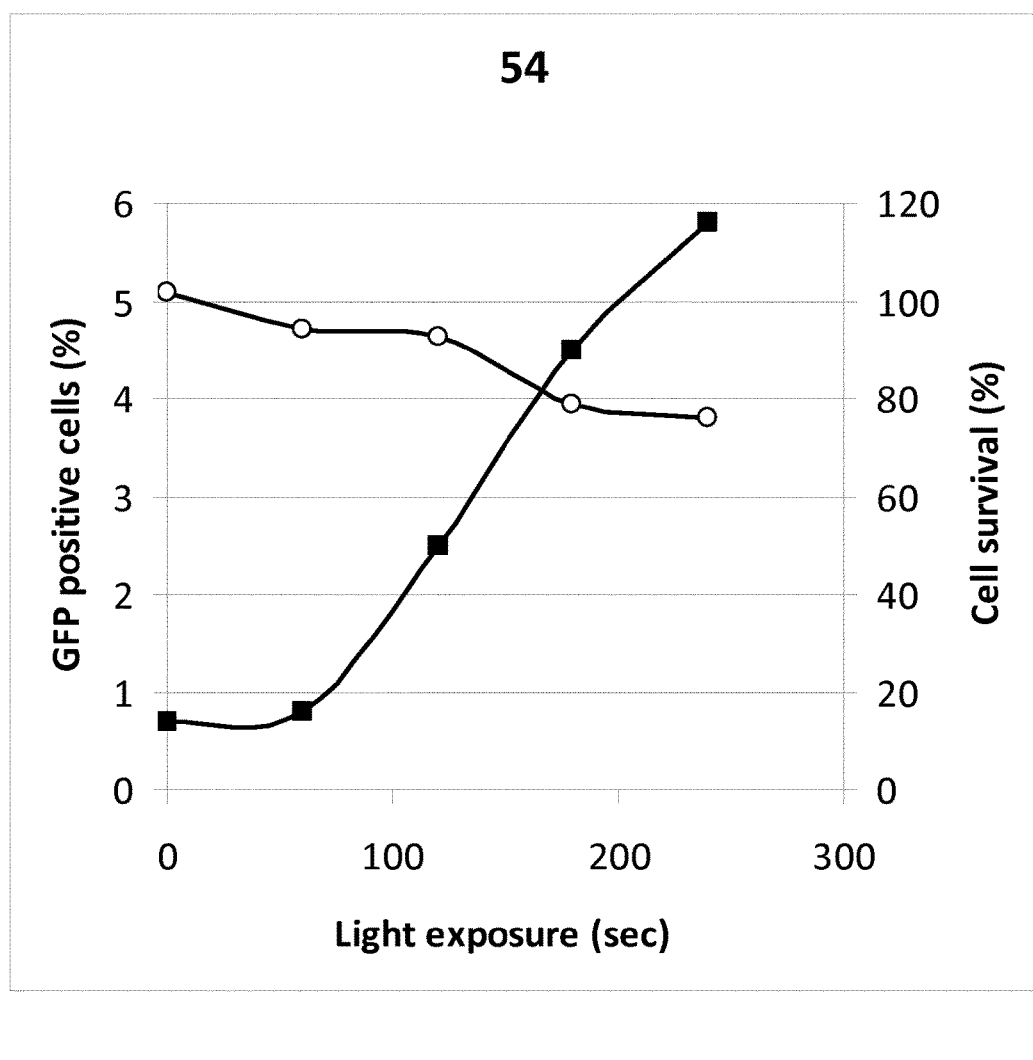

FIG. 21 shows transfection with pEGFP-N1 in HCT116/LUC cells. Transfection was measured 48 h after illumination by flow cytometry. Cell survival was measured by the MTT assay. Compound 54 was used at a concentration of 0.1 μg/ml.

Figure 22:
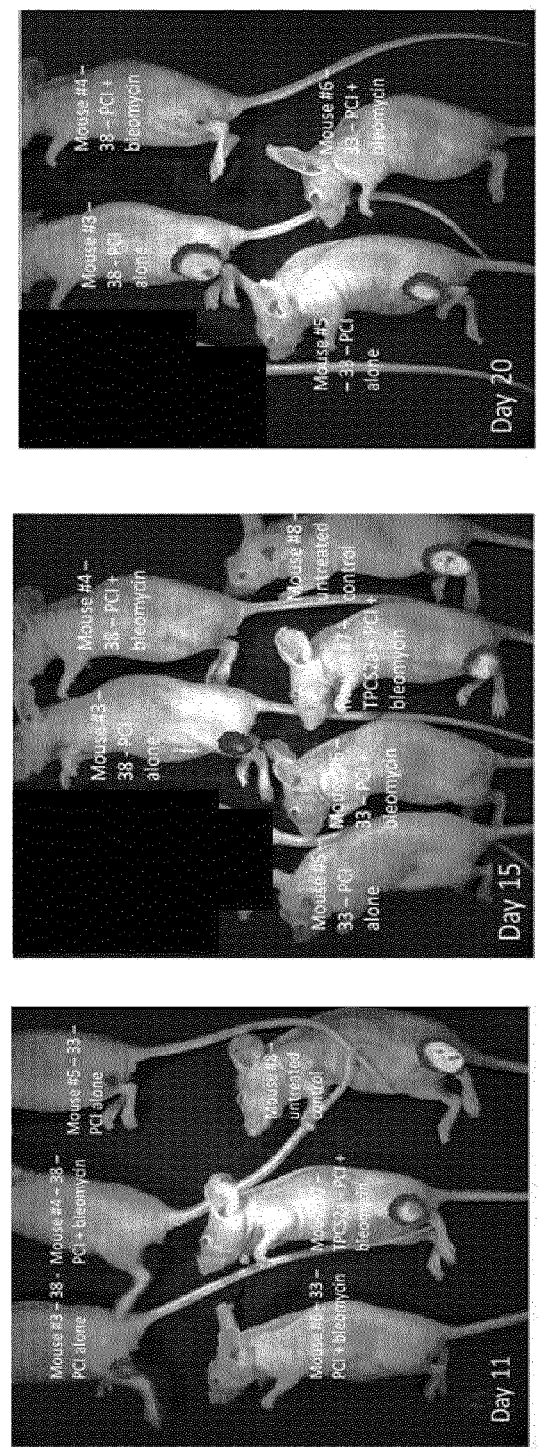

FIG. 22 shows in vivo bioluminescence imaging after PCI treatment of tumour-bearing animals with chitosan-conjugates and bleomycin. The animals were treated as described in the Materials and Methods section of Example 3. The treatment for each animal and the time point for imaging (days after photosensitiser injection) are indicated.

Figure 23:
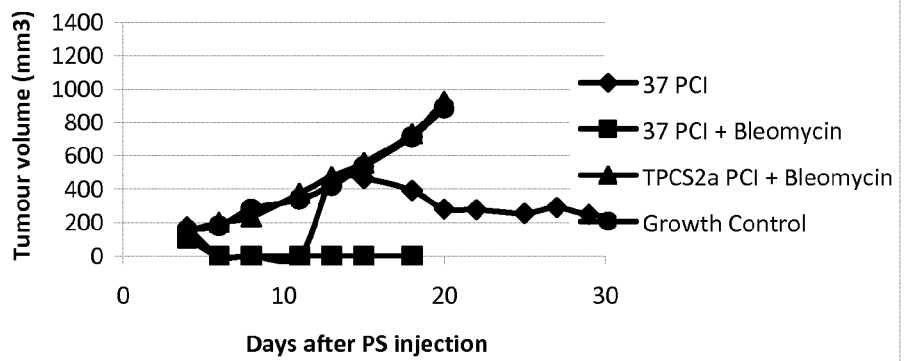
Figure 23:
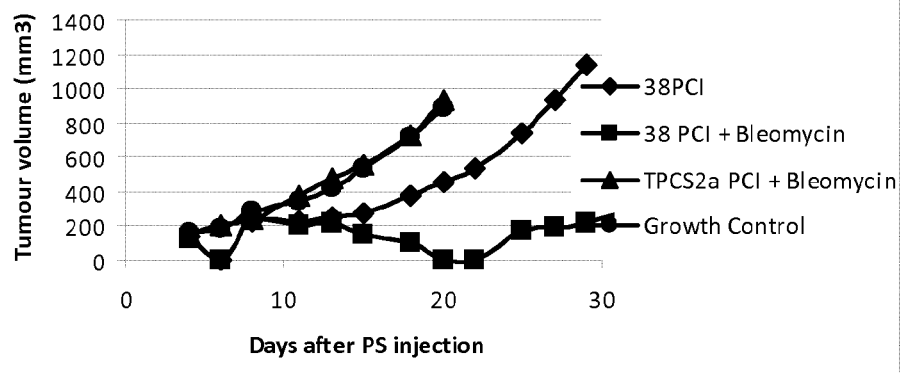
Figure 23:
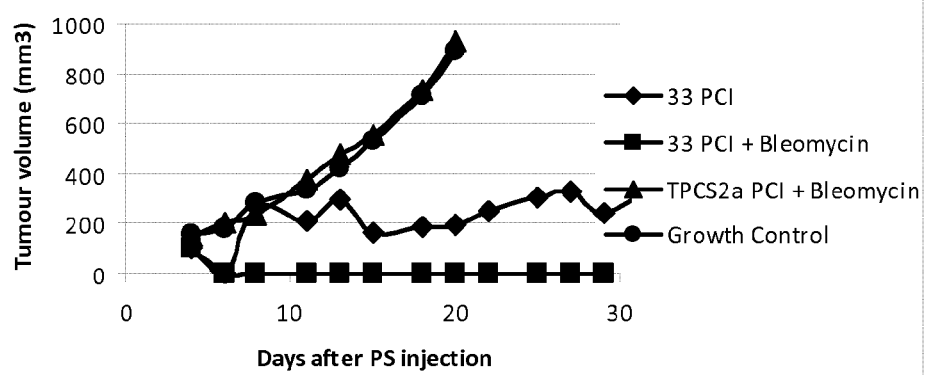

FIG. 23 shows growth of tumours after PCI treatment of tumour-bearing animals with compound 37, 38 or 33 and bleomycin. The animals were treated as described in Materials and Methods in Example 3. PS: photosensitiser.

Figure 24:
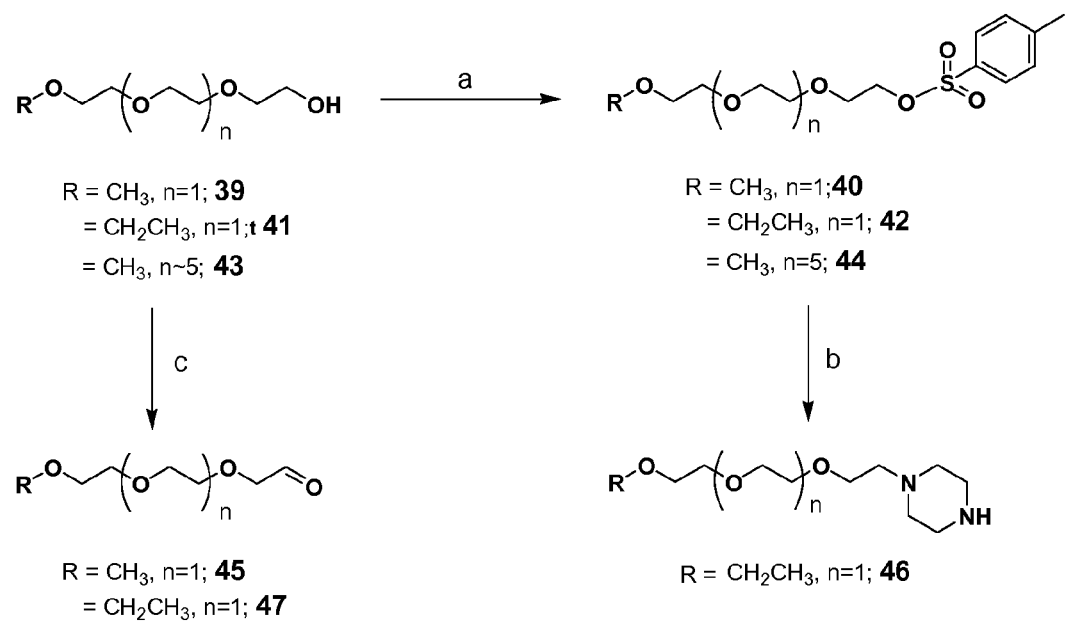

FIG. 24 shows scheme 7—the synthesis of reagents for TEGylation and PEGylation. Reaction conditions: (a) KOH, p-TsCl, THF/H$_2$O, rt, 12 h; (b) Piperazine, CH$_3$CN, rt, 12 h, (41%); (c) Swern oxidation: (COCl)$_2$, CH$_2$Cl$_2$, DMSO, Et$_3$N, −78° C.

Figure 25:
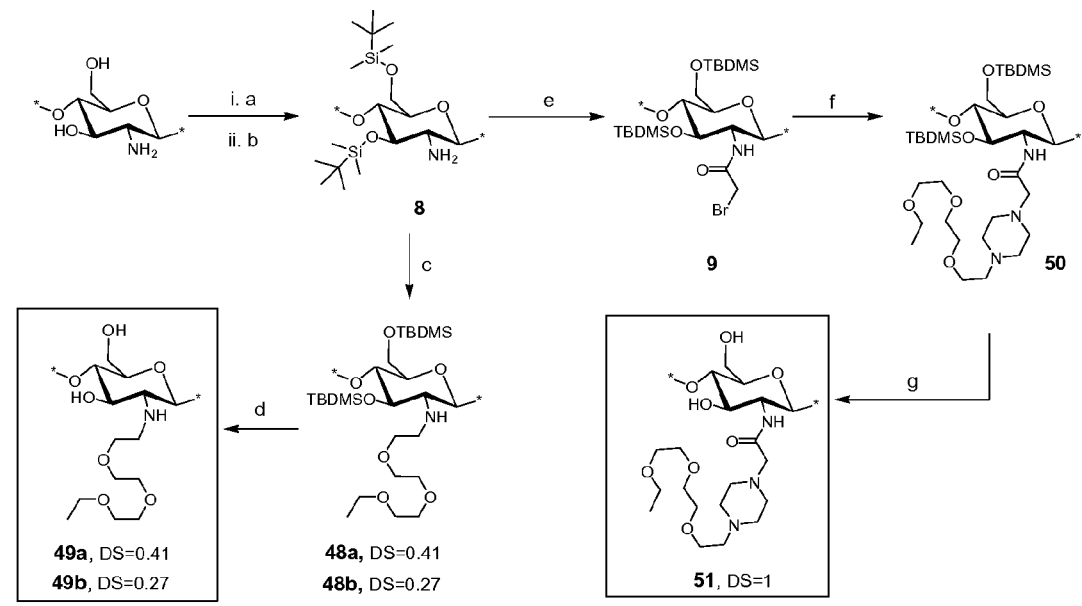

FIG. 25 shows scheme 8—TEGylations of DiTBDMS-Chitosan. Reagents and conditions: (a) MeSO$_3$H/H$_2$O, 10° C.-rt, 1 h, (90%); (b) TBDMSCI, imidazole, DMSO, rt, 24 h (96%); (c) TEG-OTs 42, Cs$_2$CO$_3$, NMP, KI, 50° C., 24 h; (d) HCl/MeOH (30% v/v), rt, 24 h; (e) Bromoacetyl bromide, Et$_3$N, CH$_2$Cl$_2$, −20° C., 1 h (92%), (f) TEG-Pip 46 Et$_3$N, CH$_2$Cl$_2$, rt, 24 h; (g) HCl/MeOH (30% v/v), rt, 24 h.

Figure 26:
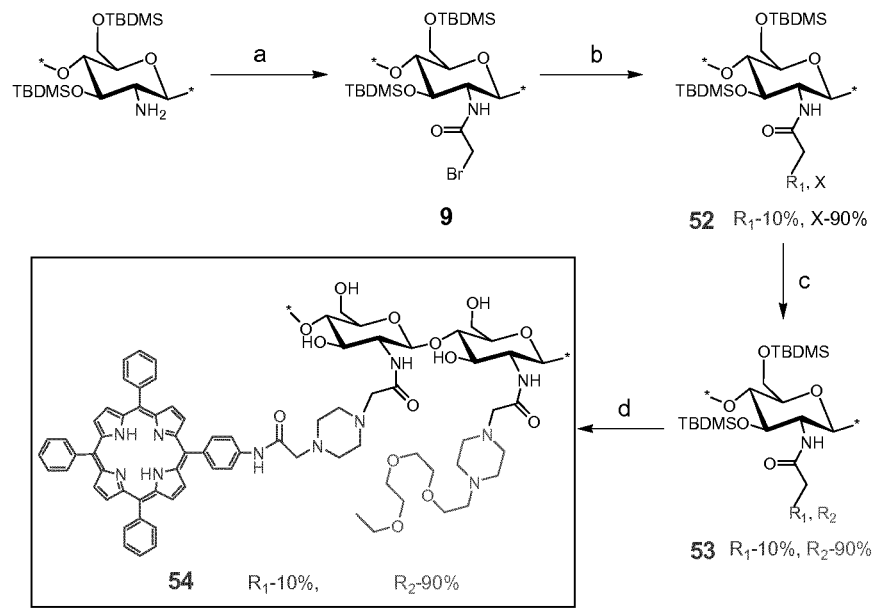
Figure 26:
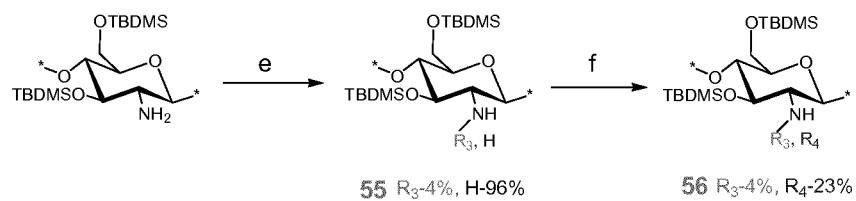
Figure 26:
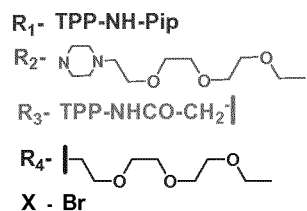
Figure 26:
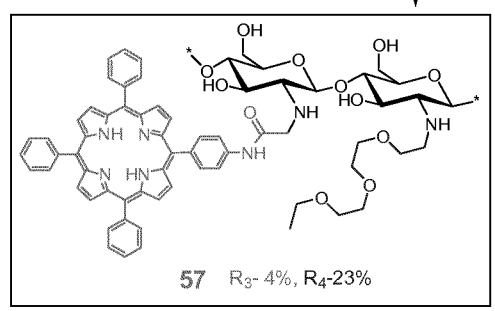

FIG. 26 shows scheme 9—the synthesis of TEGylated chitosan-TPP conjugates. Reagents and conditions: (a) Bromoacetyl bromide, Et$_3$N, CH$_2$Cl$_2$, −20° C., 1 h (92%), (b) TPP—NH-Pip 5 (0.1 eq.), CH$_2$Cl$_2$, Et$_3$N, rt, (c) TEG-PIP (compound 46) (2 eq.), CH$_2$Cl$_2$, Et$_3$N, rt, 24 h (d) 30% (v/v) HCl in MeOH, rt, 12 h; (e) Compound 4 (0.25 eq), NMP, 50° C., Cs$_2$CO$_3$, 24 h; (f) TEG-monoethylether-tosylate (compound 42), NMP, 50° C., KI, 24 h (g) 30% (v/v) HCl in MeOH, rt, 12 h.

Figure 27:
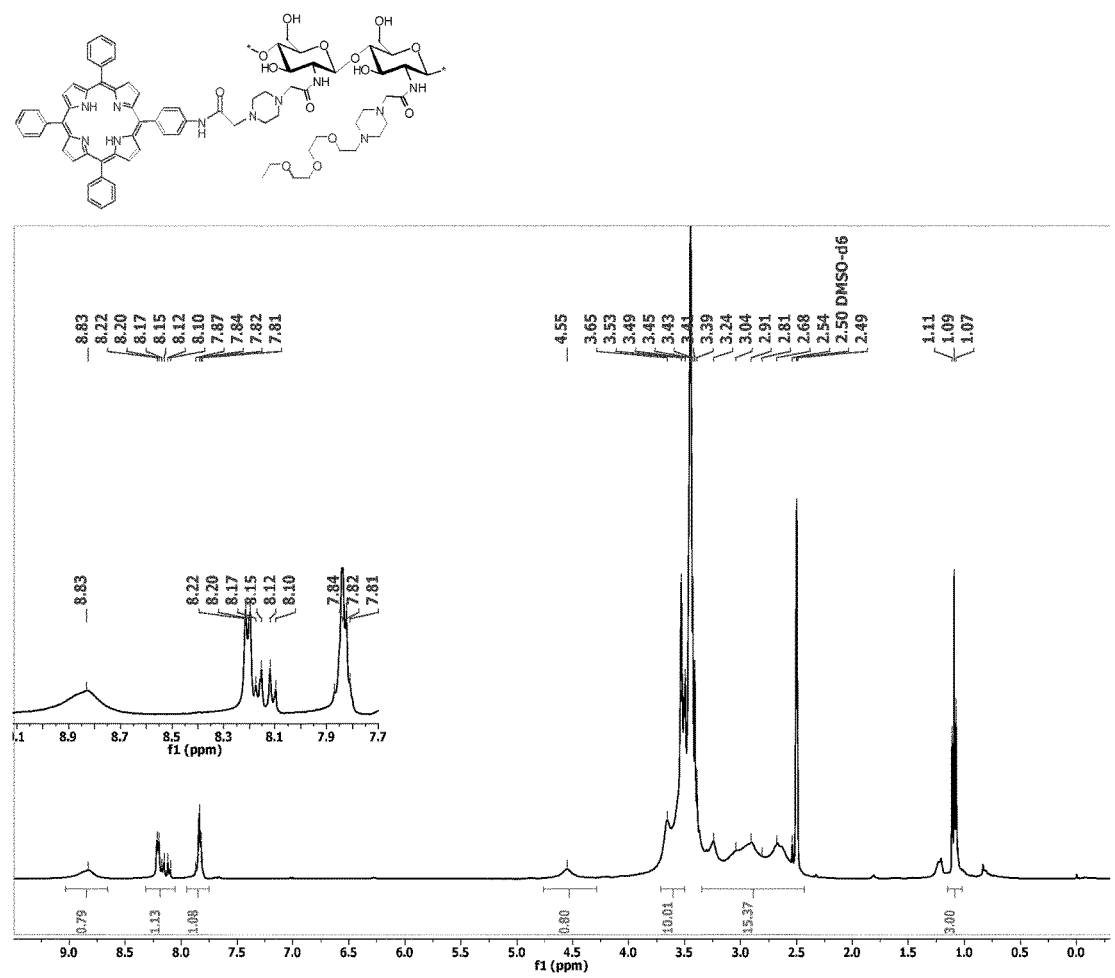

FIG. 27 shows $^1$H NMR (400 MHz, DMSO-d6: D$_2$O, 96:4) of compound 54.

Figure 28:
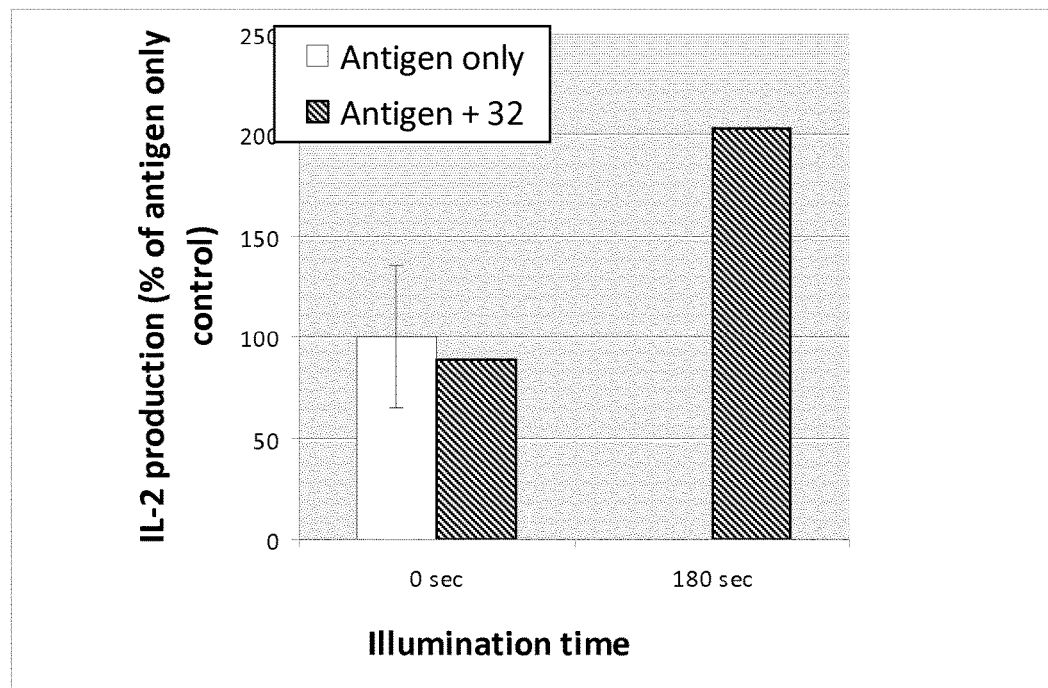
Figure 28:
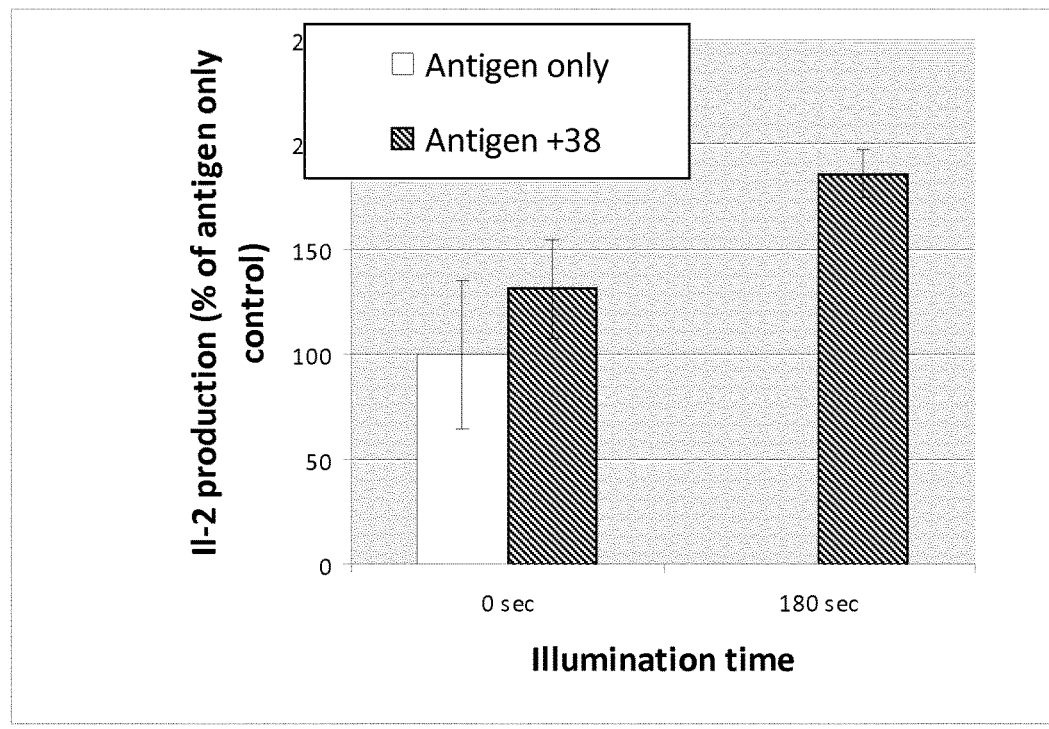

FIG. 28 shows IL-2 production in murine primary macrophages which were incubated with compound 32 (A) and 38 (B) and the ovalbumin OVA 257-264 peptide antigen in an antigen-specific T cell setting with an ovalbumin-specific (OVA 257-264) CD8+ T cell clone. IL-2 production from activated CD8+ T cells was analyzed by an ELISA.

Example 1—Synthesis of
Meso-Tetraphenylporphyrin-Chitosan-Based
Nanocarriers

Highly water soluble chitosan nanocarriers tethered with the photosensitizer meso-tetraphenylporphyrin (TPP) were synthesized, in a 7 step procedure, from 3,6-di-O-tert-butyldimethylsilyl-chitosan (DiTBDMS-CS) and 5-(p-aminophenyl)-10,15,20-triphenylporphyrin [TPP(p-NH$_2$)$_1$] as starting materials. DiTBDMS-CS is highly soluble in CH$_2$Cl$_2$ and the highly lipophilic photosensitizer could therefore be introduced in a quantitative reaction to give 0.1 and 0.25 degree of substitution. This was followed by introduction of trimethylammoniumyl and or 1-methylpiperazinyl groups onto the polymer backbone in order to increase aqueous solubility of the final deprotected carriers. It was shown that the method is highly reproducible and that the obtained material could be fully characterized by solid state NMR, FT-IR, and $^1$H NMR. UV-Vis, fluorescence and NMR investigations showed that the carriers are dynamic structures, which form nanoparticle-like structures in aqueous solution with a core of semi-solid m-stacked photosensitizers. In lipophilic environments it is probable that these structures can unfold and the photosentizer moiety can thus be inserted into the cell membrane.

General Materials and Methods

The chitosan polymer was donated by Genis EHF, Iceland and was used for the synthesis [chitosan polymer GO 30626-2 (95% DD, 95 cp)]. All solvents and reagents were purchased commercially and used without further purification. NMR spectra were recorded on a DRX 400 MHz Bruker NMR spectrometer at 298 K and chemical shifts were reported relative to the deuterated NMR solvent used [$^1$H NMR: CDCl$_3$ (7.26 ppm), DMSO-d$_6$ (2.50 ppm); $^{13}$C NMR: CDCl$_3$ (77.16 ppm), DMSO-d$_6$ (39.52 ppm)]. The Acetone peak (2.22 ppm) was used as the internal reference for D$_2$O as solvents. The protons (ortho, meta, para) on the phenyl rings of porphyrins are identified with respect to their positions relative to the porphyrin ring system and not with respect to the substituent on the phenyl ring.

Solid-state $^{13}$C NMR of compounds 17B and 19B was obtained from the Department of Chemistry, Durham University. These spectra were obtained using a Varian VNMRS spectrometer operating at 100.56 MHz for $^{13}$C. Cross-polarization magic-angle spinning experiments were carried out with a 6 mm (rotor o.d.) probe. The spectra were recorded at a spin-rate of 6.8 kHz, with a 1 ms contact time, a 1.5 s recycle delay and with "TOSS" spinning sideband suppression. Spectral referencing is with respect to an external sample of neat tetramethylsilane carried out indirectly by setting the high-frequency signal from adamantane to 38.5 ppm.

Mass spectra were recorded on Bruker Autoflex III or a Bruker micrOTOF-Q11. FTIR-measurements were performed with an AVATAR 370 FT-IR instrument (Thermo Nicolet Corporation, Madison, USA). Samples (2-3 mg) were kneaded thoroughly with KBr. The sample was pressed into pellets with a Specac compressor (Specac Inc., Smyrna, USA). Melting Points were recorded on Buchi Melting Point B-540. Polymer samples were dialyzed using Spectra/Por Dialysis Membrane (MWCO: 3500).

Absorption and Steady-State Fluorescence Spectra.

UV-Vis measurements were recorded on a Perkin-Elmer Lambda 25 UV-Vis. spectrometer equipped with a Peltier Temperature Programmer. Fluorescence emission spectra were obtained using a SPEX FluoroMax spectrometer, using a cell with spectral range 170-2200 nm (Spectrocell Corporation, Oreland, Pa., USA). Absorption spectra were recorded at 20° C. and fluorescence emission spectra were recorded at ambient temperature, using quartz cuvette with a 10 mm path length. All the fluorescence spectra were recorded with constant slit widths, 1 nm for excitation and 1 nm for emission and fluorescence spectra were averaged over three scans for quantum yield study. However, for FIG. 5 (III) fluorescence spectra were obtained with slit widths 3 nm for excitation and 3 nm for emission.

Fluorescence quantum yields of compounds 3, 5, 16A-19B (all excited at $\Delta$ex.=$\lambda$max=419 nm) were determined relative to a dilute solution of standard anthracene ($\phi_F$=0.27, $\lambda$ex=365.5 nm) in absolute ethanol by using the steady-state comparative method. using the following equation:

$$\phi_X = \phi_{ST}(Grad_X/Grad_{ST})(\eta_S^2,\eta_{ST}^2)$$

where, the subscripts ST and X denote standard and test respectively, $\phi$ is the fluorescence quantum yield, Grad the gradient from the plot of integrated fluorescence intensity versus absorbance, and $\eta$ the refractive index of the solvent.

Stability Study:

For the physical stability study 17A was dissolved in $H_2O$ (1 mg/mL), sonicated for 30 minutes, centrifuged (on HERMLE Z-320 4000 rpm for 10 min), decanted and wrapped with aluminium foil. UV-Vis absorbance were measured at $\lambda_{max}$=419 nm in $H_2O$ over the period of 0-90 days.

Determination of the Degree of Substitution (DS) by $^1$H NMR.

In order to calculate the substitution degrees of the TPP—NH-Pip, we used 1H NMR of the final compounds. For calculating DS from Final compounds 16A-19B, we used integration values of TPP peaks (from TPP—NH-Pip part) and that of H-1 (from chitosan part) peaks. The integral of TPP (four peaks from aromatic region) was considered, while the integrals of H-1 group was calculated and used in the following equations:

$$DS=(\int Aromatic\ TPP\ peaks/27)/(\int H-1\ peak/1)$$

Under this condition the polymer backbone is partially overlapped by the HDO peak but the DS can be determined with good accuracy from the relative ratio of the integrals of the H-1 peak and the TPP peaks.

For calculating the DS of TPC—NH-Pip AND TPC—CO-Pip we used intermediate compounds 29 & 34 and integration values of TPC peaks (from TPC—NH-Pip or TPC—CO-Pip in the aromatic region as well as $\alpha$-pyrrole NH peak integrations) and that of TBDMS peaks integration (from chitosan) in the following equations:

$$DS=(\int Aromatic\ TPC\ peaks+\alpha\ pyrrole\ NH\ peak/27)/(\int TBDMS\ peak/30)$$

For calculating the DS of the TEGylation for various chitosan derivatives we used corresponding $^1$H NMR. We considered the integration values of the H-1 peak of chitosan and the integration value of $CH_3$ (of terminal ethyl peak of TEG) on a chitosan backbone The integration value for the -ethyl end triplet would be equal to 3 if the substitution degree is 100%. Therefore, the equation is following:

$$DS(\%)(\int Ethyl\ peak(end\ triplet,CH3)/3)/(\int H-1\ peak/1)*100\%$$

SEM and Elipsometry.

Solutions were spin-coated at 1000 rpm onto pristine silicon <100> substrates (15 mm×15 mm) using a conventional spinner in a Class-100 clean room environment. The silicon has a layer of native oxide of approximately 15 Å thickness. Furthermore, 10 µl of the same solutions were pipetted directly onto silicon substrates and allowed to dry in air at room temperature. The coated substrates were imaged in a Zeiss LEO 1550 scanning electron microscope at 10 keV acceleration voltage and 2 mm working distance using an in-lens detector.

Water Contact Angle Measurements.

Water contact angles were determined using a KSV CAM 200 optical contact angle meter (KSV Instruments). A 5 µl deionized water droplet was dropped on the centre of the silicone wafer and water contact angles determined based on the Laplace & Young equation. Measurements were done at room temperature and ambient humidity.

Synthesis

Figure 1:
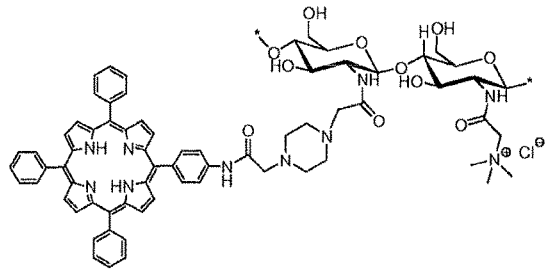
Figure 1:
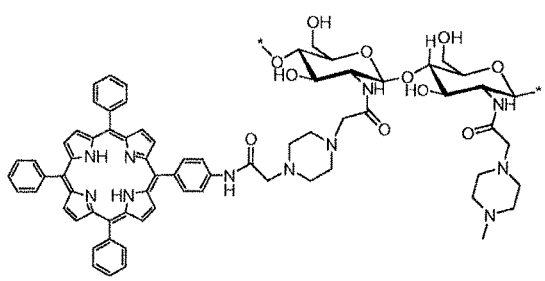
Figure 1:
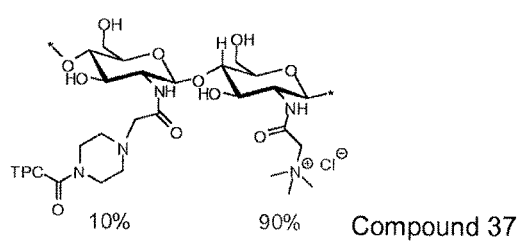
Figure 1:
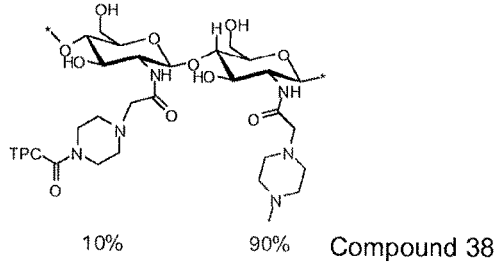
Figure 1:
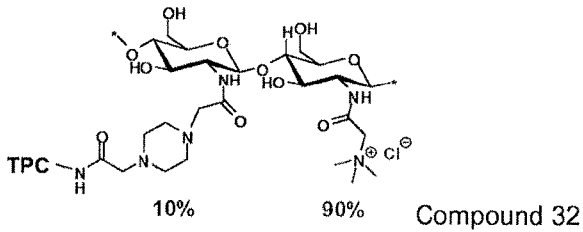
Figure 1:
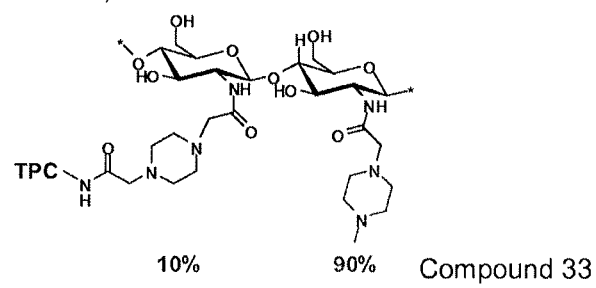
Figure 1:
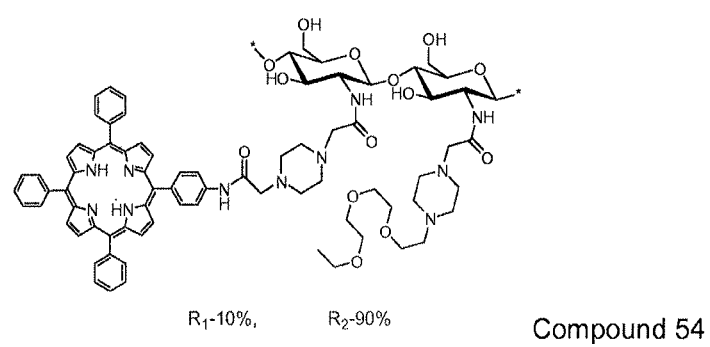
Figure 1:
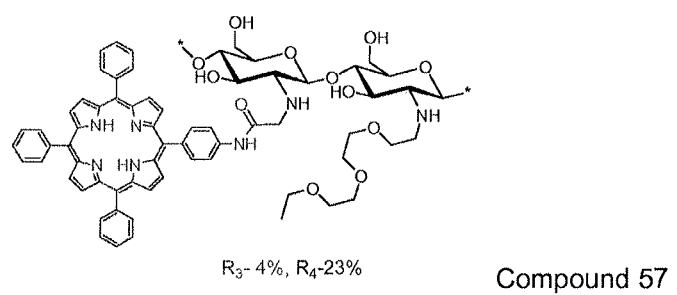
Figure 2:
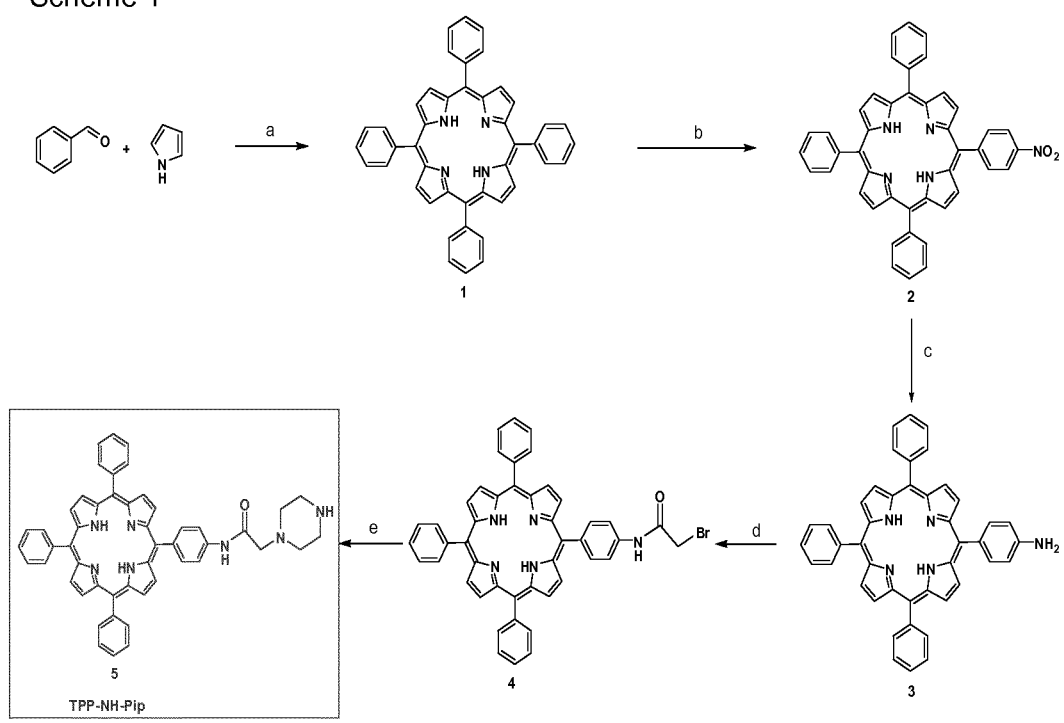

See scheme 1 in FIG. 2 for synthesis of TPP—NH-Pip

Meso-Tetraphenylporphyrin (1). Following the literature procedure (Adler, *J Organic Chem* 1967, 32:476).

5-(4-Nitrophenyl)-10,15,20-triphenylporphyrin [TPP(p-$NO_2$)$_1$] (2).

Following the literature procedure (Luguya R et al. *Tetrahedron* 2004, 60:2757).

5-(4-Aminophenyl)-10,15,20-triphenylporphyrin [TPP(p-$NH_2$)$_1$] (3).

Following the literature procedure (Luguya R et al. *Tetrahedron* 2004, 60:2757).

5-(4$\alpha$-Bromoacetylamidophenyl)-10,15,20-triphenylporphyrin (4).

Compound 3 (500 mg, 0.793 mmol) was dissolved in $CH_2Cl_2$ (15 mL) and stirred under an $N_2$ atmosphere. Triethylamine (0.24 mL, 1.75 mmol) was added followed by drop wise addition of bromoacetyl bromide (0.097 mL, 1.11 mmol) at rt and the stirring continued at it for 1 h. The reaction mixture was diluted into $CH_2Cl_2$(45 mL), washed with water (2×25 mL) and brine (20 mL). The organic layer was then dried over $Na_2SO_4$ and concentrated in vacuo. Crude product was purified by silica gel column chromatography, using $CH_2Cl_2$ and hexane as eluent, which yielded 385 mg (64%) of desired product 4. TLC (Hexane/$CH_2Cl_2$ 3:7): Rf=0.17; FT-IR, v cm$^{-1}$: 3313 (N—H), 3049, 3019 (aryl C—H), 1687, 1594 (CONH), 1556, 1514, 1471, 1439, 1399, 1348, 1177, 1153, 964, 798, 726, 699; $^1$H NMR (CDCl$_3$): $\delta$=8.88-8.91 (m. 8H, $\beta$-pyrrole H), 8.41 (br s, 1H, TPPNHCO), 8.22-8.27 (m, 8H, tetraphenyl H$_O$), 7.91 (d, J=8 Hz, 2H, CONH-phenyl-Hm), 7.75-7.80 (m, 9H, triphenyl-Hm,p), 4.15 (s, 2H, COCH$_2$Br), -2.70 (br s, 2H, $\alpha$-pyrrole NH) ppm; $^{13}$C NMR (CDCl$_3$): $\delta$=163.78, 142.26, 139.20, 136.78, 135.25, 134.68, 131.23, 127. 87, 126.83, 120.42, 120.38, 119.24, 118.34, 29.72 ppm; MS (ESI): m/z calcd. for $C_{46}H_{33}BrN_5O$ ([M+H]$^+$) 750.1863 found 750.1864; UV-vis (DMSO): $\lambda_{max}$: 417, 517, 542, 597, 650 nm.

5-(4α-Piperazineacetylamidophenyl)-10,15,20-triphenyl-porphyrin [TPP—NH-Pip[(5).

Compound 4 (275 mg, 0.366 mmol) and excess piperazine (158 mg, 1.83 mmol) was mixed together in $CH_2Cl_2$ (10 mL) and stirred at rt for 1 h under an $N_2$ atmosphere. After completion of the reaction, the reaction mixture was diluted with $CH_2Cl_2$ (85 mL) and washed with water (2×40 mL) and brine (35 mL). The organic layer was dried over $Na_2SO_4$ and concentrated under vacuo. The crude product was purified by silica gel column chromatography using 1:12 MeOH:$CH_2Cl_2$ as eluent to afford titled compound 5 (260 mg, 94%) as a purple solid. TLC ($CH_2Cl_2$/MeOH, 9:1): Rf=0.15; FT-IR (KBr): v 3442 (pip. NH), 3312 (aryl N—H), 3052, 3022 (aryl C—H), 2903, 2816 (aliphatic CH2), 1691, 1596 (CONH), 1557, 1517, 1471, 1439, 1400, 1349, 1309, 1179, 1153, 1071, 1001, 965, 799, 728, 700 cm$^{-1}$; $^1$H NMR (CDCl$_3$): δ=9.51 (br s, 1H, TPP—NHCO), 8.89-8.93 (m, 8H, β-pyrrole H), 8.23-8.26 (m, 8H, tetraphenyl H$_O$), 8.01 (d, J=8.0 Hz, 2H, Pip-NH-phenyl-Hm), 7.75-7.81 (m, 9H, triphenyl-Hm,p), 3.31 (s, 2H, COCH$_2$Pip.), 3.11 (t, 4H), 2.77 (br t, 4H), 2.60 (br s, 1H, piperazine NH), −2.71 (br s, α-pyrrole 2H) ppm; $^{13}$C NMR (CDCl$_3$): δ=168.75, 142.30, 138.26, 137.44, 135.33, 134.68, 131.26, 127.86, 126.83, 120.32, 119.66, 117.89, 62.87, 54.53, 46.24 ppm; MS (ESI): m/z calcd. for $C_{50}H_{42}N_7O$ ([M+H]$^+$) 756.3445 found 756.3467; UV-vis (DMSO): $\lambda_{max}$: 417, 517, 542, 597, 650 nm.

Figure 3:
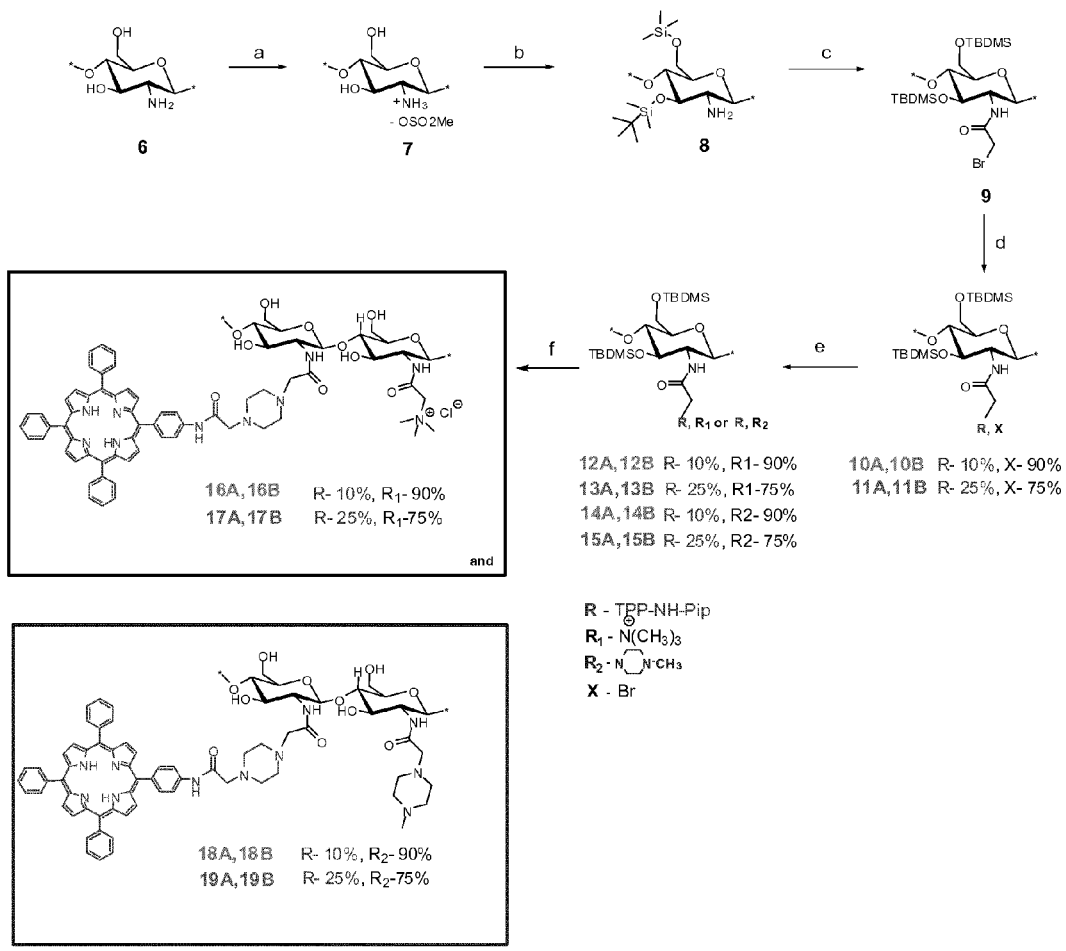

See scheme 2 in FIG. 3 and Scheme 5 in FIG. 12

Chitosan mesylate (7).

Synthesized according to our previously published procedure (Song et al. *Carbohydrate Polymers* 2010, 81:140).

3,6-O-di-tert-butyldimethylsilyl chitosan [DiTBDMS-CS] (8).

Synthesized according to our previously published procedure (Song et al. *Carbohydrate Polymers* 2010, 81:140).

N-bromoacetyl-3,6-O-DiTBDMS-CS [BrA-DiTBDMS-CS] (9).

DiTBDMS-CS 8 (1 g, 2.60 mmol) was dissolved in dry $CH_2Cl_2$ (15 mL) in a round bottom flask under an $N_2$ atmosphere. Then the reaction mixture was cooled to −20° C. with an ice/salt mixture. Et$_3$N (1.81 mL, 13 mmol) was added followed by slow drop wise addition of bromoacetyl bromide (0.91 mL, 10 mmol). Stirred for 1 h. The reaction mixture was diluted with $CH_2Cl_2$ and concentrated in vacuo. The crude product was stirred in acetonitrile, filtered and washed with fresh acetonitrile. Dry material was dissolved and extracted in $CH_2Cl_2$, washed with water and brine, and dried over $Na_2SO_4$, concentrated under vacuo. Faint yellow powdered product 9 was obtained 1.2 g (92% yield). FT-IR (KBr): v 3402 (br, NH), 2957, 2931, 2886, 2858 (s, C—H TBDMS), 1682 (vs, C=O amide I), 1530 (vs, C=O amide II), 1473, 1391, 1362, 1311, 1259, 1101, 1005, 837, 777 (Si—C), 669 cm$^{-1}$; NMR (CDCl$_3$) δ ppm: 4.40 (br s, H-1), 4.02-3.26 (m, H-2 GlcN, H-3, H-4, H-5, H-6, H-6' and 2H GluNH—C=OCH$_2$Br), 0.90 and 0.88 (br s, (CH$_3$)$_3$C), 0.13 and 0.07 (br s, (CH$_3$)$_2$Si) ppm.

(N-TPP—NH-Pip-acetyl)$_{0.1}$-(N-bromoacetyl)$_{0.9}$-DiTBDMS-CS [TPPp$_{0.1}$-BrA$_{0.9}$-DiTBDMS-CS] (10A).

Compound 9 (700 mg, 1.38 mmol) and compound NH-pip-TPP 5 (105 mg, 0.138 mmol) were dissolved in $CH_2Cl_2$ under an $N_2$ atmosphere. Exact equimolar quantity of Et$_3$N (19.3 µL, 0.130 mmol) with respective to 5 was added and reaction mixture was stirred at rt for 24 h. Total consumption of starting material was confirmed by TLC. The reaction mixture was diluted with $CH_2Cl_2$, extracted, and washed with water and brine. The organic layer was dried over $Na_2SO_4$, concentrated under vacuo to yield 730 mg (92%) product 10A. FT-IR (KBr): v 3324 (br, NH), 2955, 2929, 2884, 2856 (s, C—H TBDMS), 1678 (vs, C=O amide 1), 1600, 1524 (vs, C=O amide II), 1472, 1403, 1361, 1311, 1256, 1098, 1004, 966, 837, 801, 778, 701, 670, 550 cm$^{-1}$; $^1$H NMR (CDCl$_3$) δ ppm: 9.30(s, TPPNHCO), 8.85 (m, β-pyrrole H), 8.23-8.20 (m, phenyl-Ho & Pip-NHTPP-phenyl-Hm), 7.97 (d, J=8.0 Hz, RNTPP-phenyl-Ho), 7.79-7.73 (m, triphenyl-Hm,p), 4.41 (br s, H-1), 4.13-3.50 (m, H-2 GlcN, H-3, H-4, H-5, H-6, H-6' and 2H GluNH-C=O, TPPNHCOCH$_2$pip, CH$_2$CONGlc and (CH$_2$)$_2$ of piperazine), 2.81-2.86 (m, piperazine-H), 0.92, 0.89 (br s, (CH$_3$)$_3$C), 0.14, 0.07 (br s, (CH$_3$)$_2$Si), −2.77 (br s, α-pyrrole NH) ppm; UV-vis (DMSO): $\lambda_{max}$: 417, 517, 542, 597, 650 nm.

TPPp$_{0.1}$-BrA$_{0.9}$-DiTBDMS-CS (10B):

Compound 10B (1.3 mg, 91%) was prepared exactly as the above procedure using intermediate 5 (180 mg, 0.24 mmol) and 9 (1.2 g, 2.4 mmol).

TPPp$_{0.25}$-BrA$_{0.75}$-DiTBDMS-CS (11A). Compound 9 (550 mg, 1.09 mmol) and compound NH-pip-TPP 5 (206 mg, 0.273 mmol) were dissolved in $CH_2Cl_2$ under an $N_2$ atmosphere. An exact equimolar quantity of Et$_3$N (38 µL, 0.27 mmol) was added with respect to 5 and the reaction mixture was stirred at rt for 24 h. Total consumption of starting material was confirmed by TLC. The reaction mixture was diluted with $CH_2Cl_2$, extracted, and washed with water and brine. The organic layer was dried over $Na_2SO_4$, and concentrated under vacuo to yield 670 mg (91%) of product 11A. FT-IR (KBr): v 3317 (br, NH), 2952, 2926, 2883, 2855 (s, C—H TBDMS), 1680 (vs, C=O amide I), 1598, 1520, 1471, 1440, 1402, 1361, 1309, 1254, 1096, 1002, 966, 837, 800, 778, 730, 701, 667, 558 cm$^{-1}$; $^1$H NMR (CDCl$_3$) δ ppm: 9.30(s, TPPNHCO), 8.85 (m, β-pyrrole H), 8.22-8.20 (m, phenyl-Ho & Pip-NHTPP-phenyl-Hm), 7.97 (d, J=8.0 Hz, RNTPP-phenyl-Ho), 7.80-7.75 (m, triphenyl-Hm,p), 4.40 (br s, H-1), 4.06-3.63 (m, H-2 GlcN, H-3, H-4, H-5, H-6, H-6' and 2H GluNH—C=O, TPPNHCOCH$_2$pip, CH$_2$CONGlc and (CH$_2$)$_2$ of piperazine), 2.81-2.86 (m, piperazine-H), 0.92, 0.89 (br s, (CH$_3$)$_3$C), 0.14, 0.10, 0.07 and 0.02 (br s, (CH$_3$)$_2$Si), −2.77 (br s, α-pyrrole NH) ppm; UV-vis (DMSO): $\lambda_{max}$: 417, 517, 542, 597, 650 nm.

TPPp$_{0.25}$-BrA$_{0.75}$-DiTBDMS-CS (11B).

Compound 11B (1.35 g, 92%) was prepared exactly as the above procedure using intermediate 5 (415 mg, 0.55 mmol) and 9 (1.1 g, 2.18 mmol).

General procedure A for Synthesis of compounds 12A, 12B, 13A and 13B (N-TPP—NH-Pip-acetyl)$_{0.1}$-(N—(N,N,N-trimethylammoniumyl)acetyl)$_{0.9}$-DiTBDMS-CS [TPPp$_{0.1}$-DiTBDMS-CS-TMA$_{0.9}$] (12A).

Compound 10A (350 mg, 0.61 mmol) was dissolved in $CH_2Cl_2$ under $N_2$ atmosphere. An excess amount of trimethylamine solution was added and the reaction mixture was stirred at rt for 24 h. Solvent was removed in vacuo. The crude product was dried completely under high vacuum yielding crude product 12A (420 mg, 99%) as a purple solid. FT-IR (KBr): v 3426, 3021, 3011, 2962, 2855, 27.7, 2560, 2438, 1749, 1689, 1599, 1563, 1482, 1443, 1401, 1360, 1288, 1254, 1053, 1010, 966, 922, 901, 837, 797, 779, 744, 701, 671, 552 cm$^{-1}$.

TPPp$_{0.1}$-DiTBDMS-CS-TMA$_{0.9}$ (12B).

The general procedure A was followed using 10B (600 mg, 1.04 mmol) and NMe$_3$ to give 12B as a crude solid (720 mg, 99%).

TPPp$_{0.25}$-DiTBDMS-CS-TMA$_{0.75}$ (13A).

The general procedure A was followed using 11A (300 mg, 0.44 mmol) and NMe$_3$ to give 13A crude solid (340 mg, 98%). FTIR (KBr): ν 3415, 3021, 3011, 2962, 2854, 1749, 1686, 1598, 1522, 1482, 1442, 1402, 1360, 1311, 1288, 1252, 1053, 1010, 966, 922, 901, 837, 798, 779, 744, 701, 671, 558 cm$^{-1}$.

TPPp$_{0.25}$-DiTBDMS-CS-TMA$_{0.75}$ (13B).

The general procedure A was followed using 11B (600 mg, 0.89 mol) and NMe$_3$ to give 13B as a crude solid (685 mg, 99%)

General procedure B for compounds 14A, 14B, 15A & 15B (N-TPP—NH-Pip-acetyl)$_{0.1}$-(N—(N-methylpiperazinyl) acetyl)$_{0.9}$-DiTBDMS-CS  [TPPp$_{0.1}$-DiTBDMS-CS-MP$_{0.9}$] (14A).

Compound 10A (350 mg, 0.61 mmol) was dissolved in CH$_2$Cl$_2$ under an N$_2$ atmosphere. An excess amount of 1-methylpiperizine was added and the reaction mixture was stirred at room temperature for 24 h. Solvent was removed in vacuo. Then crude product was dried completely under high vacuum yielding corresponding crude product 14A (425, 105%). FT-IR (KBr): ν 3378, 2950, 2930, 2884, 2854, 2798, 2694, 2608, 2477, 2223, 1678, 1617, 1519, 1461, 1394, 1371, 1293, 1253, 1168, 1092, 1051, 1003, 966, 939, 920, 837, 801, 779, 701, 671, 612 cm$^{-1}$.

TPPp$_{0.1}$-DiTBDMS-CS-MP$_{0.9}$ (14B).

The general procedure B was followed using 10B (600 mg, 1.04 mol) and 1-methylpiperazine to give 14B as crude solid (710 mg, 102%).

TPPp$_{0.25}$-DiTBDMS-CS-MP$_{0.75}$ (15A).

The general procedure B was followed using 11A (250 mg, 0.37 mmol) and 1-methylpiperazine to give 15A as a crude solid (290 mg, 104%). FT-IR (KBr): ν 3380, 2950, 2930, 2884, 2854, 2800, 2480, 1677, 1598, 1519, 1461, 1400, 1394, 1371, 1284, 1252, 1168, 1089, 1050, 1003, 966, 939, 920, 837, 801, 779, 732, 701, 671, 591 cm$^{-1}$.

TPP$_{0.25}$-DiTBDMS-CS-MP$_{0.75}$ (15B).

The general procedure B was followed using 11B (650 mg, 0.96 mol) and 1-methylpiperazine to give 15B as a crude solid (735 mg, 102%).

General TBDMS Deprotection Procedure C for Compounds 16A, 17A, 18A & 19A (1$^{st}$ Batch Compounds).

TPPp$_{0.1}$-CS-TMA$_{0.9}$ (16A).

The material 12A (350 mg, 0.50 mmol) was dissolved in MeOH (5-10 mL) followed by addition of concentrated HCl (2-3 mL). The reaction mixture was stirred for 12 h at rt. An excess amount of deionised water was added into the reaction mixture and stirred for 30 minutes before dialysis against 8% NaCl for one day, and against deionised water for 3 days. During this time the colour of the solution changed gradually from dark green to red. The red colour solution was then freeze-dried to yield a brown sponge-like material. The materials were again deprotected, ion exchanged, dialyzed and freeze-dried. The procedure was repeated using the same conditions in order to remove trace amount of TBDMS to obtain 16A (210 mg, 89%) brown sponge material. FT-IR (KBr): ν 3419 (br, O—H), 3064 (C—H), 1683, 1558, 1506, 1488, 1473, 1403, 1296, 1153, 1112, 1068, 1032, 966, 911, 800, 730, 701, 618 cm$^{-1}$; $^1$H NMR (DMSO-d$_6$: D$_2$O 96:4) δ ppm: 8.81 (br m, β-pyrrole H), 8.12-8.16 (br m, phenyl-Ho & Pip-NHTPP-phenyl-Hm), 8.04 (br d, J=8.0 Hz, RNTPP-phenyl-Ho), 7.75-7.84 (m, triphenyl-Hm,p), 4.66 (br s, H-1), 4.21 (br s, BrCH$_2$C=O), 3.83-3.54 (m, H-2 GlcNAc, H-3, H-4, H-5, H-6, H-6"), 3.32 (s, $^+$N(CH$_3$)$_3$)) ppm.

TPPp$_{0.25}$-CS-TMA$_{0.75}$ (17A).

The general procedure C was followed using 13A (240 mg, 0.30 mmol) and conc.HCl/MeOH to give 17A as a purple solid (120 mg, 71%). FT-IR (KBr): ν 3392, 3061, 2950, 1683, 1559, 1506, 1489, 1473, 1402, 1350, 1296, 1154, 1112, 1068, 1032, 966, 911, 800, 730, 701, 619 cm$^{-1}$; $^1$H NMR (DMSO-d$_6$: D$_2$O 98:2) δ ppm: 8.81 (br m, β-pyrrole H), 8.12-8.16 (br m, phenyl-Ho & Pip-NHTPP-phenyl-Hm), 8.04 (br d, J=8.0 Hz, RNTPP-phenyl-Ho), 7.79-7.87 (m, triphenyl-Hm,p), 4.50 (br s, H-1), 4.15 (br s, BrCH$_2$C=O), 3.27-3.65 (m, H-2 GlcNAc, H-3, H-4, H-5, H-6, H-6'), 3.24 (s, $^+$N(CH$_3$)$_3$)) ppm.

TPPp$_{0.1}$-CS-MP$_{0.9}$ (18A).

The general procedure C was followed using 14A (350 mg, 0.52 mmol) and conc.HCl/MeOH to give 18A as a purple solid (200 mg, 87%). FT-IR (KBr): ν 3419 (br, O—H), 3057 (C—H), 1683, 1558, 1474, 1403, 1296, 1234, 1154, 1112, 1068, 1032, 966, 930, 911, 799, 730, 701 cm$^{-1}$; $^1$H NMR (DMSO-d$_6$: D$_2$O 96:4) δ ppm: 8.83 (br m, β-pyrrole H), 8.13-8.19 (br m, phenyl-Ho & Pip-NHTPP-phenyl-Hm), 8.08 (br d, J=8.0 Hz, RNTPP-phenyl-Ho), 7.79-7.87 (m, triphenyl-Hm,p), 4.48 (br s, H-1), 3.24-3.78 (m, H-2 GlcNAc, H-3, H-4, H-5, H-6, H-6"), 3.92 (dd, J=12 Hz, Pip-CH$_2$C=O), 2.30-2.67 (m, piperazine (CH$_2$)$_4$), 2.48 (br s, piperazine, N—CH$_3$) ppm.

TPPp$_{0.25}$-CS-MP$_{0.75}$ (19A).

The general procedure C was followed using 15A (200 mg, 0.26 mmol) and 1-methylpiperazine to give 19A as a purple solid (80 mg, 58%). FT-IR (KBr): ν 3392, 3056, 2947, 1683, 1558, 1520, 1489, 1472, 1458, 1400, 1349, 1309, 1248, 1154, 1068, 1031, 1001, 966, 911, 800, 729, 701, 658 cm$^{-1}$. $^1$H NMR (DMSO-d$_6$: D$_2$O 96:4) δ ppm: 8.83 (br m, β-pyrrole H), 8.14-8.20 (br m, phenyl-Ho & Pip-NHTPP-phenyl-Hm), 8.08 (br d, J=8.0 Hz, RNTPP-phenyl-Ho), 7.78-7.86 (m, triphenyl-Hm,p), 4.50 (br s, H-1), 3.24-3.78 (m, H-2 GlcNAc, H-3, H-4, H-5, H-6, H-6'), 3.92 (dd, J=12 Hz, Pip-CH$_2$C=O), 2.28-2.67 (m, piperazine (CH$_2$)$_4$), 2.48 (br s, piperazine, N—CH$_3$) ppm.

General TBDMS deprotection procedure D for Final compounds 16B, 17B, 18B & 19B (2$^{nd}$ Batch Compounds). (Compound 16B as Representative). TPPp$_{0.1}$-CS-TMA$_{0.9}$ (16B): The material 12B (600 mg, 0.86 mmol) was dissolved in N-Methyl-2-pyrrolidone (NMP) (5-10 mL) followed by addition of an excess amount of tetra-n-butylammonium-fluoride (TBAF). The reaction mixture was stirred for 24 h at 55° C. and cooled and acidified with dilute HCl and stirred for 30 minutes before dialysis against 8% NaCl (w/v) in deionised water for two days and against deionised water for 3 days. During this time the colour of the solution changed gradually from grey to red. The red colour solution was then freeze-dried to yield a brown sponge-like material. The materials were again deprotected, ion exchanged, dialyzed and freeze-dried. The procedure was repeated using the same conditions in order to remove the remaining trace amount of TBDMS to obtain 16B (350 mg, 87%) brown sponge material. FTIR (KBr): ν 3405, 2943, 2817, 1655, 1528, 1459, 1401, 1375, 1308, 1248, 1153, 1111, 1068, 1031, 966, 832, 799, 729, 702 cm$^{-1}$; $^1$H NMR (DMSO-d$_6$: D$_2$O 96:4) δ ppm: 8.82 (br m, β-pyrrole H), 8.12-8.16 (br m, phenyl-Ho & Pip-NHTPP-phenyl-Hm), 8.04 (br d, J=8.0 Hz, RNTPP-phenyl-Ho), 7.75-7.84 (m, triphenyl-Hm,p), 4.47 (br s, H-1), 4.04 (br s, BrCH$_2$C=O), 3.24-3.55 (m, H-2 GlcNAc, H-3, H-4, H-5, H-6, H-6"), 3.19 (br s, $^+$N(CH$_3$)$_3$)) ppm.

TPPp$_{0.25}$-CS-TMA$_{0.75}$ (17B):

The general procedure C was followed using 13B (650 mg, 0.84 mmol) and TBAF/NMP to give 17B as a purple solid (400 mg, 87%). FTIR(KBr):ν 3396, 2942, 2829, 1662, 1526, 1458, 1441, 1401, 1310, 1249, 1068, 1032, 1002, 966, 800, 730, 701 cm$^{-1}$; $^1$H NMR (DMSO-d$_6$: D$_2$O 98:2) δ ppm: 8.81 (br m, β-pyrrole H), 8.12-8.16 (br m, phenyl-Ho & Pip-NHTPP-phenyl-Hm), 8.08 (br d, J=8.0 Hz, RNTPP-phenyl-Ho), 7.74-7.86 (m, triphenyl-Hm,p), 4.51 (br s, H-1), 4.10 (br s, BrCH$_2$C=O), 3.26-3.55 (m, H-2 GlcNAc, H-3, H-4, H-5, H-6, H-6'), 3.22 (br s, $^+$N(CH$_3$)$_3$)) ppm; Solid-state $^{13}$C NMR (100.56 MHz): δ 170.85, 164.68, 128.11, 119.45, 101.53, 75.39, 61.09, 55.47.

TPPp$_{0.1}$-CS-MP$_{0.9}$ (18B):

The general procedure C was followed using 14B (600 mg, 0.90 mmol) and TBAF/NMP to give 18B as a purple solid (315 mg, 80%). FTIR (KBr): ν 3396, 3315 (br, OH, NH), 2941, 1655 (vs, C=O amide I), 1534 (vs, C=O amide II), 1522, 1471, 1440, 1401, 1375, 1310, 1244, 1069, 1030, 1001, 966, 800, 729, 701 cm$^{-1}$; $^1$H NMR (DMSO-d$_6$: D$_2$O 98:2) δ ppm: 8.81 (br m, β-pyrrole H), 8.13-8.19 (br m, phenyl-Ho & Pip-NHTPP-phenyl-Hm), 8.07 (br d, J=8.0 Hz, RNTPP-phenyl-Ho), 7.79-7.85 (m, triphenyl-Hm,p), 4.48 (br s, H-1), 3.24-3.72 (m, H-2 GlcNAc, H-3, H-4, H-5, H-6, H-6'), 3.92 (dd, J=12 Hz, Pip-CH$_2$C=O), 2.33-2.67 (m, piperazine (CH$_2$)$_4$), 2.48 (br s, piperazine, N—CH$_3$) ppm.

TPPp$_{0.1}$-CS-MP$_{0.9}$ (19B):

The general procedure C was followed using 15B (700 mg, 0.93 mmol) and TBAF/NMP to give 19B as a purple solid (415 mg, 85%). FTIR (KBr): ν 3396, 3315 (br, OH, NH), 2941, 1655 (vs, C=O amide I), 1534 (vs, C=O amide II), 1522, 1471, 1440, 1401, 1375, 1310, 1244, 1069, 1030, 1001, 966, 800, 729, 701 cm$^{-1}$; $^1$H NMR (DMSO-d$_6$: D$_2$O 95:5) δ ppm: 8.82 (br m, β-pyrrole H), 8.13-8.19 (br m, phenyl-Ho & Pip-NHTPP-phenyl-Hm), 8.07 (br d, J=8.0 Hz, RNTPP-phenyl-Ho), 7.79-7.87 (m, triphenyl-Hm,p), 4.49 (br s, H-1), 3.24-3.78 (m, H-2 GlcNAc, H-3, H-4, H-5, H-6, H-6'), 3.92 (dd, J=12 Hz, Pip-CH$_2$C=O), 2.30-2.67 (m, piperazine (CH$_2$)$_4$), 2.40 (br s, piperazine, N—CH$_3$) ppm; Solid-state $^{13}$C NMR (100.56 MHz): δ 171.63, 138.74, 127.97, 119.74, 101.93, 75.54, 61.54, 55.42, 45.34 ppm.

Results and Discussion

Nucleophilic TPP intermediate 5.

In the current study, TPP 1 has been synthesized on a large scale and used as the starting material. The mono-nitro TPP(p-NO$_2$)$_1$ 2 functionality was introduced regioselectively using 1.8 equivalent NaNO$_2$ in TFA, followed by reduction with SnCl$_2$.2H$_2$O to obtain the mono-aminoporphyrin TPP(p-NH$_2$)$_1$ 3 The previously reported procedure was simplified by avoiding time consuming purification of the crude material 2 before the reduction step. Aminoporphyrin 3 was then obtained after purification without compromising its overall yield (54%).

The aminoporphyrin TPP(p-NH$_2$)$_1$ 3 is known to be weakly nucleophilic and attempts to link this compound to electrophilic BrA-DiTBDMS-CS 9 by SN$^2$ attack did not give desired results in our initial study, even under harsh conditions. Thus, in order to convert this photosensitizer derivative into a more potent nucleophile, TPP(p-NH2)$_1$ was first acylated to give bromoacyl-TPP 4 followed by nucleophilic substitution with excess piperazine to give nucleophilic porphyrin intermediate TPP—NH-Pip 5. The piperazine motif has positive charge under physiological conditions (aqueous pH 7.4). The piperazine moiety is also suitable as a spacer due to low toxicity and biotransformations that involves several well-known metabolic reactions. The overall synthetic route for synthesis of TPP—NH-Pip is shown in Scheme 1 in FIG. 2.

Electrophilic chitosan intermediate 9.

Chitosan was modified, as previously reported to obtain DiTBDMS-CS 8. After protection of hydroxyl groups, solubility of the biopolymer dramatically changes and it becomes freely soluble in common organic solvents like CH$_2$Cl$_2$ which facilitates modification with highly lipophilic moieties. Thus the electrophilic intermediate BrA-DiTBDMS-CS 9 was prepared by reacting 8 with 2-bromoacetyl bromide (Scheme 2 in FIG. 3). This reaction requires precise control of the reaction time, temperature and equivalents ratios of the different reagents in order to avoid side reactions such as deprotection and esterification. Reaction of 8 with bromoacetylbromide at 0° C. for 1.5 h resulted in material that was insoluble in CH$_2$Cl$_2$ and FT-IR analysis revealed an ester peak at 1760 cm$^{-1}$ along with the amide peak at 1680 cm$^{-1}$ (data not shown). Thus it was necessary to precisely optimize the reaction in order to avoid side reactions and to obtain freely soluble material. The optimized conditions for this reaction require the use of exactly 4 equivalents of bromoacetylbromide and 5 equivalents of Et$_3$N and maintenance of the reaction temperature at −20° C. for 1 h. The obtained intermediate 9 was fully soluble in CH$_2$Cl$_2$ and the correct structure could be confirmed by $^1$H NMR and FT-IR analysis. Compound 9 was then used as a key electrophilic intermediate in the synthesis of the chitosan carriers.

TPP derivatives of Chitosan (16A-19B).

A total of eight TPP derivatives of chitosan compounds were synthesized in two separate batches of four different compounds. The first batch (labeled "A") was synthesized on an 80-200 mg scale and the second batch (labeled "B") was synthesized on a slightly larger 300-450 mg scale in order to confirm the reproducibility and consistency of the procedure.

The lipophilic PS was attached covalently to the polymer backbone by reaction of BrA-DiTBDMS-CS 9 with the nucleophilic TPP—NH-Pip 5 intermediate. The reaction was quantitative which facilitated good control of the degree of substitution in the resulting material. Preliminary investigations showed that carriers with a high degree of substitution (DS) of porphyrin were insoluble in aqueous solution and the modification was therefore limited to 0.1 and 0.25 DS (per glucosamine monomer unit). Thus, TPP—NH-Pip 5 was reacted in a controlled manner at 0.1 or 0.25 equivalents per monomer units of electrophilic chitosan intermediate 9 to obtain desired products TPPp$_{0.1}$-BrA$_{0.9}$-DiTBDMS-CS (10A/10B) or TPPp$_{0.25}$-BrA$_{0.75}$-DiTBDMS-CS (11A/11B) respectively. Progress of the reaction was monitored by TLC and the reaction was stopped when 5 was no longer present in order to avoid side reactions. $^1$H NMR analysis of these materials was consistent with the quantitative reaction in the covalent linkage of TPP to chitosan.

Cationic moieties were then introduced on to the TPP-substituted chitosan backbone in order to enhance the aqueous solubility of the carriers and to provide affinity to the endocytic membrane. Therefore, compounds 10A/10B and 11A/11B were reacted with an excess amount of Me$_3$N (TMA) to afford TPPp$_{0.1}$DiTBDMS-CS-TMA$_{0.9}$ (12A/12B) and TPPp$_{0.25}$_DiTBDMS-CS-TMA$_{0.75}$ (13A, 13B) respectively with a fixed cationic charge. Similarly, compounds 10A/10B and 11A/11B were reacted with an excess amount of 1-methyl piperazine (MP) to afford TPPp$_{0.1}$_DiTBDMS-CS-MP$_{0.9}$ (14A/14B) and TPPp$_{0.25}$DiTBDMS-CS-MP$_{0.75}$ (15A, 15B) respectively. The crude materials were used directly for the final deprotection steps.

Finally, crude materials from the first batch 12A-15A were deprotected by conc. HCl in MeOH at rt, 12 h where as crude materials from second batch 12B-15B were deprotected by TBAF/NMP at 60° C., 24 h methods to give final products 16A-19A and 16B-19B respectively. In both the cases the deprotection step was repeated in order to remove some trace amount of TBDMS (1.5-7%) that was still present after the first deprotection step. Deprotection with conc. HCl in MeOH has been used previously, but, recently the milder TBAF/NMP deprotection of DiTBDMS chitosan derivatives has been introduced in order to avoid highly acidic conditions which may contribute to the degradation of the polymer backbone. However, the disadvantage of the latter method is that it requires a lengthy dialyzing process in order to remove the NMP solvent. Trimethylammoniunm ($Me_3N^+$) derivatives [$TPPp_{0.1}$-CS-$TMA_{0.9}$ (16A, 16B) and $TPPp_{0.25}$-CS-$TMA_{0.75}$ (17A, 17B)] solubilized faster into water than the 1-methyl-piperazine derivatives [$TPPp_{0.1}$-CS-M $P_{0.9}$ (18A, 18B), $TPPp_{0.25}$-CS-$MP_{0.75}$ (19A, 19B)]. This may be due to the presence of the fixed ionic charge in the former carrier compounds.

Characterization of the Nano-Carriers.

Figure 4:
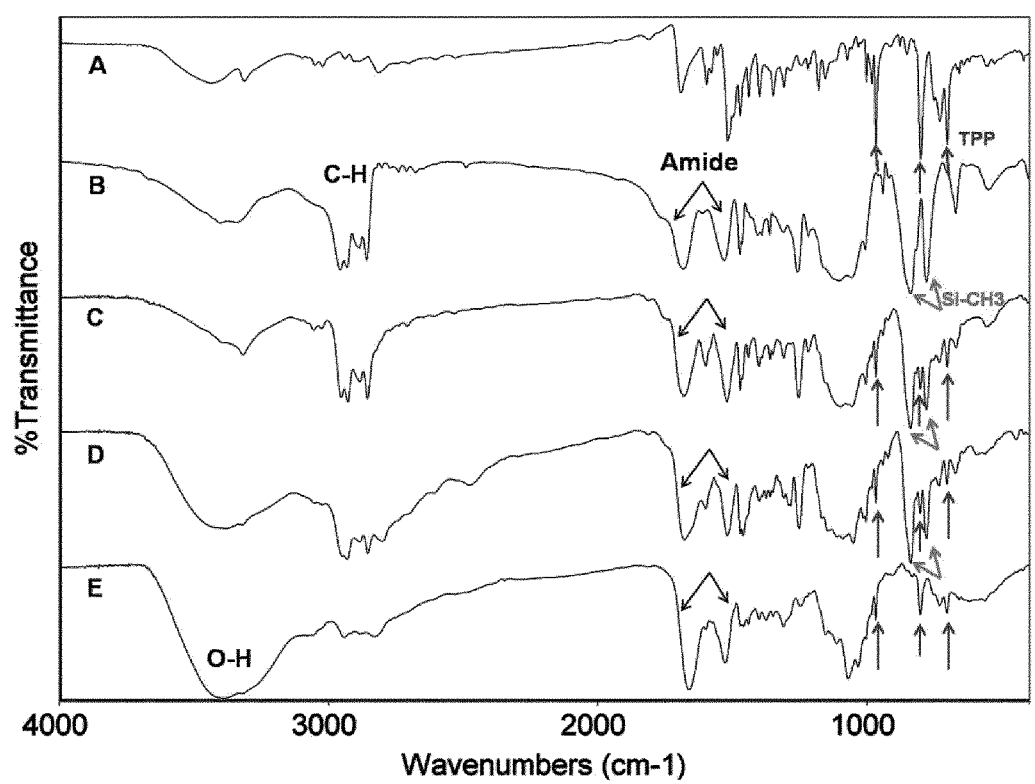
FIG. 4 shows representative FT-IR spectra overlay of all of the intermediates and the final compound in the synthesis of TPPp$_{0.1}$-CS-MP$_{0.9}$(18A): (A) TPP—NH-Pip 5; (B) BrA-DiTBDMS-C 9; (C) TPPp$_{0.1}$-CH$_2$CO-DiTBDMS-C 10A; (D) TPPp$_{0.1}$-DiTBDMS-CS-MP$_{0.9}$ 14A; (E) TPPp$_{0.1}$-CS-MP$_{0.9}$ 18A.

FT-IR Analysis:

The comparison of FT-IR spectra of various intermediates in the synthesis of the representative final compound $TPPp_{0.1}$-CS-$MP_{0.9}$ (18A) is shown in FIG. 4. The characteristic peaks for porphyrin intermediate TPP—NH-Pip 5 (FIG. 4A) are illustrated as N—H stretching in the region 3310-3450 $cm^{-1}$ and with aromatic and aliphatic C—H stretching at 3022 and 2816 $cm^{-1}$. Peaks at 1691 and 1595 $cm^{-1}$ are consistent with the amide bonds and three strong peaks at 966, 799 and 700 $cm^{-1}$ are characteristic for the TPP ring system (shown by arrows).

The main characteristic peak in the BrA-DiTBDMS-CS intermediate 9 is observed at 2858-2957 $cm^{-1}$ showing C—H stretching of Si—$CH_3$, the amide peaks at 1682 and 1530 $cm^{-1}$. Also, peaks at 836 and 777 $cm^{-1}$ represents Si—C stretching and $CH_3$ rocking (These last two peaks are indicated by arrows in FIG. 4B).

The appearance of characteristic TPP peaks in the spectra of intermediate $TPPp_{0.1}$-$BrA_{0.9}$-DiTBDMS-CS 10A (FIG. 4C) confirms the covalent attachment of porphyrin (TPP—NH-Pip 5) to chitosan (9). There was no marked change observed in the spectra when this was converted to crude $TPPp_{0.1}$-DiTBDMS-CS-$MP_{0.9}$14A. However, the final TBDMS deprotection of the material to give $TPPp_{0.1}$-CS-$MP_{0.9}$ 18A is clearly indicated by the absence of the characteristic Si—$CH_3$ peaks and the appearance of the broad O—H peak, whereas characteristic TPP peaks remain intact (FIG. 4E).

Figure 5:
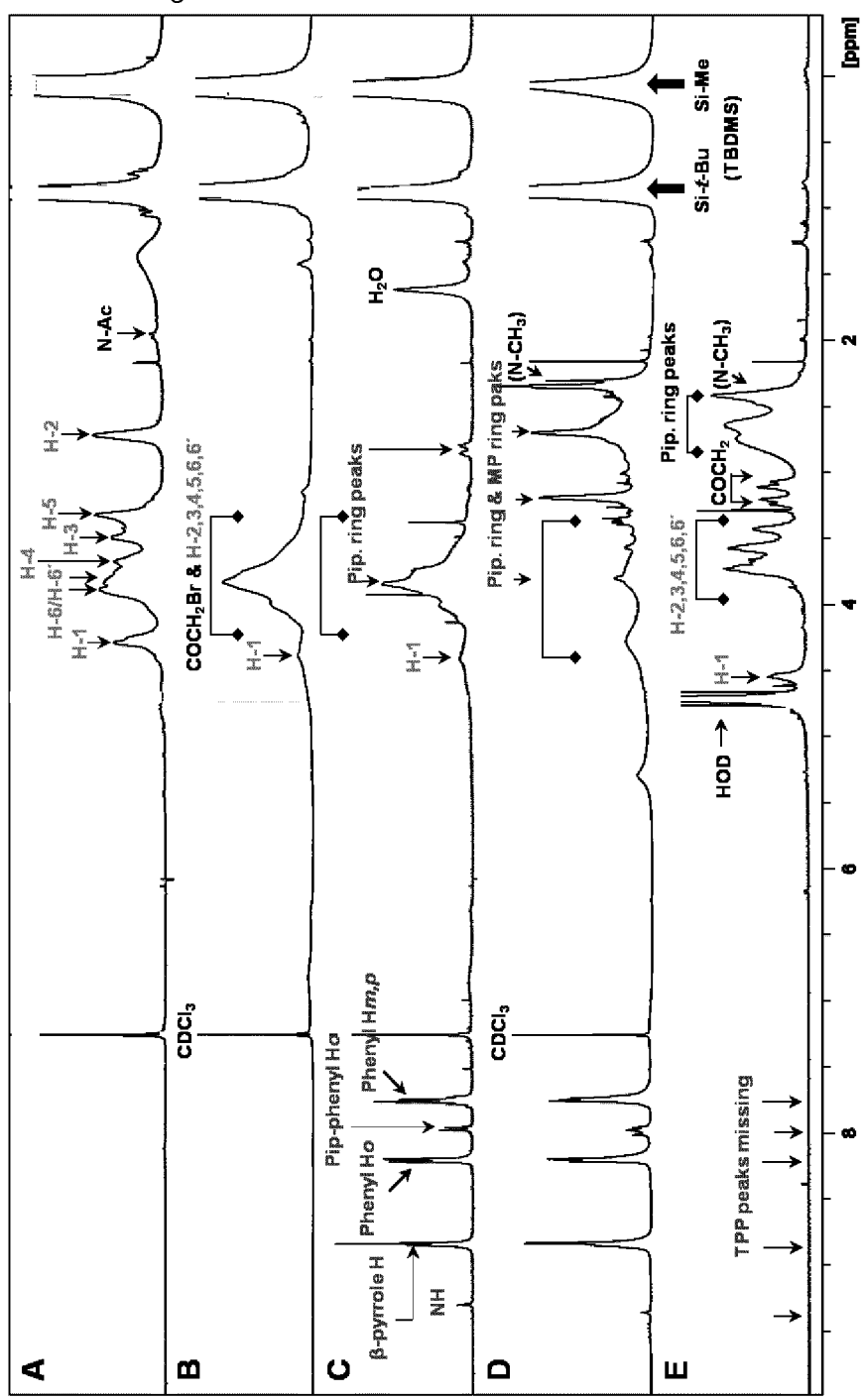
FIG. 5 shows representative $^1$H NMR spectra overlay of all of the intermediates and the final compound in the synthesis of TPPp$_{0.1}$-CS-MP$_{0.9}$ (18A): (A) DiTBDMS-C 8; (B) BrA-DiTBDMS-C 9; (C) TPPp$_{0.1}$-CH$_2$CO-DiTBDMS-C 10A; (D) TPPp$_{0.1}$-DiTBDMS-CS-MP$_{0.9}$ 14A; (E) TPPp$_{0.1}$-CS-MP$_{0.9}$ 18A.

$^1H$ and $^{13}C$ (Solid State) Nuclear Magnetic Resonance Spectroscopy (NMR) analysis:

$^1H$ NMR Analysis:

The representative example of the overlay of the $^1H$ NMR spectra of all intermediates and the final product in the synthesis of $TPP_{0.1}$—CS-$MP_{0.9}$ 18A is shown in FIG. 5. After TBDMS protection, the material (DiTBDMS-CS 8) becomes cleanly soluble in $CDCl_3$ and also shows well resolved peaks (FIG. 5A) of each proton in the chitosan backbone. Peaks at 0.90-0.89 (br s) and 0.13-0.05 (br s) can be assigned to $(CH_3)_3C$—Si and $(CH3)_2Si$ respectively.

Bromoacetylation of DiTBDMS-CS to give BrA-DiTBDMS-CS 9 is marked by a downfield shift of the H-2 (GluN) peak. Also, all chitosan backbone peaks H-1 to H-6 along with $COCH_2Br$ peaks come together at 4.40-3.26 ppm, while TBDMS peaks show no significant change in their positions (FIG. 5B).

The $^1H$ NMR spectra of the $TPPp_{0.1}$-$BrA_{0.9}$-DiTBDMS-CS 10A intermediate (FIG. 5C) confirms the characteristic peaks of the TPP moiety can be seen in the aromatic region and also a peak at −2.7 [not shown in FIG. 5C], which is typically associated with the two pyrrolic inner amine protons in the core of the free base porphyrin, could also be identified. In addition one of the distinct peaks that can be assigned to the half of the cyclic —$CH_2$ group of the piperazine moiety can be observed at 2.81-2.86 (m) ppm, and the remaining cyclic —$CH_2$ group of the piperazine falls under the broad region (3.3-4.5 ppm) of the chitosan moiety.

In the $TPPp_{0.1}$-DiTBDMS-CS-$MP_{0.9}$ 14A spectra, new peaks for N—$CH_3$ of the 1-methylpiperazine moiety (FIG. 5D) were observed. Purification was not done at this stage and the spectrum thus shows excess 1-methyl piperazine.

Figure 6:
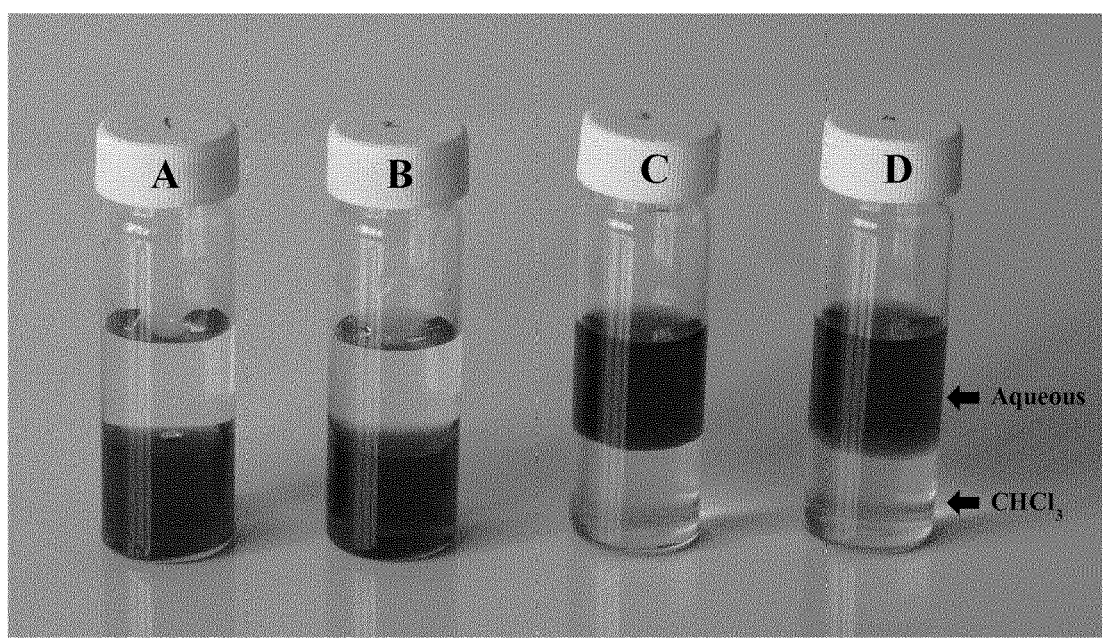
FIG. 6 shows partitioning of compounds dissolved in Aqueous:CHCl$_3$ two phase system. (A) TPP(p-NH$_2$)$_1$3 (B) TPPNH-Pip 5 (C) TPPp$_{0.25}$-CS-TMA$_{0.75}$ 17A (D) TPPp$_{0.25}$-CS-MP$_{0.75}$ 19A. Aqueous phases are shown on top.

After the final deprotection step a material with excellent aqueous solubility was obtained. In the $^1H$ NMR spectra of final compound $TPPp_{0.1}$-CS-$MP_{0.9}$ 18A all peaks of the chitosan backbone along with the 1-methyl piperazine peaks can be clearly identified; however there is no observable NMR signal of the TPP moiety (FIG. 5E). The same results were observed for all deprotected final compounds (17A-19B). In $d_6$-DMSO the TPP peaks could be observed but in this case the chitosan backbone peaks were broadened and not clearly identifiable. The solubility of the carrier was also poor in this solvent and it was found that the best results could be obtained with a mixture of these two solvents (see later discussion). The $TPPp_{0.1}$-CS-$MP_{0.9}$ 18A has a dark red color confirming the presence of the PS. A partitioning experiment showed that the highly lipophilic PS moieties TPP—$NH_2$ and TPP—NH-Pip did not partition into the aqueous phase in a two-phase $H_2O/CHCl_3$ system (FIG. 6) whereas, the final (polar) TPP—CS-TMA and TPP—CS-MP carriers are highly polar. They were fully solubilized in the aqueous phase and did not partition into the organic phase.

Figure 7:
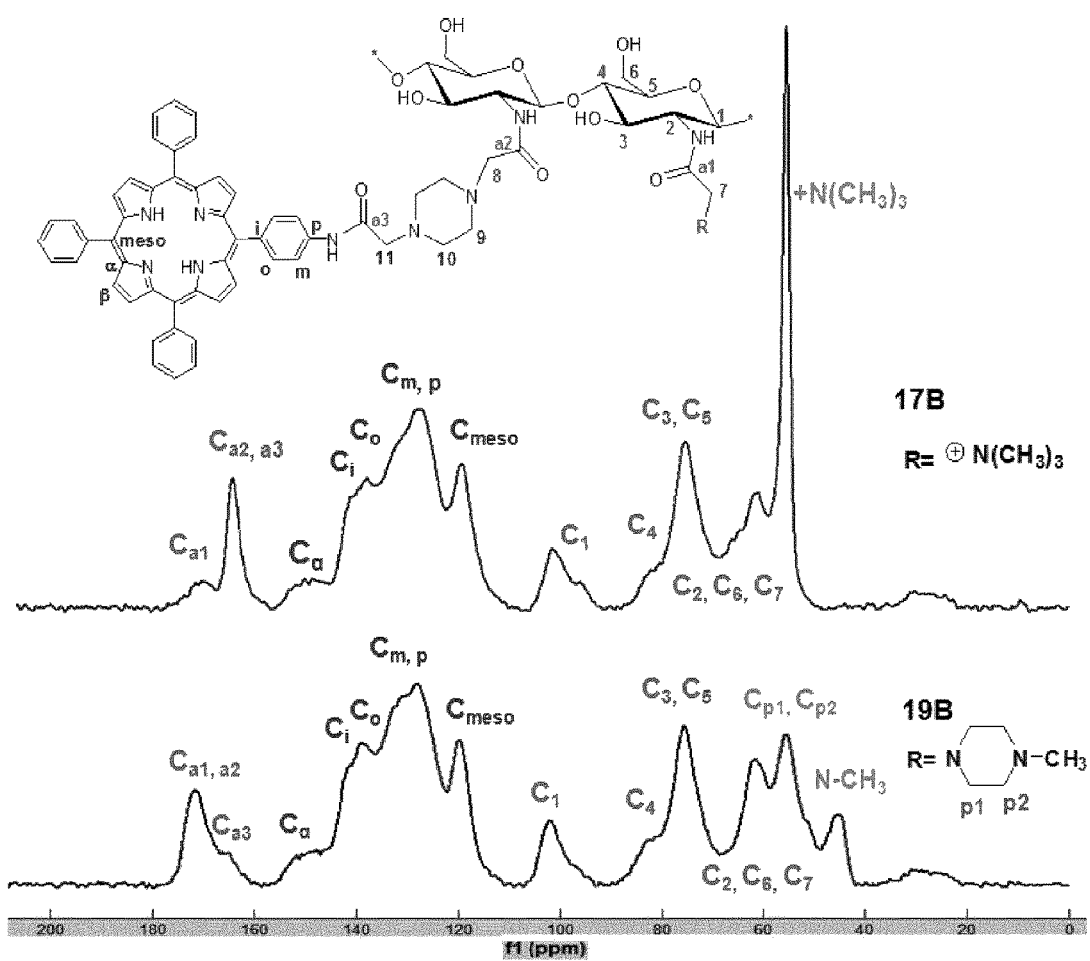
FIG. 7 shows solid state $^{13}$C NMR spectra of the representative final compounds of TPPp$_{0.25}$-CS-TMA$_{0.75}$ (17B) & TPPp$_{0.25}$-CS-MP$_{0.75}$ (19B).

Solid State $^{13}C$ NMR analysis:

The carbon peaks of final carriers could be observed in solid state NMR (FIG. 7). The C2-C6 carbons of the glucosamine and the CO$\underline{C}H_2$ carbon are observed in the 60-80 ppm range and the C1 peak is clearly resolved at ~102 ppm. The peaks between 115-155 ppm can be assigned as Cmeso (~119), Cm, p (~128), $C_β$(~131), Co (~138), Ci (~140) and Cα (~150) of the TPP moiety and this assignment is fully comparable to the solution state $^{13}C$ NMR spectra of TPP—NH-Pip 5. The carbonyl (CS—NH—C═O and TPP—NH—C═O) appears at 160-169 ppm. In the N-(2-(N,N,N-trimethylammoniumyl) acetyl) derivative $TPPp_{0.25}$-CS-$TMA_{0.75}$ (17B) the quaternary methyl carbons ($^+N(CH_3)_3$) can be observed as an intense peak at 55.5 ppm. In the N-methyl-piperazinyl derivative $TPPp_{0.25}$-CS-$MP_{0.75}$ (19B) the methyl carbon (N—$CH_3$) can be observed at 45 ppm and the cyclic methylene (—$CH_2$—N) carbons are merged with the glucosamine signals in the 50-55 ppm region. The solid state $^{13}C$ NMR was therefore consistent with the carriers with a covalently linked PS.

Degree of Substitution (DS) and Conversion Efficiency.

Table 1 below shows the DS for the final carrier compounds. The aim was to control the DS with an equivalent ratio between compounds 5 and 9 in reaction step "e" (Scheme 2 in FIG. 3). The final DS matches the target value based on the equivalence in the reaction (0.1 or 0.25) within a 2% margin and indicating 100% efficiency in the reaction. Previously, covalent linking various lipophilic moieties to chitosan has been investigated. This includes drugs like doxorubicin and paclitaxel; endogenous biomolecules like 5α-Cholanic acid, 5β-Cholanic acid, deoxycholic acid and cholesterol and photosensitizers like chlorine e6 (Ce6) and protoporphyrin IX (PpIX). In most cases the DS is significantly less than we report here for highly lipophilic TPP.

Previous investigators also observed that the conjugation efficiency will decrease significantly as the degree of substitution increases. The current process has the advantage that it uses protected chitosan which is highly soluble in organic solvents and can therefore be efficiently combined with a lipophilic PS moiety under mild conditions. Excellent reproducibility of the reaction is also confirmed, as DS in the two batches (A and B) match within the same 2% margin.

TABLE 1

Degree of substitution (DS) for the TPP modified chitosan carriers 16A-19B

| Entry | Chitosan Derivatives | Compound | TPP-NH-Pip (eq. per sugar unit used) | DS* (linked TPP moieties per sugar unit) |
|---|---|---|---|---|
| 1. | $TPPp_{0.1}$-CS-$TMA_{0.9}$ | 16A | 0.10 | 0.10 |
| 2. | $TPPp_{0.1}$-CS-$TMA_{0.9}$ | 16B | 0.10 | 0.10 |
| 3. | $TPPp_{0.25}$-CS-$TMA_{0.75}$ | 17A | 0.25 | 0.23 |
| 4. | $TPPp_{0.25}$-CS-$TMA_{0.75}$ | 17B | 0.25 | 0.25 |
| 5. | $TPPp_{0.1}$-CS-$MP_{0.9}$ | 18A | 0.10 | 0.09 |
| 6. | $TPPp_{0.1}$-CS-$MP_{0.9}$ | 18B | 0.10 | 0.10 |
| 7. | $TPPp_{0.25}$-CS-$MP_{0.75}$ | 19A | 0.25 | 0.25 |
| 8. | $TPPp_{0.25}$-CS-$MP_{0.75}$ | 19B | 0.25 | 0.25 |

*DS determined by $^1$H NMR

Analysis of the Self Aggregation of Carriers to Form Nanoparticles and Unfolding of Carrier Nanopaticles.

Aromatic porphyrins can form π-π stacking systems which are defined as J (red-shifted) or H (blue-shifted) type aggregates. Peripheral substituent groups can contribute to aggregation mechanisms. This aggregation can be observed by NMR, UV-Vis and Fluorescence spectroscopy. Thus, extreme broadening of peaks and loss of peaks in $^1$H NMR has been reported for carboxyphenyl-porphyrin (TCPP) aggregates, p-sulfonatophenyl and phenyl meso-substituted porphyrins and three kinds of cationic porphyrins (TOPyP, TMPyP and APP). Similar observations of loss of signal due to immobilization have been made in dispersion copolymerization of lipophilic n-butylmethancrylate with a poly(ethylene oxide) macro monomer.

In the current work the lack of peaks in the aromatic region, in the $^1$H NMR in $D_2O$ of final compounds 16A-19B suggested aggregation of the TPP moieties in the $D_2O$ due to t-π stacking and hydrophobic interaction. NMR study of the representative $TPPp_{0.1}$-CS-$TMA_{0.9}$ 16B compound, in a DMSO-$d_6$: $D_2O$ mixture, is shown in FIG. 8. In pure $D_2O$ TPP moiety peaks are missing and only very weak peaks are observed in the aromatic region in DMSO-$d_6$: $D_2O$ (25:75) mixture while chitosan backbone peaks can be observed. When the DMSO-$d_6$ content is further increased to DMSO-$d_6$: $D_2O$ (50:50), broad peaks can be observed (FIG. 8IC). The relative intensity of the aromatic peaks increases as the DMSO-$d_6$ content increases in the mixture and in almost pure $d_6$-DMSO (only 2% $D_2O$ v/v), the aromatic TPP peaks are clearly visible along with the H-1 and remaining chitosan-backbone peaks and the $^+NMe_3$ peak (FIG. 8IA). This also suggests that the carrier is fully unfolded under these conditions. This interpretation was further supported by UV-Vis and fluorescence studies (FIG. 8).

The nanocarriers dissolved in water show a broad Soret band for the π-π stacked photosensitizer with an absorption maxima at 417 nm (FIG. 8II). This peak becomes gradually sharper and slightly shifted (to 420 nm in 100% DMSO) when DMSO concentration increased and the structure unfolds.

In pure water the fluorescence is almost fully quenched which is also consistent with aggregation of the photosensitizer moieties. The fluorescence intensity dramatically increases but as DMSO content increased to 50% there is a sharp increase in the fluorescence intensity with further gradual increase to 100% DMSO concentration observed (FIG. 8III).

An attempt was made to further characterize the nanocarrier particles by scanning electron microscopy. Droplets of nanocarrier solution were pipetted onto a silicone wafer surface and allowed to dry (FIG. 9A,B) by SEM. In some samples, nanoparticles with a size dispersion in the 10-200 nm could be observed, either isolated (FIG. 9A), clustered or crystallizing into dendrite structures (FIG. 9B), similar to that typically observed when drying nanoparticle suspensions. In order to avoid particle aggregation, spin coating of the samples was tried but in this case featureless film and few particles were observed. The film thickness after spin coating was estimated to be significantly smaller than 10 nm by spectroscopic ellipsometry. The maximum thickness of layers formed after drying of solutions on the surface, however, was measured to be of the order of 100 nm. Water contact angle measurement revealed a relatively hydrophobic film surface and that hydrophobicity of the film was dependent on the concentration of the applied carrier sample (FIG. 9C). These results are consistent with dynamic nanoparticles that unfold when coated, and that the hydrophilic polymer backbone will adhere to the polar silicone dioxide surface exposing the hydrophobic photosensitizer moieties from the particle core.

Nanoparticle aggregation and physical instability leading to formation of insoluble aggregates is commonly observed. Physical stability of a 1 mg/ml aqueous solution of $TPPp_{0.25}$-CS-$MP_{0.75}$ (17A) was monitored over a period of three months. No precipitation of this compound was observed.

Fluorescence Quantum Yields.

Herein, the fluorescence quantum yields of $TPP(p-NH_2)_1$, TPP—NH-Pip and chitosan derivatives of TPP (16A-19B) were investigated in DMSO (excited at 419 nm). The quantum yield of $TPP(p-NH_2)_1$ was less than that of its derivative TPP—NH-Pip as well as TPP—CS-TMA & TPP—CS-MP derivatives. This demonstrated a high degree of excited state quenching of $TPP(p-NH_2)_1$ as compared to its derivatives. $\phi_F$ is almost equal for all carrier compounds (16A-19B) with a minor fluctuation±0.004 around the value obtained for the intermediate TPP—NH-Pip.

However, $\phi_F$ values of $TPP(p-NH_2)_1$ (0.0002) are lower as compared to some literature published data. Bhaumik et.al. (*J Org Chem* 2009, 74:5894) reported it as 0.05 when excited at 418 nm in DMF. They reported fluorescence emission maxima at 664 nm which is different from our current finding of 650 nm. TPP was used as a standard, whereas we used anthracene as the standard. Low $\phi_F$ in the current work may be due to self-association of the photosensitizers. Table 2 below shows the Fluorescence quantum yield ($\phi_F$) of TPP modified chitosan carriers 16A-19B.

TABLE 2

| Entry | Chitosan Derivatives | Compound | $\lambda_{abs}$* (nm) | $\lambda_{em}$* (nm) | Quantum Yield ($\phi_F$) |
|---|---|---|---|---|---|
| 1. | $TPP(p-NH_2)_1$ | 3 | 419 | 651 | 0.0002 |
| 2. | TPP-NH-Pip | 5 | 419 | 651 | 0.0036 |
| 3. | $TPPp_{0.1}$-CS-$TMA_{0.9}$ | 16A | 419 | 651 | 0.0032 |
| 4. | $TPPp_{0.1}$-CS-$TMA_{0.9}$ | 16B | 419 | 651 | 0.0034 |
| 5. | $TPPp_{0.25}$-CS-$TMA_{0.75}$ | 17A | 419 | 651 | 0.0036 |

TABLE 2-continued

| Entry | Chitosan Derivatives | Compound | $\lambda_{abs}$* (nm) | $\lambda_{em}$* (nm) | Quantum Yield ($\phi_F$) |
|---|---|---|---|---|---|
| 6. | $TPPp_{0.25}$-CS-$TMA_{0.75}$ | 17B | 419 | 651 | 0.0032 |
| 7. | $TPPp_{0.1}$-CS-$MP_{0.9}$ | 18A | 419 | 651 | 0.0036 |
| 8. | $TPPp_{0.1}$-CS-$MP_{0.9}$ | 18B | 419 | 651 | 0.0033 |
| 9. | $TPPp_{0.25}$-CS-$MP_{0.75}$ | 19A | 419 | 651 | 0.0036 |
| 10. | $TPPp_{0.25}$-CS-$MP_{0.75}$ | 19B | 419 | 651 | 0.0033 |

*All data collected in DMSO at room temperature
λ-wavelength

Conclusion

We have shown that DiTBDMS chitosan can be used for highly efficient synthesis of meso-Tetraphenylporphyrin tethered chitosan based nano-carriers. The synthesis of these carriers was fully reproducible and the method allowed precise control of the degree of substitution for highly lipophilic photosensitizer. The NMR, florescence, and UV-Vis studies were consistent with self-association of the photosensitizer moieties. The carriers are polar and show good aqueous solubility and physical stability. In DMSO the photosensitizer dissociates from the self-association and therefore become fluorescent. In aqueous solution the carriers will assemble into nanoparticle-like structures with the cationic group and polymer backbone forming an outer shell around a core composed of the aggregated (t-t stacked) lipophilic TPP moieties. The cationic groups and polymer backbone have relatively free movement in the liquid and can therefore be observed by NMR. In contrast the TPP core is semi-solid with very limited movement and can therefore only be detected in solid state NMR. This structure is in dynamic equilibrium with the unfolded, and fluorescent, form which becomes dominant in DMSO allowing detection of the TPP by NMR. When the carrier is in contact with the cell or the endocytic membrane, the structure unfolds and lipophilic moieties are inserted into the endocytic membrane allowing for the excitation and photosensitization which leads to PDT and PCI effects.

Example 2—Synthesis of TPC-Chitosan-Based Nanocarriers

General Materials and Methods were as for Example 1, where appropriate.
Synthesis
See scheme 3 in FIG. 10 for synthesis of TPC—NH-Pip
Meso-Tetraphenylporphyrin (1).

Compound 1 (TPP) was prepared by the procedure described in *Journal of Organic Chemistry* 1967, 32, 476.
5-(4-Aminophenyl)-10,15,20-triphenylporphyrin [TPP(p-$NH_2$)$_1$] (3).

Compound 3 was prepared following the literature procedure in *Tetrahedron* 2004, 60, 2757.
5-(4-Aminophenyl)-10,15,20-triphenylchlorin: TPC(p-$NH_2$)$_1$ (20).

Compound 3 (1.5 g, 2.38 mmol) was dissolved in pyridine under $N_2$ and dark atmosphere. $K_2CO_3$ 2.96 g, 21.5 mmol) and p-toluenesulfonylhydrazide (0.887 g, 4.77 mmol) were added and the resulting reaction mixture was heated to reflux temperature. Further quantities of p-toluenesulfonylhydrazide (0.887 g, 4.77 mmol) were added after an interval of 2, 4, 6 and 8 h. Stirring was continued at reflux temperature for 24 h. The reaction mixture was added to a 1:1 mixture of EtOAc:$H_2O$ (2:1, 900 mL) and refluxed for 1 h. After cooling to room temperature, the organic phase was separated and washed with 2N HCl (3×200 mL) followed by washing with water (2×100 mL) and saturated aqueous $NaHCO_3$ (2×150 mL) The organic phase was then dried over $Na_2SO_4$ and concentrated in vacuo to afford a 1.3 g crude mixture. Analysis of the visible spectrum of crude product showed it to be a mixture of chlorine and bacterochlorin (band at 651 and 738 respectively). Also, analysis by $^1H$ NMR spectra showed that there was no trace amount of the starting porphyrin material left.

Crude material (1.3 g) (chlorine/bacterochlorin mixture) obtained from the above reaction step was dissolved in $CH_2Cl_2$ (100 mL). ortho-Chloranil (420 mg, 2.7 mmol) was then added in one portion to the stirring organic solution at room temperature and the progress of the reaction was simultaneously monitored by UV-vis. Immediately after the peak of bacterochlorin (738 nm) was completely diminished, the reaction mixture was washed with 5% aqueous sodium bisulfite (2×125 mL), followed by washing with water (100 mL), 5% NaOH (2×150 mL), and finally with water (150 mL). The organic phase was then dried over $Na_2SO_4$ and concentrated in vacuo to afford exclusively the titled chlorin compound 20 (1.2 g, 80%) as a brown colour solid. Compound 3 seems to be exists in more than one isomer. TLC (Hexane/$CH_2Cl_2$ 3:7): Rf=0.23, $^1H$ NMR (CDCl$_3$): δ=7.86-8.66 (m, 14H, β-pyrrole-H & phenyl-Ho), 7.63-7.73 (m, 9H, triphenyl-Hm,p), 7.00 (d, J=8 Hz, 2H, $NH_2$-phenyl-Hm), 4.14-4.23 (m, 4H, chlorin β-pyrrole-$CH_2$), 3.95 (br s, 2H, $NH_2$), −1.38 and −1.46 (br s, 2H, α-pyrrole-NH) ppm; MS (ESI): m/z calcd. for $C_{44}H_{34}N_5$ ([M+H]$^+$) 632.2809, found 632.2792.; UV-vis (DMSO): $\lambda_{max}$: 422, 524, 553, 600, 652 nm.

Synthesis of intermediate TPC—NH-pip (21).

The compound 20 (600 mg, 0.95 mmol) was dissolved in $CH_2Cl_2$ (15 mL) and stirred under an $N_2$ atmosphere. Et$_3$N (0.32 mL, 2.27 mmol) was added followed by dropwise addition of chloroacetyl chloride (0.092 mL, 1.15 mmol) at room temperature and continued stirring at room temperature. After 2 h in situ an excess amount of piperazine (0.328 g, 3.8 mmol) was added and stirring was continued overnight. The reaction mixture was diluted with $CH_2Cl_2$ (85 mL), extracted, washed with water (3×35 mL), brine (35 mL), dried over $Na_2SO_4$, filtered and concentrated in vacuo. Crude product was then purified by silica gel column chromatography. The desired product was isolated in MeOH: $CH_2Cl_2$ (8:92) as eluent to afford the titled intermediate 21 (440 mg, 61%) as a brown solid.

TLC ($CH_2Cl_2$: MeOH, 9:1): $R_f$=0.15; $^1H$ NMR (CDCl$_3$): δ=9.34, 9.39 (s, 1H, TPC—NH), 7.86-8.65 (m, 16H, β-pyrrole-H, phenyl-Ho & R-NHTPC-phenyl-Ho,m), 7.66-7.73 (m, 9H, triphenyl-Hm,p), 4.18-4.19 (br s, 4H, chlorin β-pyrrole-$CH_2$), 3.30 (s, 2H, ArNHCO$CH_2$-pip), 3.17 (br m, 4H, piperazine ring-$CH_2$), 2.81 (br m, 4H, piperazine ring-$CH_2$), −1.37 (br s, 2H, α-pyrrole-NH); $^{13}C$ NMR (CDCl$_3$): δ=168.37, 167.48, 152.61, 143.14, 142.22, 140.86, 139.20, 138.32, 137.19, 136.99, 135.33, 134.64, 133.98, 133.01, 132.37, 132.12, 131.96, 128.17, 127.69, 126.81, 123.56, 123.38, 122.79, 122.08, 119.22, 117.94, 112.41, 111.65, 62.63, 53.50, 45.59, 35.90 ppm; UV-vis (DMSO): $\lambda_{max}$: 421, 521, 549, 598, 651 nm.

See scheme 4 in FIG. 11
Synthesis of tert-Butyl piperazine-1-carboxylate (22).

Piperazine (6 g, 69.6 mmol) was dissolved in $CH_2Cl_2$ (120 mL). The solution was cooled to 0° C. and Boc$_2$O (7.6 g, 34.8 mmol) in $CH_2Cl_2$ (80 mL) was added dropwise. The reaction mixture was allowed to warm to room temperature and stirring was continued for 24 h. The precipitate was filtered off and washed with $CH_2Cl_2$ (2×20 mL) and the combined filtrate was separated and washed with water (3×40 mL), brine (30 mL) and dried over Na$_2$SO$_4$ and concentrated in vacuo to afford the titled compound 22 (6.5 g, 50%) as a white solid.

Mp 44-46° C. (lit. mp 46-47° C.); $^1$H NMR (CDCl3): δ=3.32 (t, J=4 Hz, 4H), 2.74 (t, J=4 Hz, 4H), 1.39 (s, 9H); $^{13}$C NMR (CDCl$_3$): δ=154.85, 80.00, 79.52, 45.96, 44.45, 28.45 ppm; MS (ESI): m/z calcd. for C$_9$H$_{19}$N$_2$O$_2$ ([M+H]$^+$) 187.1441 found 187.1412.

Synthesis of p-(Methoxycarbonyl)benzaldehyde (23).

4-Carboxybenzaldehyde (4 g, 26.6 mmol) was suspended in 60 mL of anhydrous MeOH and stirred under N$_2$. The reaction mixture was cooled to 0° C. and acetyl chloride (9.5 mL, 133 mmol) was added dropwise. The reaction mixture was stirred for 12 h at room temperature. The MeOH was removed in vacuo, and the crude mixture was diluted with EtOAc (120 mL). The organic phase was washed with aqueous 1N NaOH (5×30 mL) and brine (2×25 mL), dried over Na$_2$SO$_4$, filtered and concentrated in vacuo. Crude solid was then recrystallised by using EtOAc and Petroleum ether to afford ester 23 (3.8 g, 87%) as a white solid.

TLC (Hexane: CH$_2$Cl$_2$ 3:7): R$_f$=0.36; Mp: 61-63° C. (lit. mp 59-64° C.); $^1$H NMR (CDCl$_3$): δ=10.06 (s, 1H, CHO), 8.15 (d, J=8.4 Hz, 2H), 7.91 (d, J=8.4 Hz, 2H), 3.92 (s, 3H) ppm; $^{13}$C NMR (CDCl$_3$): δ=191.66, 166.07, 139.21, 135.13, 130.23, 129.55, 52.62 ppm.

Synthesis of 5-(4-Methoxycarbonylphenyl)-10,15,20-triphenylporphyrin TPP(p-CO$_2$Me)$_1$ (24).

Following the literature method, (*J. Am. Chem. Soc.* 2008, 130, 4236-4237).

Synthesis of 5-(4-Carboxyphenyl)-10,15,20-triphenylporphyrin TPP(p-CO$_2$H)$_1$ (25)

Compound 24 (1.2 g, 1.78 mmol) was dissolved in a mixture of THF: Pyridine (10:1, 100 mL). 2N methanolic KOH (120 mL) was added and the reaction mixture was refluxed for 24 h. Then the reaction mixture was cooled down to room temperature and neutralized with saturated aqueous citric acid solution. Subsequently the reaction mixture was concentrated in vacuo until removal of MeOH and THF as completed. The crude mixture was then diluted with CH$_2$Cl$_2$ (150 mL) and water (120 mL) and the aqueous phase was extracted with CH$_2$Cl$_2$ (3×50 mL). The combined organic phase was washed with water (2×40 mL) and brine (35 mL), dried over Na$_2$SO$_4$ and concentrated in vacuo. The crude mixture was purified by silica gel column chromatography using MeOH: CH$_2$Cl$_2$ (100:0 to 96:4 as eluent) to afford the title acid 25 (0.83 g, 71%) as a purple solid.

TLC (CH$_2$Cl$_2$: MeOH 95:5): R$_f$=0.54; $^1$H NMR (DMSO-d$_6$): δ=8.84 (br s, 8H, β-pyrrole-H), 8.33-8.39 (m, 4H, R—COTPP-phenyl-Ho,m), 8.21-8.23 (m, 6H, triphenyl-Ho), 7.81-7.88 (m, 9H, triphenyl-Hm,p), −2.92 (s, 2H, NH) ppm; MS (ESI): m/z calcd. for C$_{45}$H$_{31}$N$_4$O$_2$ ([M+H]$^+$) 659.2442, found 659.2420.

Synthesis of 5-(4-Carboxyphenyl)-10,15,20-triphenylchlorin TPC(p-CO$_2$H)$_1$ (26)

Compound 25 (600 mg, 0.9 mmol) and anhydrous K$_2$CO$_3$ (1.13 g, 8.2 mmol) was dissolved in pyridine (42 mL) under N$_2$ and dark atmosphere. Toluene-4-sulfonylhydrazide (340 mg, 1.8 mmol) was then added and the mixture was stirred at reflux temperature. Further quantities of toluene-4-sulfonylhydrazide (340 mg, 1.8 mmol) in 3 mL of pyridine were added after an interval of 2, 4, 6, 8 and 10 h reaction. The stirring was continued at reflux temperature for 24 h. After cooling to room temperature, EtOAc (500 mL) and deionised H$_2$O (250 mL) were added and the reaction mixture was again refluxed for 1 h. After cooling to room temperature, the organic phase was separated and washed with 2N HCl (2×150 mL) and then with water (2×150 mL), dried over Na$_2$SO$_4$ and concentrated in vacuo to afford 565 mg of the crude mixture. Analysis of the visible spectrum of crude product showed it to be a mixture of chlorin and bacterochlorin (band at 651 and 738 respectively). Also, analysis by $^1$H NMR spectra showed that there was no trace amount of starting porphyrin material left.

Crude material (chlorin/bacterochlorin mixture, 565 mg) obtained from the above reaction step, was completely dissolved in a mixture of CH$_2$Cl$_2$: MeOH (75:25). ortho-Chloranil (180 mg, 0.7 mmol) was then added in one portion to the stirred organic solution at room temperature and the progress of the reaction was simultaneously monitored by UV-Vis. Immediately after the absorption peak of bacterochlorin (738 nm) diminished, the organic phase was washed with 5% aqueous sodium bisulfite solution (2×150 mL), followed by washing with water (100 mL), then by 5% aqueous NaOH (2×150 mL) and finally with water (120 mL). If an emulsion was observed the organic phase was washed with saturated aqueous citric acid solution. The organic phase was dried over Na$_2$SO$_4$, filtered and concentrated in vacuo to afford exclusively the titled chlorin compound 26 (420 mg, 70%) as a brown solid. Compound 9 is present in more than one isomer.

TLC (CH$_2$Cl$_2$: MeOH, 95:5): R$_f$=0.54, $^1$H NMR (DMSO-d$_6$): δ=7.91-8.58 (m, 16H, β-pyrrole-H, phenyl-Ho & R—COTPC-phenyl-Ho,m), 7.68-7.77 (m, 9H, triphenyl-Hm,p), 4.12-4.13 (m, 4H, chlorin β-pyrrole-CH$_2$), −1.53 and −1.60 (2 brs, 2H, α-pyrrole-NH); $^1$H NMR (CDCl$_3$): δ=7.87-8.60 (m, 16H, β-pyrrole-H, phenyl-Ho & R—COTPC-phenyl-Ho,m), 7.64-7.74 (m, 9H, triphenyl-Hm,p), 4.16-4.18 (m, 4H, chlorin β-pyrrole-CH$_2$), −1.39 and −1.49 (2 br s, 2H, α-pyrrole-NH) ppm; MS (ESI) calcd. for C$_{45}$H$_{33}$N$_4$O$_2$ ([M+H]$^+$) 661.2598, found 661.2566; UV-vis (DMSO): λ$_{max}$: 420, 520, 547, 599, 651 nm.

Synthesis of intermediate tert-Butyl N-[piperazine-1-carboxylate]-5-(4-carboxyphenyl)-10,15,20-triphenylchlorin (27).

Chlorin compound 26 (500 mg, 0.76 mmol) and tert-butyl piperazine-1-carboxylate 22 (155 mg, 0.83 mmol) was dissolved in DMF (4 mL) under N$_2$ and in the dark. To the reaction mixture, EDCI-HCl (174 mg, 0.91 mmol) and HOBT (123 mg, 0.91 mmol) were added followed by addition of Et$_3$N (0.26 mL, 1.82 mmol) at room temperature. The reaction mixture was then stirred overnight at room temperature before it was slowly poured into stirring water (100 mL). The solid material was filtered off, washed with plenty of water, and dried well. The crude product was purified by silica gel column chromatography (CH$_2$Cl$_2$: MeOH 100:0 to 99:1) to afford titled amide compound 27 (340 mg, 54%) as a brown solid.

TLC (CH$_2$Cl$_2$: MeOH 99:1): Rf=0.74; $^1$H NMR (CDCl$_3$): δ=7.74-8.59 (m, 16H, β-pyrrole-H, phenyl-Ho & R—COTPC-phenyl-Ho,m), 7.65-7.72 (m, 9H, triphenyl-Hm,p), 4.16-4.17 (m, 4H, chlorin β-pyrrole-CH$_2$), 3.78-3.86 (br m, 4H, piperazine ring-CH$_2$), 3.63 (br m, 4H, piperazine ring-CH$_2$), 1.53 (s, 9H, boc-(CH$_3$)$_3$), −1.39 and −1.47 (2 brs, 2H, α-pyrrole-NH) ppm.

Synthesis of intermediate TPC—CO-pip (28).

The compound 27 (320 mg, 0.39 mmol) was dissolved in CH$_2$Cl$_2$ (8 mL) under N$_2$ in the dark. CH$_2$Cl$_2$: TFA (1:1, 4 mL) was added and stirred at rt for 1 h. The reaction mixture was diluted with CH$_2$Cl$_2$ (40 mL) and washed with water (2×15 mL), saturated aqueous NaHCO$_3$ (2×15 mL) and brine (15 mL). The organic layer was dried over Na$_2$SO$_4$ and concentrated in vacuo. The crude product was then purified by silica gel column chromatography (CH2Cl$_2$: MeOH 100:0 to 92:8 as eluent) to afford the titled intermediate 28 (250 mg, 89%) as a brown solid.

TLC (CH$_2$Cl$_2$: MeOH, 9:1): R$_f$=0.35, $^1$H NMR (CDCl$_3$): δ=7.74-8.59 (m, 16H, β-pyrrole-H, phenyl-Ho & R—COTPC-phenyl-Ho,m), 7.64-7.72 (m, 9H, triphenyl-Hm,p), 4.16-4.17 (m, 4H, chlorin β-pyrrole-CH$_2$), 3.73-3.90 (br m, 4H, piperazine ring-CH$_2$), 3.04 (br m, 4H, piperazine ring-CH$_2$), −1.40 and −1.47 (2 brs, 2H, α-pyrrole-NH) ppm; MS (ESI) calcd. for C$_{49}$H$_{42}$N$_6$O ([M+2H]$^+$/2) 365.1705, found 365.1707; UV-vis (DMSO): λ$_{max}$: 420, 520, 546, 599, 651 nm.

Chitosan mesylate salt (7).

Synthesized according to our previously published procedure (*Carbohydrate Polymers* 2010, 81:140-144).

N-bromoacetyl-3,6-O-DiTBDMS-CS (BrA-DiTBDMS-CS, 9).

DiTBDMS-CS 8 (1 g, 2.60 mmol) was dissolved in dry CH$_2$Cl$_2$ (15 mL) in a round bottom flask under an N$_2$ atmosphere. The reaction mixture was cooled to −20° C. with an ice/salt mixture. Et3N (1.81 mL, 13 mmol) was added followed by slow dropwise addition of bromoacetyl bromide (0.91 mL, 10 mmol). Stirring was continued for 1 h. The reaction mixture was diluted with CH$_2$Cl$_2$ and concentrated in vacuo. The crude product was stirred in acetonitrile, filtered and washed with fresh acetonitrile. The dry material was dissolved and extracted in CH$_2$Cl$_2$, washed with water and brine, dried over Na$_2$SO$_4$, concentrated in vacuo to afford the titled bromo compound 26 (1.2 g, 92%) as a faint yellow powdered solid.

FT-IR (KBr): v 3402 (br, NH), 2957, 2931, 2886, 2858 (s, C—H TBDMS), 1682 (vs, C=O amide I), 1530 (vs, C=O amide II), 1473, 1391, 1362, 1311, 1259, 1101, 1005, 837, 777 (Si—C), 669 cm$^{-1}$; $^1$H NMR (CDCl$_3$) δ ppm: 4.40 (br s, H-1), 4.02-3.26 (m, H-2 GlcN, H-3, H-4, H-5, H-6, H-6' and 2H GluNH-C=OCH$_2$Br), 0.90 and 0.88 (br s, (CH$_3$)$_3$C—Si), 0.13 and 0.07 (br s, (CH$_3$)$_2$Si) ppm.

See Scheme 6A in FIG. 13

Synthesis of Intermediate 29

(N-TPC—NH-Pip-acetyl)$_{0.1}$-(N-bromoacetyl)$_{0.9}$-DiTBDMS-CS (TPC$_{NP0.1}$-BrA$_{0.9}$-DiTBDMS-CS, 29).

Compound 9 (800 mg, 1.58 mmol) and compound TPC—NH-Pip 21 (120 mg, 0.158 mmol) were dissolved in CH$_2$Cl$_2$ (25 mL) under N$_2$ and in the dark. An exact equimolar quantity of Et$_3$N (22 μL, 0.158 mmol) with respect to 21 was added and the reaction mixture was stirred at rt for 24 h. Total consumption of starting material was confirmed by TLC. The reaction mixture was diluted with CH$_2$Cl$_2$ (55 mL) and washed with water (2×25 mL) and brine (25 mL). The organic phase was dried over Na$_2$SO$_4$, concentrated in vacuo to afford the compound 29 (700 mg, 78%).

$^1$H NMR (CDCl$_3$): δ=9.21, 9.25 (s, TPCNHCO), 7.86-8.60 (m, β-pyrrole-H, phenyl-Ho & R—NHTPC-phenyl-Ho,m), 7.65-7.73 (m, triphenyl-Hm,p), 3.35-4.50 [br m, chitosan (H-1, H-2 GlcN, H-3, H-4, H-5, H-6, H-6' and 2H GluNH-C=O, CH$_2$CONGlc), TPCNHCOCH$_2$-pip, piperazin ring-CH$_2$ and chlorin β-pyrrole-CH$_2$], 2.77-2.83 (m, piperazine ring-CH$_2$), 0.88-0.89 [br s, (CH$_3$)$_3$C—Si], 0.02-0.13 [(br m, (CH$_3$)$_2$Si], −1.44 (br s, 2H, α-pyrrole-NH) ppm.

See Scheme 6B in FIG. 13

Synthesis of Intermediate 34

(N-TPC—CO-Pip-acetyl)$_{0.1}$-(N-bromoacetyl)$_{0.9}$-DiTBDMS-CS (TPC$_{CP0.1}$-BrA$_{0.9}$-DiTBDMS-CS, 34).

Compound 9 (800 mg, 1.58 mmol) was dissolved in NMP (25 mL) under N$_2$ and in the dark. TPC—CO-Pip 28 (125 mg, 0.173 mmol) and NaHCO$_3$ (0.29 g, 3.45 mmol) were added at room temperature. The reaction mixture was then heated at 75° C. and stirred overnight before it was cooled down and poured into stirring water. The solid was filtered off, washed with plenty of water, and dried under suction. The solid obtained was then dissolved in CH$_2$Cl$_2$, filtered and dried over Na$_2$SO$_4$, and the solvent removed in vacuo to afford compound 34 (810 mg, 89%) as a brown solid.

$^1$H NMR (CDCl$_3$): δ=7.75-8.60 (m, β-pyrrole-H, phenyl-Ho & R—COTPC-phenyl-Ho,m), 7.64-7.71 (m, triphenyl-Hm,p), 3.38-4.5 [br m, chitosan (H-1, H-2 GlcN, H-3, H-4, H-5, H-6, H-6' and 2H GluNH—C=O, CH$_2$CONGlc), piperazin ring-CH$_2$ and chlorin β-pyrrole-CH$_2$], 2.76-2.84 (m, piperazin ring-CH$_2$), 0.89-0.92 [br s, (CH$_3$)$_3$C—Si], 0.02-0.10 [(br m, (CH$_3$)$_2$Si)], −1.40 and −1.48 (br s, α-pyrrole-NH) ppm.

General Procedure A for Compounds 30 & 35

(N-TPC—NH-Pip-acetyl)$_{0.1}$-(N—(N,N,N-trimethylammoniumyl)acetyl)$_{0.9}$-DiTBDMS-CS (TPC$_{NP0.1}$-DiTBDMS-CS-TMA$_{0.9}$, 30).

Compound 29 (350 mg, 0.61 mmol) was dissolved in CH$_2$Cl$_2$ (15 mL) under N$_2$ and in the dark. An excess amount of trimethylamine solution was added and the reaction mixture was stirred at rt for 24 h. Solvent was removed in vacuo. The crude product was dried completely under a high vacuum yielding crude product 30 (355 mg, 94%) as a brown solid. The crude compound was used as it was for the next step.

(N-TPC—CO-Pip-acetyl)$_{0.1}$-(N—(N,N,N-trimethylammoniumyl)acetyl)$_{0.9}$-DiTBDMS-CS (TPC$_{PP0.1}$-DiTBDMS-CS-TMA$_{0.9}$, 35).

The general procedure A was followed using 34 (350 mg, 0.61 mol) and trimethylamine solution to give 35 as a crude solid (360 mg, 94%). The crude compound was used as it was for the next step.

General Procedure B for Compounds 31 & 36

(N-TPC—NH-Pip-acetyl)$_{0.1}$-(N—(N-methylpiperazinyl) acetyl)$_{0.9}$-DiTBDMS-CS (TPC$_{NP0.1}$-DiTBDMS-CS-MP$_{0.9}$, 31).

Compound 29 (350 mg, 0.61 mmol) was dissolved in CH$_2$Cl$_2$ (15 mL) under N$_2$ and in the dark. An excess amount of 1-methylpiperazine was added and the reaction mixture was stirred at room temperature for 24 h. Solvent was removed in vacuo. Then crude product was dried completely under a high vacuum yielding corresponding crude product 31 (330, 89%). The crude compound was used as it was for the next step.

(N-TPC—CO-Pip-acetyl)$_{0.1}$-(N—(N-methylpiperazinyl) acetyl)$_{0.9}$-DiTBDMS-CS (TPC$_{CP0.1}$-DiTBDMS-CS-MP$_{0.9}$, 36).

The general procedure B was followed using 34 (250 mg, 0.38 mol) and 1-methylpiperazine to give 36 as a crude solid (265 mg, 93%). The crude compound was used as it was for the next step.

Synthesis of Final Products (32, 33, 37 & 38)

Final deprotection was achieved by following general procedure C:

Compounds (30/31/35/36) were dissolved in MeOH under N$_2$ and in the dark. The reaction mixture was degassed by purging with N$_2$ for 5 minutes and subsequently cooled to 0° C. before addition of 4 mL of conc. HCl. The reaction mixture was allowed to warm to room temperature and stirred for 12 h before it was concentrated completely in vacuo. Crude residue was again dissolved in MeOH and degassed under N$_2$ and in the dark. The reaction mixture was cooled to 0° C. before addition of 2 mL conc. HCl. The reaction mixture was allowed to warm to room temperature and stirred for 12 h. The reaction mixture was then diluted and ion exchanged by addition of 5% aqueous NaCl for 1 h, before it was dialyzed against 8% aqueous NaCl for 24 h and then against deionised water for 3 days. The clean brown solution was subsequently freeze-dried overnight to afford the final products (32/33/37/38 respectively) as a brown fluffy material.

TPC$_{NP0.1}$—CS-TMA$_{0.90}$ (32).

The general procedure C was by followed using 30 (325 mg, 0.52 mmol) and conc.HCl/MeOH to give 32 as a brown solid (175 mg, 85%). $^1$H NMR (DMSO-d$_6$: D$_2$O 98:2): δ=7.83-8.62 (m, β-pyrrole-H, phenyl-Ho & R—NHTPC-phenyl-Ho,m), 7.69-7.77 (m, triphenyl-Hm,p), 4.52 (br s, H-1), 4.11-4.14 (m, —CH$_2$CONGlc and chlorin β-pyrrole-CH$_2$), 3.26-3.67 (br m, partially overlapped with HDO peak, H-2 GlcNAc, H-3, H-4, H-5, H-6, H-6', 2H GluNH-C=O, TPCNHCOCH$_2$-pip, piperazine ring-CH$_2$] 3.24 (s, $^+$N(CH$_3$)$_3$)) ppm; UV-vis (DMSO): λ$_{max}$: 421, 520, 549, 599, 651 nm.

TPC$_{NP0.1}$-CS-MP$_{0.90}$ (33).

The general procedure C was followed using 31 (300 mg, 0.45 mmol) and conc.HCl/MeOH to give 33 (165 mg, 84%) as a brown solid. $^1$H NMR (DMSO-d$_6$: D$_2$O 98:2): δ=7.83-8.62 (m, β-pyrrole-H, phenyl-Ho & R—NHTPC-phenyl-Ho,m), 7.66-7.75 (m, triphenyl-Hm,p), 4.50 (br s, H-1), 4.10-4.14 (m, chlorin β-pyrrole-CH$_2$), 2.92-3.55 (m, partially overlapped with HDO peak, H-2 GlcNAc, H-3, H-4, H-5, H-6, H-6', 2H GluNH-C=O, CH$_2$CONGlc, TPCN-HCOCH$_2$-pip), 2.33-2.63 (m, partially overlapped with DMSO-d6 peak, piperazine ring-CH$_2$, piperazine-N—CH$_3$) ppm; UV-vis (H$_2$O): λ$_{max}$: 412, 430, 531, 560, 611, 664 nm; UV-vis (DMSO): λ$_{max}$: 421, 521, 548, 596, 651 nm.

TPC$_{CP0.1}$—CS-TMA$_{0.90}$ (37).

The general procedure C was followed using 35 (300 mg, 0.48 mmol) and conc.HCl/MeOH to give 37 as a brown solid (170 mg, 89%).

FT-IR (KBr): v 3353, 3061, 2950, 1683, 1580, 1473, 1440, 1376, 1291, 1154, 1112, 1067, 1032, 970, 911, 794, 703 cm$^{-1}$; $^1$H NMR (DMSO-d$_6$: D$_2$O 98:2): δ=7.89-8.62 (m, β-pyrrole-H, phenyl-Ho & R—COTPC-phenyl-Ho,m), 7.67-7.76 (m, triphenyl-Hm,p), 4.50 (br s, H-1), 4.06-4.16 (m, CH$_2$CONGlc and chlorin β-pyrrole-CH$_2$), 3.26-3.75 (m, partially overlapped with HDO peak, H-2 GlcNAc, H-3, H-4, H-5, H-6, H-6', 2H GluNH-C=O, piperazine ring-CH$_2$), 3.24 (s, $^+$N(CH$_3$)$_3$)) ppm; UV-vis (DMSO): λ$_{max}$: 420, 520, 547, 599, 651 nm.

TPC$_{CP0.1}$-CS-MP$_{0.90}$ (38).

The general procedure C was followed using 36 (240 mg, 0.38 mmol) and conc.HCl/MeOH to give 38 as a brown solid (85 mg, 52%). FT-IR (KBr): v 3349, 2927, 1644, 1580, 1461, 1440, 1374, 1285, 1070, 1043, 985, 945, 794719, 703 cm$^{-1}$; $^1$H NMR (DMSO-d$_6$: D$_2$O 98:2): δ=7.86-8.63 (m, β-pyrrole-H, phenyl-Ho & R—COTPC-phenyl-Ho,m), 7.67-7.76 (m, triphenyl-Hm,p), 4.50 (br s, H-1), 4.08-4.14 (m, chlorin β-pyrrole-CH$_2$), 2.92-3.55 (m, partially overlapped with HDO peak, H-2 GlcNAc, H-3, H-4, H-5, H-6, H-6', 2H GluNH-C=O, CH$_2$CONGlc) 2.27-2.63 (m, partially overlapped with DMSO-d6 peak, piperazine ring-CH$_2$, piperazine-N—CH$_3$) ppm; UV-vis (DMSO): λ$_{max}$: 421, 520, 547, 599, 651 nm.

TPP Analogues of Compounds 32, 33, 37 and 38

Unexpected results (Back-oxidation of TPC compounds to TPP compounds by TBAF/NMP) were observed when used following the general TBDMS deprotection procedure D for final compounds 32, 33, 37 and 38).

Example: TPP Analogue of Compound 32 (TP-P$_{NP0.1}$—CS-TMA$_{0.9}$)

The material 30 (600 mg, 0.86 mmol) was dissolved in N-Methyl-2-pyrrolidone (NMP) (5-10 mL) followed by addition of an excess amount of tetra-n-butylammonium-fluoride (TBAF). The reaction mixture was stirred for 24 h at 55° C. and cooled and acidified with dilute HCl, and stirred for 30 minutes before it was dialyzed against 8% NaCl (w/v) in deionised water for two days and against deionised water for 3 days. During this time the colour of the solution changed gradually from grey to red. The red coloured solution was then freeze-dried to yield a brown sponge-like material. The materials were again deprotected, ion exchanged, dialyzed and freeze-dried. However, surprisingly due to back-oxidation the compounds were converted back to their TPP analogues which was confirmed by UV-Vis (as characteristic peak at 650 diminished almost completely). (Data not shown)

Results

Table 3, below, shows the DS for the final carrier compounds. Table 4 shows the fluorescence quantum yields (ϕ$_F$) of the TPC modified chitosan carriers. FIG. 14 shows the 1H NMR spectrum of TPC—CO-Pip (28)—both isomers are shown. FIGS. 15-17 show equivalent spectra for compounds 21, 29 and 34, respectively.

FIG. 18 shows the NMR spectra of the final carrier compounds 37, 38, 32 and 33 in d$_6$-DMSO/D$_2$O.

TABLE 3

| Entry | Chitosan Derivatives | Compound | TPC-NH-Pip (eq. per sugar unit used) | TPC-CO-Pip (eq. per sugar unit used) | DS (linked TPP moieties per sugar unit) |
|---|---|---|---|---|---|
| 1. | TPC$_{NP0.1}$-CS-TMA$_{0.9}$ | 32 | 0.10 | — | 0.10* |
| 2. | TPC$_{NP0.1}$-CS-MP$_{0.9}$ | 33 | 0.10 | — | 0.10* |
| 3. | TPC$_{CP0.1}$-CS-TMA$_{0.9}$ | 37 | — | 0.11 | 0.13** |
| 4. | TPC$_{CP0.1}$-CS-MP$_{0.9}$ | 38 | — | 0.11 | 0.13** |

*DS determined by $^1$H NMR of intermediate 29
**DS determined by $^1$H NMR of intermediate 34

TABLE 4

| Entry | Chitosan Derivatives | Compound | λ$_{abs}$* (nm) | λ$_{em}$* (nm) | Quantum Yield (ϕ$_F$) |
|---|---|---|---|---|---|
| 1. | TPC(p-NH$_2$)$_1$ | 20 | 420 | 653 | 0.00246 |
| 2. | TPC-NH-Pip | 21 | 420 | 653 | 0.01355 |
| 3. | TPC$_{NP0.1}$-CS-TMA$_{0.9}$ | 32 | 420 | 653 | 0.01383 |
| 4. | TPC$_{NP0.1}$-CS-MP$_{0.9}$ | 33 | 420 | 653 | 0.01353 |
| 5. | TPC(p-CO$_2$H)$_1$ | 26 | 420 | 653 | 0.01331 |
| 6. | TPC-CO-Pip | 28 | 420 | 653 | 0.01366 |
| 7. | TPC$_{CP0.1}$-CS-TMA$_{0.9}$ | 37 | 420 | 653 | 0.01270 |
| 8. | TPC$_{CP0.1}$-CS-MP$_{0.9}$ | 38 | 420 | 653 | 0.01275 |

*All data collected in DMSO at room temperature
λ-wavelength

Example 3—In Vitro and In Vivo Studies

Materials

The HCT116/LUC human colon carcinoma cell line (permanently transfected with a gene encoding luciferase) was kindly provided by Dr. Mohammed Amarzguioui, siRNA-sense, Oslo, Norway. MTT (3-[4,5-Dimethylthiazol-2-yl]-2,5-diphenyltetrazolium bromide) was from Sigma-Aldrich (MO, USA; cat. no. M 2128), dissolved in PBS to a concentration of 5 mg/ml, sterile filtered and stored at 4° C.

The plasmid pEGFP-N1 was purchased from Clontech Laboratories Inc. (CA, USA; Cat. No. 6085-1), produced by ELIM Biopharmaceuticals, Inc. (CA, USA) (lot #1002) and delivered at a concentration of 2 mg/ml in sterile water. This stock solution was aliquoted and kept at −20° C. Poly-L-Lysine HBr (MW 15000-30000) was from Sigma-Aldrich (MO, USA; cat. no. P 7890). Poly-L-Lysine HBr was dissolved and diluted in distilled water, sterilized by filtration and stored at −20° C.

In Vitro Studies

Cell Cultivation.

HCT116/LUC were cultured in DMEM medium (Lonza, Veviers, Belgium) supplemented with 10% fetal calf serum (PAA Laboratories GmbH, Pasching, Austria) 100 U/ml penicillin and 100 µg/ml streptomycin (Sigma-Aldrich, Mo., USA) at 37° C. and 5% $CO_2$ in a humid environment.

Treatment of the Cells.

HCT116/LUC cells ($1.5 \times 10^5$ cells per well for the transfection measurements, $3.75 \times 10^5$ cells per well for the MTT assay) were seeded into 6-well (transfection) and 24-well (MTT) plates (Nunc, Roskilde, Denmark) and incubated for 24 h (5% $CO_2$, 37° C.). The photosensitizer $TPCS_{2a}$ or the chitosan conjugates (16A, 16B, 17A, 19A, 37, 38, 32 or 33) were then added to the cells and the cells were incubated for 18 h (5% $CO_2$, 37° C.). The cells were then washed three times with cell culture medium and incubated for 4 h (5% $CO_2$, 37° C.) in medium containing the plasmid complex. Then the cells were washed once. After addition of fresh medium the cells were illuminated with different light doses. After 48 h of incubation the expression of EGFP (Enhanced Green Fluorescent Protein) was analyzed by flow cytometry. Cell survival was measured by the MTT assay in parallel experiments. The cells were exposed to light from LumiSource® (PCI Biotech, Oslo, Norway). LumiSource® is delivered with a bank of 4 light tubes (4×18 W Osram L 18/67, Blue) emitting mainly blue light with a peak wavelength in the region of 420-435 nm.

Preparation of Plasmid/Poly-L-Lysine Complexes.

Plasmid/poly-L-lysine complexes with charge ratio 2.2 were formed by gentle mixing of plasmid DNA and poly-L-lysine solutions. 2.5 µl of DNA (stock solution 2 µg/µl) was diluted with 47.5 µl water, and 6.92 µl poly-L-lysine (1 µg/µl) was diluted with 43.08 µl water. After mixing, the solution was incubated at room temperature for 30 min, then diluted with culture medium to a final volume of 1 ml and added to the cells (1 ml per well).

Measurement of Transfection.

The cells were trypsinized in 100 µl trypsin (Trypsin-EDTA, Sigma-Aldrich, Mo., USA), resuspended in 500 µl cell culture medium and filtered through a 5 ml Polystyrene Round-Bottom Tube with Cell-Strainer Cap (BD Falcon) (50 µm mesh nylon filter) before analysis in a BD LSR flow cytometer (Becton Dickinson, Calif., USA). EGFP was measured through a 425-475 nm filter after excitation at 488 nm, and propidium iodide (Calbiochem Corporation, CA, USA) was measured through a 600-620 nm filter after excitation at 561 nm. Propidium iodide (1 µg/ml) was used to discriminate dead cells from viable cells, and pulse-processing was performed to discriminate cell doublets from single cells. 10000 events were collected for each sample, and the data was analyzed with BD FACSDiva Software (Becton Dickinson, Calif., USA).

Measurement of Cell Survival.

Cell survival was measured by a method based on reduction of a water-soluble tetrazolium salt (MTT) to a purple, insoluble formazan product by mitochondrial dehydrogenases present in living, metabolically active cells. 0.5 ml medium containing 0.125 mg MTT was added to the cells, followed by a 2 h incubation at 37° C., 5% $CO_2$. The resulting formazan crystals were dissolved by adding 500 µl DMSO (Sigma-Aldrich, Mo., USA) per well. The plates were read by a PowerWave XS2 Microplate Spectrophotometer (BioTek Instruments, VT, USA). Cell survival was calculated as percent of controls (parallels with no light).

In Vivo Studies

Animals.

Hsd:Athymic nude-Foxn1$^{nu}$ female mice were bred at the animal department at the Norwegian Radium Hospital. The mice were kept under specific pathogen-free conditions. Water and food was given ad libitum. All procedures involving mice were carried out in agreement with the protocols approved by the animal care committee at the Norwegian Radium Hospital, under the National Ethical Committee's guidelines on animal welfare.

The mice were 22-25 g (5-8 weeks old) when included in the experiment. The HCT116/LUC cells were cultured at 37° C. and 5% $CO_2$ in a humid environment before transplantation. $1.5 \times 10^6$ cells were injected subcutaneously on the right hip of each mouse. The tumor size was measured two or three times per week by measuring two perpendicular diameters. Tumour volume was calculated using the following formula:

$$V = (W^2 \times L)/2$$

where W is the width and L the length diameters of the tumour measured.

Treatment.

The chitosans were diluted to 1.25 mg/ml TPC in PBS (compound 37) and 3% Tween 80 (compounds 38 and 33). 88-100 µl was injected intravenously in the tail vein (final dose 5 m/kg) when the tumours had reached a volume of 60-100 mm$^3$. The $TPCS_{2a}$ was diluted to 1.25 mg/ml in 3% Tween 80 and 88-100 µl was injected intravenously in the tail vein (final dose 5 m/kg) when the tumours had reached a volume of 60-100 mm$^3$. 96 h after the injection of photosensitizer the tumours were illuminated with a 652 nm diode laser (Ceramoptec GmbH, Bonn, Germany) at an irradiance of 90 mW/cm$^2$ and a 15 J/cm$^2$ light dose. For animals receiving PCI+Bleomycin treatment, 1500 IU Bleomycin (European units) in 100 µl was injected intraperitoneally. The tumours were illuminated 30 min after BLM injection with a 652 nm diode laser (Ceramoptec GmbH, Bonn, Germany) at an irradiance of 90 mW/cm$^2$. The animals were covered with aluminum foil except the tumour area where a hole in the foil was made with a diameter 2 mm larger than the tumour area.

In Vivo Imaging System.

The bioluminescence was measured with an IVIS Lumina 100 Series from Caliper Life Sciences, MA, USA. The animals were anesthetized (Zoletil) and injected with 200 µl D-Luciferin (Caliper Life Sciences) (20 mg/ml in PBS) intraperitoneally. The images were taken 10 min after D-Luciferin injection. The bioluminescence was measured approximately once a week from day 11 after PS injection. The animals were sacrificed when the tumour reached a volume>1000 mm$^3$ or when the animal was showing signs of pain or abnormal behaviour.

The data was analyzed with Living Image 4.2 Software (Caliper Life Sciences).

The biological effect of the TPP-chitosan conjugates 16A and 16B was tested in experiments where the conjugates were used as photosensitising agents in photochemical internalisation to enhance gene delivery. The experimental details are described under Materials and Methods. As can be seen in FIGS. 19((*a*) and (*b*)) the conjugates 16A and 16B were excellent photosensitisers for PCI in that a substantial enhancement of transfection could be observed already at low light doses. The effect was enhanced relative to that obtained with the photosensitiser TPCS$_{2a}$ which has been specially designed for the use in PCI, and which is under clinical development for cancer treatment (Berg et al. 2011, supra). Thus, with TPCS$_{2a}$ similar levels of transfection was not achieved even when employing higher light doses (FIG. 19(e)).

Similar experiments were performed with the TPP-chitosans 17A and 19A (FIGS. 19(c) and (d)). It can be seen that these conjugates are even more potent than 16A and 16B. Thus, as compared to TPCS$_{2a}$ they were at least 10 times more active, in that even when used in a 10 times lower concentration these conjugates gave a substantially greater enhancement of transfection than what was observed with TPCS$_{2a}$. This was quite surprising in that one would have expected that the proximity of the sensitiser molecules in the chitosan conjugates would lead to quenching of the photosensitising effect making the conjugates less effective than free sensitiser molecules that would not be subject to such quenching effects. Thus, it seems that the photosensitiser-chitosan conjugates interact with the endocytic membranes in some unknown way that makes them especially well suited for use in PCI and related methods.

As can be seen from FIG. 20 similar results were obtained with TPC-chitosan conjugates (compounds 37, 38, 32 and 33), which as compared to the TPP-conjugates have the advantage that they can be activated also by illumination with red light, allowing for better tissue penetration when used in vivo. This is an important feature in the treatment of larger lesions in vivo (e.g. larger tumours), but is a disadvantages in cases where one only wants to have a shallow photochemical effect, e.g. in vaccination approaches where the desired effect will be in the upper layers of the skin.

As can be seen from FIG. 21 similar results were also obtained with compound 54, showing that also PEG-containing conjugates are effective in inducing a PCI effect.

TPC-conjugates have also been explored in in vivo experiments, investigating whether the conjugates are active in PDT- and PCI-based therapeutic approaches. FIG. 22 shows pictures of illuminated tumour-bearing mice treated with the conjugates 38 and 33 either alone or together with the cytotoxic anti-cancer agent bleomycin (for details see Materials and Methods). Untreated animals and animals injected with TPCS$_{2a}$+bleomycin were used as controls. The cancer cells used were permanently transfected to express luciferase so that the extent of the tumours could be monitored by imaging of bioluminescence after injection of luciferin. As shown in FIG. 22 the untreated control and the TPCS$_{2a}$+bleomycin animals (8 and 7, respectively) exhibited strong fluorescence 11 and 15 days after the injection of photosensitiser (7 and 11 days after illumination), indicating the presence of large amounts of living cancer cells in the tumour. In these animals the tumours had grown so large that the animals had to be sacrificed for humane reasons after day 15. In contrast, for the animals treated with the chitosan conjugates there was only weak fluorescence in only one of the animals (animal 3) at day 11, showing that both the pure photochemical treatment (PCI alone, analogous to a PDT treatment) and the PCI+bleomycin combination treatment had strongly reduced the amount of cancer cells in the tumour. It can be seen that in the animals treated with PCI alone (animals 3 and 5) the fluorescence increased through day 15 to day 20, showing that the PCI photochemical treatment alone was not sufficient to kill all the tumour cells. In contrast the animals treated with PCI+bleomycin (animals 4 and 6) showed essentially no fluorescence even at day 20 showing that this combination was significantly more effective than PCI alone, indicating that the chitosan conjugates induced a strong photochemical internalisation effect; and much stronger than what was induced by the photosensitiser TPCS$_{2a}$ that is under clinical development for cancer treatment.

In FIG. 23 curves of the tumour growth in the treated animals are shown (including also the compound 37 chitosan conjugate) corroborating the imaging results shown in FIG. 22, and showing that in the animals treated with compound 38+bleomycin or 33+bleomycin the tumours seem to be completely eradicated. These results again indicate that the chitosan conjugates are much more effective agents for PCI than TPCS$_{2a}$ (which in combination with bleomycin had no effect on tumour growth in this experiment). Furthermore it can be seen that the addition of bleomycin to the treatment schedule significantly improved the therapeutic effect for all three chitosan conjugates tested (as compared to the photochemical treatment alone), indicating the induction of a strong photochemical internalisation effect by these conjugates. This enhanced efficacy is highly surprising since the main reason for designing photosensitiser-polymer conjugates is to obtain better selectivity of the treatment because of the so-called EPR effect. One should however expect that this potentially enhanced selectivity would be followed by a lower efficacy because of the large molecular weight of the conjugates leading to much slower diffusion through the tissues than for small molecule photosensitisers, and thus to a lower concentration of sensitiser in the tumour cells, and difficulties in delivering the sensitiser to all cells in a tumour. With the chitosan conjugates described in the present invention this was clearly not the case.

Example 4

General materials and methods were as for Example 1, where appropriate.
See Scheme 7 in FIG. 24
Synthesis of triethyleneglycol monomethyl ether tosylate (40) (also named 2-(2-(2-methoxyethoxy)ethoxy)ethyl 4-methylbenzenesulfonate)

Triethylene glycol monomethyl ether 39 (4.87 mL, 30.43 mmol) was dissolved in THF (25 mL). An aqueous solution (25 mL) of potassium hydroxide (3.7 g, 65.95 mmol) was added and the resulting mixture was cooled down to 0° C. Then, p-toluenesulfonyl chloride (6.86 g, 48.77 mmol) dissolved in THF (50 mL) was added dropwise via dropping funnel over a period of 30 minutes. The reaction mixture was stirred for 2 h more at 0° C. and then allowed to stir at rt overnight. The reaction mixture was concentrated in vacuo to remove THF before it was diluted with EtOAc (40 mL) and water (30 mL) and extracted with EtOAc (2×75 mL). The combined organic phase was dried over Na$_2$SO$_4$, filtered and concentrated in vacuo to afford compound 40 (7.13 g) as a gray-cloudy oily material.

FT-IR: 2878, 1598, 1453, 1356, 1177, 1097 cm$^{-1}$; $^1$H NMR (400 MHz, CDCl$_3$): δ=7.80 (d, J=8 Hz, 2H), 7.34 (d, J=8 Hz, 2H), 4.16 (t, 2H, C$\underline{H}_2$OTs), 3.67-3.70 (m, 2H, —C$\underline{H}_2$—CH$_2$OTs), 3.58-3.62 (m, 6H, TEG OC$\underline{H}_2$'s), 3.37 (s, 3H, OC$\underline{H}_3$), 2.44 (s, 3H, Ar—C$\underline{H}_3$) ppm; $^{13}$C NMR (400 MHz, CDCl$_3$): δ=144.91, 133.19, 129.94, 128.12, 72.05, 70.90, 70.71, 69.36, 68.83, 59.17, 21.78 ppm.
Synthesis of (triethyleneglycol monoethyl ether tosylate) (42) (also named 2-(2-(2-ethoxyethoxy)ethoxy)ethyl 4-methylbenzenesulfonate)

Triethylene glycol monoethyl ether 41 (4.9 mL, 28.1 mmol) was dissolved in THF (30 mL). An aqueous solution (25 mL) of potassium hydroxide (3.7 g, 65.95 mmol) was added. The reaction mixture was then cooled down to 0° C. Then, p-toluenesulfonyl chloride (6.86 g, 48.77 mmol) dissolved in THF (50 mL) was added dropwise via dropping funnel over a period of 30 minutes. The reaction mixture was stirred for 2 h more at 0° C. and then allowed to stir at rt overnight. The reaction mixture was concentrated in vacuo to remove THF before it was diluted with EtOAc (40 mL) and water (30 mL) and extracted with EtOAc (2×75 mL). The combined organic phase was dried over $Na_2SO_4$, filtered and concentrated in vacuo to afford compound 42 (6.83 g) as a gray-cloudy oily material.

FT-IR: 2870, 2975, 1598, 1453, 1358, 1177, 1110 $cm^{-1}$; $^1H$ NMR (400 MHz, $CDCl_3$): δ=7.77 (d, J=8 Hz, 2H), 7.31 (d, J=8 Hz, 2H), 4.13 (t, 2H, C$\underline{H_2}$OTs), 3.64-3.67 (m, 2H, —C$\underline{H_2}$CH$_2$OTs), 3.52-3.59 (m, 8H, TEG OC$\underline{H_2}$'s), 3.49 (q, J=8 Hz, 2H, —OC$\underline{H_2}$CH$_3$), 2.42 (s, 3H, Ar—C$\underline{H_3}$), 1.17 (t, J=8 Hz, 3H, —OCH$_2$C$\underline{H_3}$) ppm.

Synthesis of Methoxy Polyethyleneglycol Tosylate (44)

Polyethylene glycol monomethyl ether 43 (5 g, 14.29 mmol, average MW: 350 Da) was dissolved in THF (50 mL). An aqueous solution (25 mL) of potassium hydroxide (1.76 g, 31.44 mmol) was added. The reaction mixture was then cooled down to 0° C. Then, p-toluenesulfonyl chloride (3.27 g, 17.14 mmol) dissolved in THF (50 mL) was added dropwise via a dropping funnel over a period of 30 minutes. The reaction mixture was stirred for 2 h more at 0° C. and then allowed to stir at rt overnight. The reaction mixture was concentrated in vacuo to remove THF before it was diluted with EtOAc (40 mL) and water (30 mL) and extracted with EtOAc (2×75 mL). The combined organic phase was dried over $Na_2SO_4$, filtered and concentrated in vacuo to afford compound 44 (5.91 g) as a gray-cloudy oily material.

$^1H$ NMR (400 MHz, $CDCl_3$): δ=7.74 (d, J=8 Hz, 2H), 7.29 (d, J=8 Hz, 2H), 4.11 (br t, 2H, C$\underline{H_2}$OTs), 3.49-3.65 (m, 28H, —C$\underline{H_2}$—CH$_2$OTs & PEG OC$\underline{H_2}$'s), 3.32 (s, 3H, OCH$_3$), 2.39 (s, 3H, Ar—C$\underline{H_3}$) ppm.

Synthesis of triethyleneglycol monoethylether piperazine (46) (also named 1-(2-(2-(2-ethoxyethoxy)ethoxy)ethyl)piperazine (46) (TEG-Pip)

Piperazine (10.4 g, ~120 mmol) was dissolved in acetonitrile (150 mL) under nitrogen atmosphere. Compound 42 (5 g, 15.04 mmol) dissolved in acetonitrile (30 mL) was added dropwise. The resulting mixture was stirred at rt for 12 h before it was concentrated in vacuo to remove acetonitrile. The crude product was purified by flash silica gel column chromatography using MeOH: $CH_2Cl_2$ (8:92) as eluent to afford pure compound 46 (1.52 g, 41%) as a colourless liquid.

$^1H$ NMR (400 MHz, $CDCl_3$): δ=3.54-3.64 (m, 10H, TEG OC$\underline{H_2}$'s), 3.50 (q, J=8 Hz, 2H, —OC$\underline{H_2}$CH$_3$), 3.43 (s, 1H, NH), 2.88 (t, 4H, Piperazine ring-C$\underline{H_2}$), 2.55 (t, 2H, OCH2-C$\underline{H_2}$-Piperazine), 2.46 (br m, 4H, Piperazine ring-C$\underline{H_2}$), 1.18 (t, J=8 Hz, 3H, —OCH$_2$C$\underline{H_3}$) ppm; $^{13}C$ NMR: 70.76, 70.70, 70.47, 69.92, 68.86, 66.73, 58.47, 54.89, 50.55, 45.99, 15.25 ppm; MS (ESI) calcd. for $C_{12}H_{27}N_2O_3$ ($[M+H]^+$) 247.2016, found 247.2014.

Synthesis of 2-(2-(2-methoxyethoxy)ethoxy)acetaldehyde (45)

Oxalyl chloride (5 mL, 58.24 mmol) was dissolved in $CH_2Cl_2$ (75 mL) under nitrogen atmosphere. The resulting mixture was cooled down to −78° C. using dry-ice/acetone mixture before careful drop-wise addition of DMSO (5 mL) diluted in $CH_2Cl_2$ (15 mL). After complete addition, the reaction mixture was stirred for 10 minutes more before dropwise addition of triethyleneglycol monomethyl ether 39 (5 mL, 31 mmol) diluted in $CH_2Cl_2$ (30 mL). The reaction mixture was stirred for 15 minutes after complete addition. Then, $Et_3N$ (20 mL, 143 mmol) diluted in $CH_2Cl_2$ (20 mL) was added drop-wise over a period of 20 minutes and stirred for 30 minutes more to −78° C. before allowing it to reach rt. The white "milky" coloured reaction mixture was then washed with water (2×45 mL) and with brine (40 mL). The organic phase was dried over $Na_2SO_4$, filtered and concentrated in vacuo. The resulting crude product was purified by silica gel column chromatography using MeOH/EtOAc (0:100-10:90) as eluent to afford aldehyde 45 (2.40 g). 1H NMR analysis revealed that compound 47 was contaminated with some inseparable impurity.

FT-IR: 3436, 2879, 1734, 1454, 1353, 1108, 1028 $cm^{-1}$; $^1H$ NMR (400 MHz, $CDCl_3$) δ ppm: 9.73 (s, 1H, CHO), 4.16 (s, 2H), 3.54-3.76 (m, 10H), 3.38 (s, 3H) ppm. (Product is contaminated with starting material. Product is approximately 50%.)

Synthesis of 2-(2-(2-ethoxyethoxy)ethoxy)acetaldehyde (47)

Same procedure as used for above compound; except the starting material used was triethyleneglycol monoethyl ether (41) instead of triethyleneglygol monomethyl ether (39). Compound 47 (Yield: 2.34 g, ~42%) contaminated with some inseparable impurity.

$^1H$ NMR (400 MHz, $CDCl_3$) δ ppm: 9.67 (s, 1H, CHO), 4.10 (s, 2H), 3.52-3.69 (m, 10H), 3.45 (q, 2H), 1.15 (t, 3H) ppm. (Product is contaminated with starting material. Product is approximately 42%).

TEGylation of Chitosan by Direct N-Modifications of 3,6-di-O-TBDMS-Chitosan See scheme 8 in FIG. 25

Synthesis of N-(2-(2-(2-ethoxyethoxy)ethoxy)ethylamino chitosan $TEG_{0.41}$-CS (49a)

DiTBDMS-chitosan 8 (300 mg, 0.77 mmol) was dissolved in NMP (5 mL) and heated to 50° C. in a reaction vial. $Cs_2CO_3$ (1 g, 3.07 mmol) and a catalytic amount of potassium iodide was added. Then, the reaction vial was sealed and the reaction mixture stirred for 2 h before addition of compound 42 (767 mg, 2.31 mmol) via a syringe. The reaction mixture was stirred for 48 h before it was cooled down and poured into ice-water and the precipitate obtained was filtered off, and dried using a vacuum oven. The crude product 48a (270 mg) was obtained as a yellow powder and used as it was for the next deprotection step as described below.

For deprotection of hydroxyl groups (removal of the silyl groups), the crude compound 48a was suspended in MeOH (15 mL). Concentrated HCl (2 mL) was added slowly at rt and the resulting mixture was stirred for 12 h before it was concentrated in vacuo. The crude product obtained was again suspended in MeOH (15 mL) and conc. HCl (2 mL) was added and stirred for 12 h before it was diluted and ion exchanged with aqueous NaCl (5%, 35 mL) solution and then dialyzed against deionized water for 3 days. After completion of dialysis, the water soluble material was freeze-dried to afford 49a (125 mg) as a white sticky material.

FT-IR: 3418, 2874, 1712, 1631, 1536, 1378, 1077 $cm^{-1}$; $^1H$ NMR (400 MHz, $D_2O$) δ=4.68 and 4.27 (s, 1H, chitosan H-1 & H-1'), 3.14-3.97 (br m, 10H, chitosan H-2 to H-6, TEG (~41% DS) OC$\underline{H_2}$'s and O—C$\underline{H_2}$CH$_3$), 2.96-3.14 (br m, 1H, H-2 & H-2'), 1.21 (t, 1.24H (~41% DS) TEG O—CH$_2$C$\underline{H_3}$) ppm.

Synthesis of N-(2-(2-(2-ethoxyethoxy)ethoxy)ethylamino chitosan $TEG_{0.27}$-CS (51b) (27% DS)

Compound 49b was prepared by using same procedure as described above, except 1.5 equivalents of the triethylene glycol tosylate (42) reagent was used instead of 3 equivalents. Compound 49b (27 mg) was obtained as a white sticky material.

FT-IR: 3417, 2876, 1602, 1382, 1259, 1078, 599 cm$^{-1}$; $^1$H NMR (400 MHz, D$_2$O: DCI, 95:5) δ=5.13 and 4.95 (s, 1H, chitosan H-1 & H-1'), 3.24-3.99 (br m, 12H, chitosan H-2 to H-6, H-2', TEG (27% DS) OC$\underline{H}_2$'s and O—$\underline{CH_2}$CH$_3$), 1.21 (t, 0.89H, TEG O—CH$_2$C$\underline{H}_3$) ppm.

Synthesis of N-acetylbromo-3,6-O-diTBDMS-Chitosan (9)

DiTBDMS-chitosan 8 (3 g, 7.70 mmol) (previously synthesized by Ingólfur Magnusson) was dissolved in CH$_2$Cl$_2$ (30 mL) under nitrogen atmosphere. The resulting mixture was cooled down to −20° C. before addition of triethylamine (5.30 ml, 38 mmol) using a syringe. After 10 minutes of stirring, bromo acetylbromide (2.65 ml, 30.51 mmol) diluted in CH$_2$Cl$_2$ (2.5 mL) was added dropwise using a syringe. The reaction mixture was then stirred for 1 hour at −20° C. before it was diluted with CH$_2$Cl$_2$ (70 mL) and immediately concentrated in vacuo. Then, the thick brown material was triturated and washed with acetonitrile (3×35 mL), dried before it was re-dissolved in CH$_2$Cl$_2$ (40 mL) and placed in a separatory funnel where it was washed with water (2×25 mL) and with brine (35 mL). The organic phase was dried over Na$_2$SO$_4$, filtered and concentrated in vacuo to afford bromoacyl intermediate 9 (2.57 g) as a brown solid material.

FT-IR (KBr): v 3404 (br, NH), 2956-2858 (s, C—H TBDMS), 1682 (vs, C=O amide I), 1530 (vs, C=O amide II), 1473, 1391, 1362, 1311, 1259, 1101, 1005, 837, 777 (Si—C), 669 cm$^{-1}$; $^1$H NMR (CDCl$_3$) δ ppm: 4.40 (br s, 1H, H-1), 3.26-4.02 (m, 8H, H-2 GlcN, H-3, H-4, H-5, H-6, H-6' and GluNH—C=OCH$_2$Br), 0.90 and 0.88 (br s, 18H, (CH$_3$)$_3$C—Si), 0.13 and 0.07 (br s, 12H, CH$_3$.Si) ppm.

PEGylation of Chitosan by Nucleophilic Substitution on N-Acetyl Bromo-3,6-diTBDMS-Chitosan N-(acetyl piperazine-TEG)-Chitosan (51)

(i) Acetyl bromochitosan 9 (200 mg, 0.397 mmol) was dissolved in CH$_2$Cl$_2$ (25 mL) under a nitrogen atmosphere. Compound 46 (204 mg, 0.828 mmol) diluted in CH$_2$Cl$_2$ (10 mL) was added dropwise at rt. The resulting mixture was stirred for 10 minutes before addition of triethylamine (115 μL, 0.828 mmol). Stirring was continued at rt for 24 h and the total consumption of starting material 46 was confirmed by checking TLC in MeOH: CH$_2$Cl$_2$ (1:9). Then the reaction mixture was placed in a separatory funnel and the organic phase was washed with water (2×35 mL) and brine (35 mL), dried over Na$_2$SO$_4$, filtered and concentrated in vacuo to afford compound 50 (214 mg) as a crude liquid which was used as it is for the next deprotection step.

(ii) For deprotection of hydroxyl groups (removal of the silyl groups), the crude compound 50 was suspended in MeOH (15 mL). Concentrated HCl (2 mL) was added slowly at rt and the resulting mixture was stirred for 12 h before it was concentrated in vacuo. The crude product obtained was again suspended in MeOH (15 mL) and conc. HCl (2 mL) was added and stirred for 12 h before it was diluted and ion exchanged with aqueous NaCl (5%, 35 mL) solution and then dialyzed against deionized water for 3 days. After completion of dialysis, the water soluble material was dried in vacuo to afford 51 (112 mg) as a yellowish clear sticky material.

$^1$H NMR (400 MHz, D$_2$O) δ=4.63 (s, 1H, chitosan H-1), 2.74-3.76 (m, 30H, chitosan H-2 to H-6, GlcNHCO C$\underline{H}_2$-Pip-TEG, TEG OC$\underline{H}_2$'s & O—$\underline{CH_2}$CH$_3$, piperazine ring-CH$_2$'s), 1.21 (t, 3H, TEG O—CH$_2$C$\underline{H}_3$) ppm; DS=100%.

Synthesis of N-acetyl-piperazine tetraphenylporphyrin (TPP-NH-Pip) (5)

This was performed as described above in Example 1 and Scheme 1.

Synthesis of TPP—NH—CO—CH$_2$-TBDMS-chitosan (55)

See Scheme 9 in FIG. 26.

DiTBDMS-chitosan (100 mg, mmol) was dissolved in NMP (10 mL) at 55° C. Cesium carbonate (500 mg, 1.54 mmol) was added and the reaction mixture was stirred for 15 minutes before addition of compound 4 (72.2 mg, 0.096 mmol). A catalytic amount of potassium iodide was added and stirring continued for 24 h before a catalytic amount of DMAP was added and stirred for 24 h before being cooled down and poured into water. The precipitate was filtered off, dried in a vacuum oven to afford compound 55 as a crude solid. However, a red colour of the water solution was observed indicating that some of the compound was wasted in water. That might be because of NMP; thus dialysis at this stage might be useful.

$^1$H NMR (400 MHz, D$_2$O) δ ppm: 8.84-8.86 (br m, β-pyrrole H), 8.68 (s, TPPNHCO), 8.21-8.22 (m, tetraphenyl-Ho), 7.99 (d, J=8.0 Hz, RNHTPP-phenyl-Hm), 7.72-7.79 (m, triphenyl-Hm,p), 2.72-4.80 (m, chitosan H-2-H6, TPPNHCOC$\underline{H}_2$),0.89-0.90(brs, (CH$_3$)$_3$C—Si), 0.05-0.07 (br s, 12H, CH$_3$—Si). −2.78 (s, α-pyrrole NH); ((DS of TPP-NHCOCH$_2$=~5%)

Synthesis of TPPp$_{0.1}$-BrA$_{0.9}$-DiTBDMS-CS (52)

Compound 9 (800 mg, 1.587 mmol) was dissolved in CH$_2$Cl$_2$ (40 mL) under a nitrogen atmosphere at room temperature. TPP-NH-Pip 5 (120 mg, 0.158 mmol) was added followed by addition of triethylamine (30 μl, 0.216 mmol). The reaction mixture was stirred for 24 h at rt. Complete consumption of starting material 5 was confirmed by TLC (MeOH: CH$_2$Cl$_2$, 1:9). The reaction mixture was diluted with CH$_2$Cl$_2$ (75 mL) and washed with water (2×35 mL) and brine (25 mL), dried over Na$_2$SO$_4$, filtered and concentrated in vacuo to afford 52 (yield: 716 mg) as a purple solid.

$^1$H NMR (CDCl$_3$) δ ppm: 9.31 (s, TPPN$\underline{H}$CO), 8.84-8.86 (m, β-pyrrole H), 8.20-8.23 (m, tetraphenyl-Ho), 7.97 (d, J=8.0 Hz, RNHTPP-phenyl-Hm), 7.74-7.79 (m, triphenyl-Hm,p), 4.43 (br s, H-1), 3.50-4.14 (m, chitosan H-2 GlcN, H-3, H-4, H-5, H-6, H-6' and H-2 GluNHCO, TPPNHCO C$\underline{H}_2$-Pip, —C$\underline{H}_2$CONGlc and Piperazine ring-CH$_2$'s), 2.81-2.86 (m, piperazine ring-CH$_2$'s), 0.91, 0.87 (br s, (C$\underline{H_3}$)$_3$C—Si), 0.07, 0.14 (br s, CH$_3$.Si), −2.77 (br s, α-pyrrole NH) ppm; (DS of TPP—NH-Pip=~10%).

TEGylation and Deprotection of TPP-Conjugated DiTBDMS-CS

Synthesis of TEGylated N-(TPP—NH—CO—CH$_2$)-chitosan (57)

(i) Crude compound 55 (350 mg, 0.833 mmol) was dissolved in NMP (10 mL) at 50° C. in a reaction vial. Cs$_2$CO$_3$ (1.09 g, 3.33 mmol) was added and the reaction mixture stirred for 30 minutes before addition of compound 42 (1.108 g, 4.16 mmol) and a catalytic amount of potassium iodide. Stirring was continued for 12 h before the reaction mixture was cooled down, diluted with water (30 mL) and dialyzed against deionized water for 3 days before being freeze-dried to afford compound 56 which was used as it was for the next deprotection step.

(ii) The crude compound 56 was suspended in MeOH (15 mL). Concentrated HCl (2 mL) was added slowly at rt and the resulting mixture was stirred for 12 h before it was concentrated in vacuo. The crude product obtained was again suspended in MeOH (15 mL) and conc. HCl (2 mL) was added and stirred for 12 h before it was diluted and ion-exchanged with aqueous NaCl (5%, 35 mL) solution and then dialyzed against deionized water for 3 days. After completion of dialysis, the partly water soluble material was dried in vacuo to afford 57 (115 mg) as a brown solid.

Synthesis of TEGylated TPP—NH-Pip-chitosan TPPp$_{0.1}$-CS-TEG$_{0.9}$ (54)

(i) Compound 52 (400 mg, 0.799 mmol) was dissolved in CH$_2$Cl$_2$ (35 mL) under a nitrogen atmosphere. Compound 46 (394 mg, 1.56 mmol) was added followed by addition of Et$_3$N (222 μl, 1.56 mmol) and the reaction mixture was stirred for 24 h at rt. Then, TLC was checked and Et$_3$N (222 μl, 1.56 mmol) added in order to complete consumption of starting material 46 and stirring was continued for 12 h more. Then, the reaction mixture was concentrated in vacuo to afford 53 (417 mg) as a crude material which was used as it was for next the deprotection step.

(ii) The crude compound 53 was suspended in MeOH (15 mL). Conc. HCl (2 mL) was added slowly at rt and the resulting mixture was stirred for 12 h before it was concentrated in vacuo. The crude product obtained was again suspended in MeOH (15 mL) and conc. HCl (2 mL) was added and stirred for 12 h before it was diluted and ion-exchanged with aqueous NaCl (5%, 35 mL) solution and then dialyzed against deionized water for 3 days. After completion of dialysis, the water soluble material was freeze-dried to afford final compound 54 (252 mg) as a purple-red-brown solid.

FT-IR: 3431, 2869, 1665, 1529, 1442, 1308, 1109, 1070, 1029, 800, 701, 559 cm$^{-1}$; $^1$H NMR (DMSO-d6: D$_2$O 96:4) δ ppm: 8.83 (br m, β-pyrrole H), 8.15-8.22 (m, tetraphenyl-Ho), 8.11 (d, J=8.0 Hz, RNHTPP-phenyl-Hm), 7.80-7.88 (m, triphenyl-Hm,p), 4.55 (br s, H-1), 2.54-3.65 (br m, partially overlapped with HDO peak, chitosan H-2 GlcN, H-3, H-4, H-5, H-6, H-6' and H-2 GluNHCO, TPPNHCO C$\underline{H_2}$-pip, C$\underline{H_2}$CONGlc, piperazine ring-C$\underline{H_2}$'s TEG OC$\underline{H_2}$'s and TEG OC$\underline{H_2}$CH$_3$), 1.09 (t, TEG OCH$_2$C$\underline{H_3}$) ppm.; (DS of TPP—NH-Pip=~10% and DS of TEG=~90%)

Structural data was confirmed by NMR, FT-IR and Mass analysis (data not shown). A representative NMR spectrum for compound 54 is shown in FIG. 27.

Example 5

In Vitro T Cell Activation Assay

For testing the effect of chitosan-conjugates 32 and 38 on MHC class I-restricted antigen-presentation and CD8+ T cell activation, murine primary macrophages were incubated with conjugates 32 and 38 and the ovalbumin OVA 257-264 peptide antigen in an antigen-specific T cell setting with an ovalbumin-specific (OVA 257-264) CD8+ T cell clone. IL-2 production from activated CD8+ T cells was analyzed by an ELISA.

Bone-marrow derived macrophages (BMDMs) were used as antigen-presenting cells (APCs) in an antigen-specific T cell setting with ovalbumin-specific T cell hybridomas. BMDMs were generated by cultivating mouse bone-marrow cells for at least 5 days in medium supplemented with 20% L-292 cell line supernatant.

30,000 APCs per well were incubated overnight in 96-well plates with or without chitosan-conjugates 32 and 38 at a concentration of conjugates giving a TPC concentration of 0.05 μg/ml. The next day the APCs were incubated with 2 μg/ml of antigenic peptide (OVA 257-264, from Anaspec) for 4 h (all stimulations in triplicate).

Cells were washed and exposed to different doses of blue light (0; 30, 60, 90, 180 sec) before 100,000 ovalbumin-specific T cells per well were added and co-cultured with the APCs overnight. The CD8+ T cell clone RF33.70 (MHC I-restricted recognition of OVA 257-264) was used.

After overnight co-culture of CD8+ T cells and APCs, supernatants from the cell culture were harvested. The supernatants were analyzed for interleukin (IL)-2 production from activated T cells by use of a standard mouse IL-2 ELISA (IL-2 ELISA Duoset, RnD Systems, analysis of duplicates from each well of T cell culture, 25 μl of undiluted supernatant was analyzed in each ELISA well).

The results (FIG. 28) showed that with both conjugates IL-2 production by the CD8+ antigen-specific T cells was significantly increased in the illuminated cells (e.g. a doubling for the compound 32 conjugate, FIG. 28A). In illuminated control cells incubated with the conjugates without the antigen no such increase was seen (data not shown). This demonstrates that the observed effect was antigen-dependent, and was not due to some unspecific effect of the photochemical treatment, demonstrating enhanced presentation of the antigenic peptide on the surface of the APCs as the cause of the observed increase in IL-2 production.

The invention claimed is:

1. A compound comprising a conjugate of a photosensitiser and chitosan, wherein said compound is a compound of Formula (I):

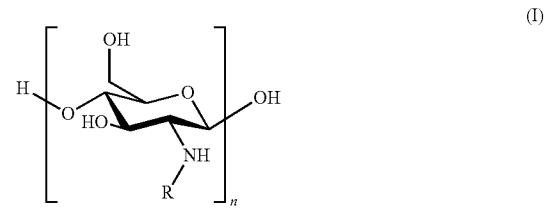

wherein
n is an integer greater than or equal to 3,
R appears n times in said compound and in 0.5%-99.5% of said total Rn groups, each R is a group A selected from:
H,

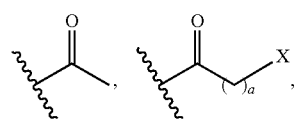

wherein a is 1, 2, 3, 4 or 5; and X is Br, Cl or OH;

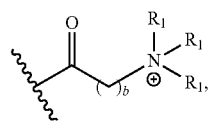

wherein each R$_1$, which may be the same or different, is selected from H, CH$_3$ and —(CH$_2$)$_c$—CH$_3$; b is 1, 2, 3, 4 or 5; and c is 0, 1, 2, 3, 4 or 5;

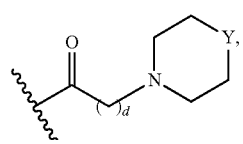

wherein Y is O; S; SO₂, —NCH₃; or —N(CH₂)ₑCH₃; d=1, 2, 3, 4 or 5; and e=1, 2, 3, 4 or 5;

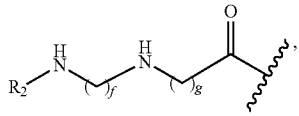

wherein R₂ is —(CH₂)ₕ—CH₃ or —CO—(CH₂)ₕ—CH₃; f is 1, 2, 3, 4 or 5; g is 1, 2, 3, 4 or 5; and h is 0, 1, 2, 3, 4 or 5;

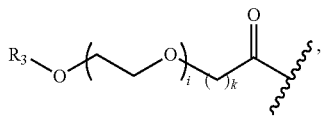

wherein R₃ is —(CH₂)ⱼ—CH₃, i is an integer from 1 to 200; j is 0, 1, 2, 3, 4 or 5; and k is 1, 2, 3, 4 or 5;

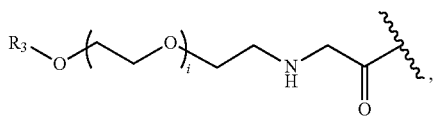

wherein R₃ is —(CH₂)ⱼ—CH₃, i is an integer from 1 to 200; and j is 0, 1, 2, 3, 4 or 5;

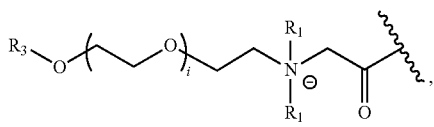

wherein R₃ is —(CH₂)ⱼ—CH₃, i is an integer from 1 to 200; j is 0, 1, 2, 3, 4 or 5; and each R₁, which may be the same or different, is selected from H, CH₃ and —(CH₂)ₑ—CH₃; and c is 0, 1, 2, 3, 4 or 5;

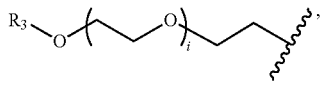

wherein R₃=—(CH₂)ⱼ—CH₃, i is an integer from 1 to 200; and j is 0, 1, 2, 3, 4 or 5;

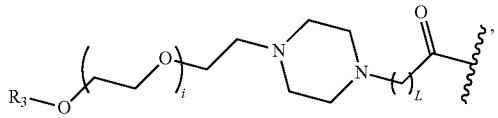

wherein R₃=—(CH₂)ⱼ—CH₃, i is an integer from 1 to 200; L is 1, 2, 3, 4, 5, 6, 7, 8, 9 or 10; and j is 0, 1, 2, 3, 4 or 5;

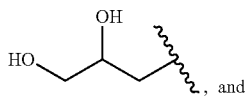

, and

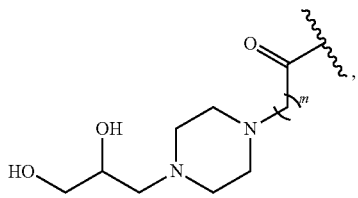

wherein m is 1, 2, 3, 4 or 5;

wherein each R group may be the same or different; and in 0.5%-99.5% of said total Rn groups, each R is a group B selected from:

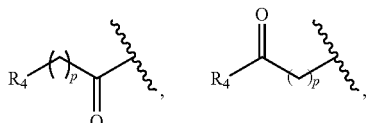

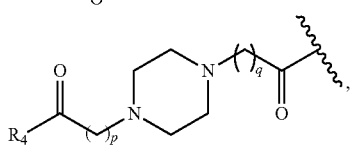

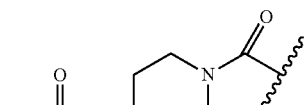

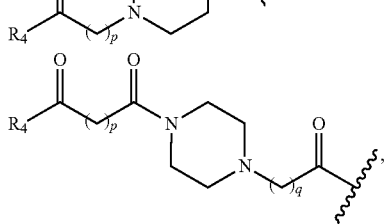

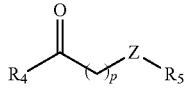

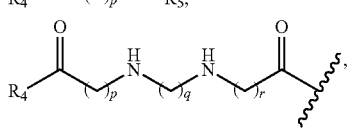

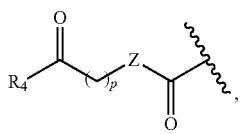

, and 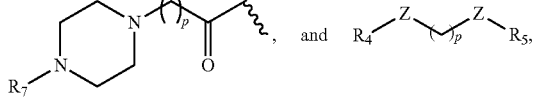

wherein p is 0, 1, 2, 3, 4 or 5; q is 1, 2, 3, 4 or 5; and r is 1, 2, 3, 4 or 5;

$R_4$ is a group selected from:

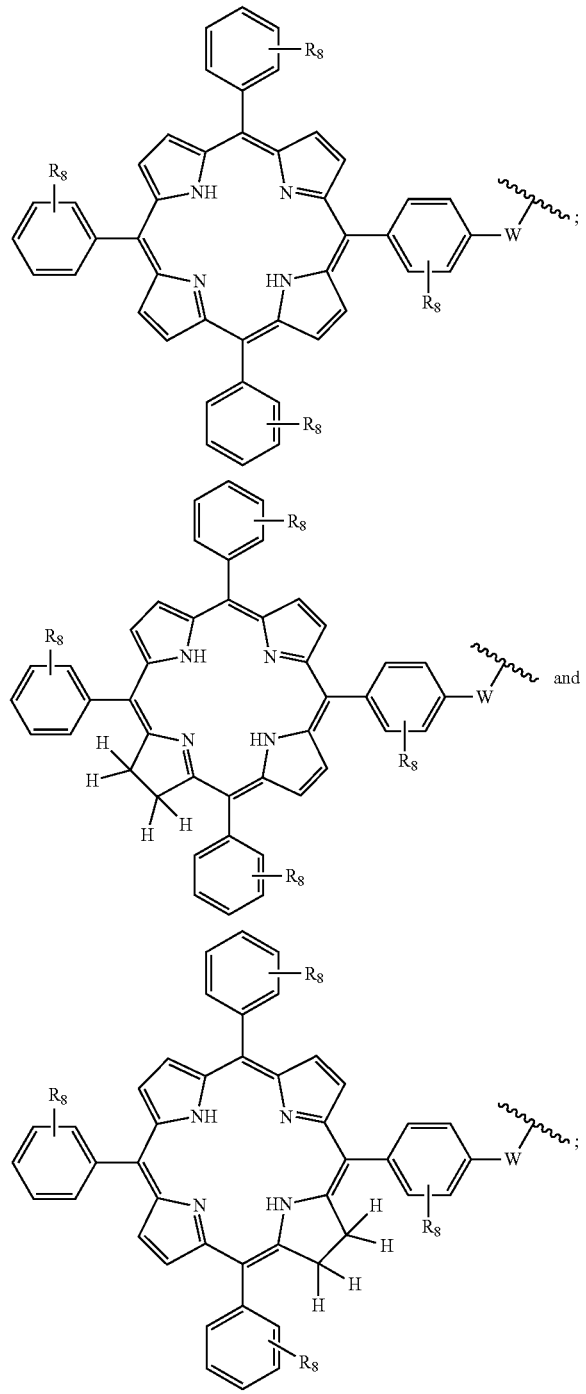

W is a group selected from O, S, NH or N(CH₃);
$R_5$ is a group selected from: —(CH₂)$_s$—CO—; —(CH₂)$_s$—Z—(CH₂)$_t$CO— and —(CH₂)$_s$—Z—(CH₂)$_t$Z—CO—; wherein s is 0, 1, 2, 3, 4 or 5; t is 0, 1, 2, 3, 4 or 5;
Z is NH, O, S, or SO₂,
$R_6$ is a group selected from —CN and CH₃, $R_7$ is a group selected from:

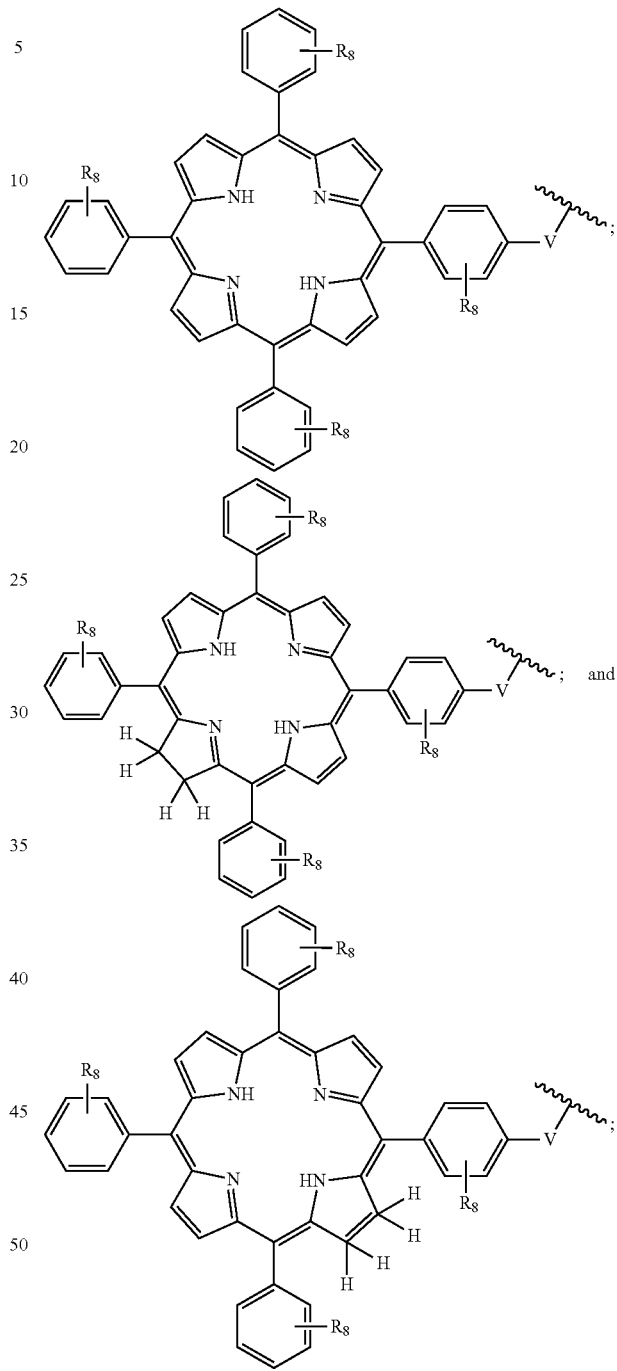

V is a group selected from CO, SO₂, PO, PO₂H or CH₂; and
$R_8$ is a group (substituted in the o, m or p position), which may be the same or different, selected from H, —OH, —OCH₃, —CH₃, —COCH₃, C(CH₃)₄, —NH₂, —NHCH₃, —N(CH₃)₂ and —NCOCH₃,
wherein each R group may be the same or different.

2. A compound as claimed in claim 1 wherein n is an integer from 10 to 100.

3. A compound as claimed in claim 1 wherein $R_4$ is selected from

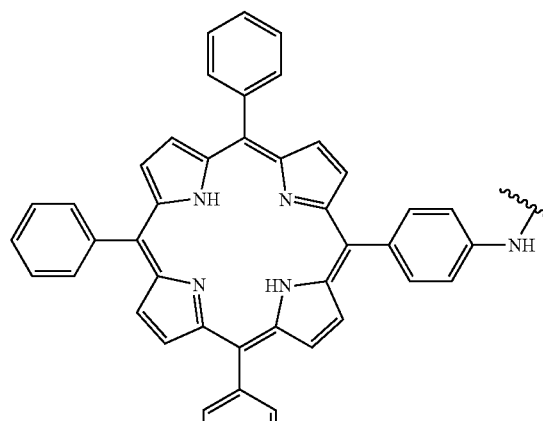
TPPa
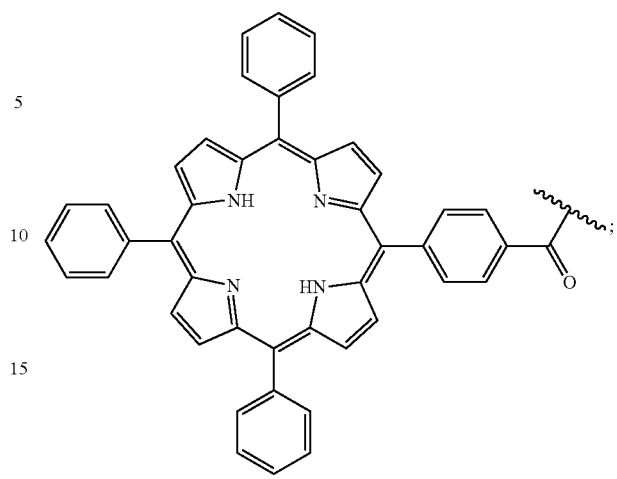
TPPc
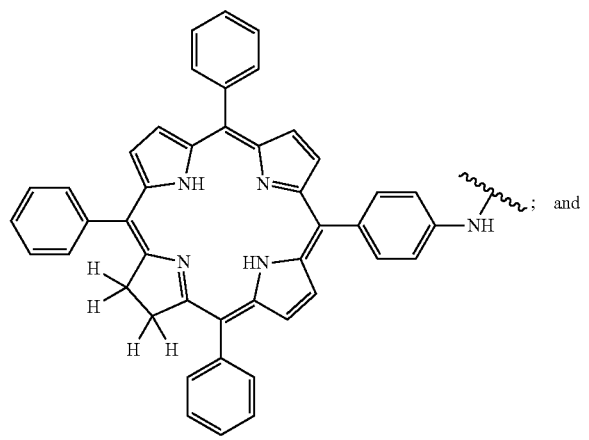
TPCa$_1$
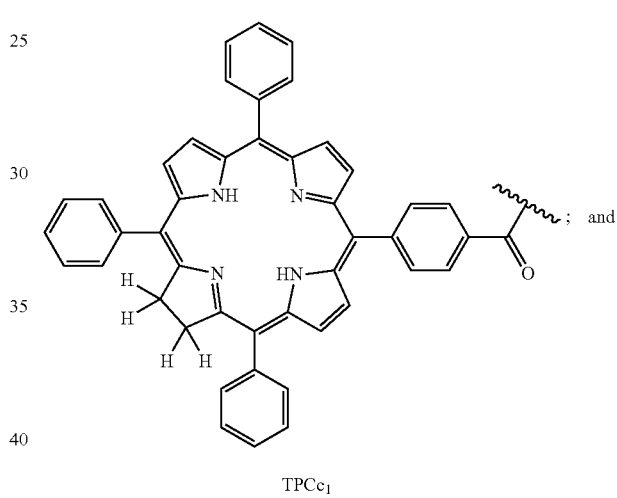
TPCc$_1$
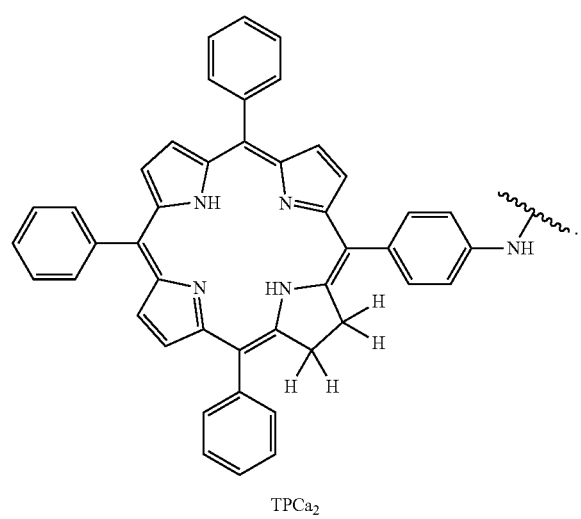
TPCa$_2$
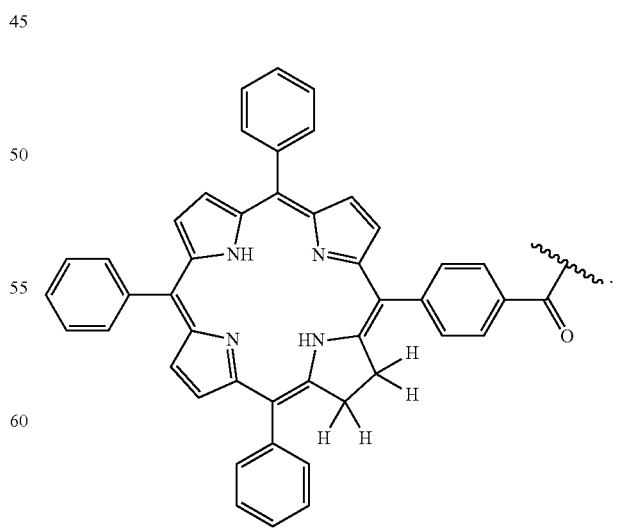
TPCc$_2$
4. A compound as claimed in claim 1 wherein R$_7$ is selected from

5. A compound as claimed in claim 3 wherein $R_4$ is $TPCa_1$ or $TPCa_2$.

6. A compound as claimed in claim 1 wherein group A provides 70 to 95% of the total Rn groups and group B provides 5 to 30% of the total Rn groups.

7. A compound as claimed in claim 1 wherein each group A R group is selected from:

wherein each $R_1$ is $CH_3$ and b is 1;

wherein Y is —$NCH_3$ and d is 1;

wherein preferably j is 0 or 1; i is 3 or 6 and k is 1;

wherein j is 1 and i is 2;

wherein j is 0 or 1 and i is 2, 4 or 5 and L is 1;

, and wherein m is 1, and each R group may be the same or different.

8. A compound as claimed in claim 1 wherein each group B R group is selected from:

wherein p is 1;

wherein p is 1 and q is 1;

wherein p is 1; and wherein p is 1, and each R group may be the same or different.

9. A compound as claimed in claim 1 wherein said compound is selected from the following compounds 87 88
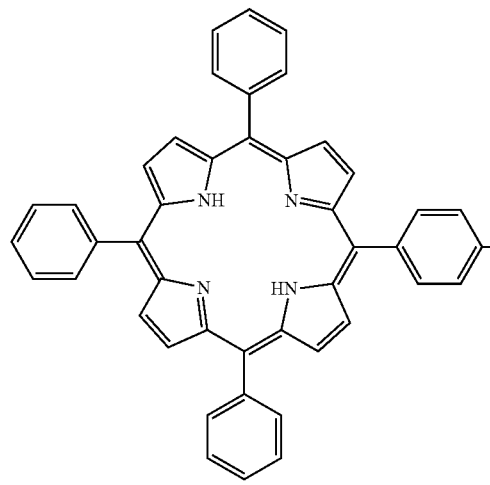
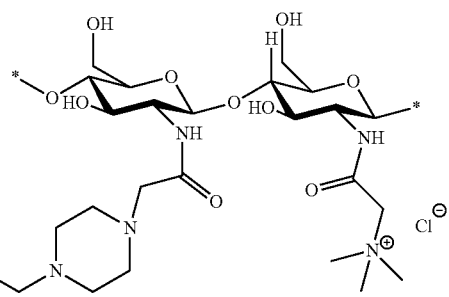
10%, 90% Compound 16,
25%, 75% Compound 17,
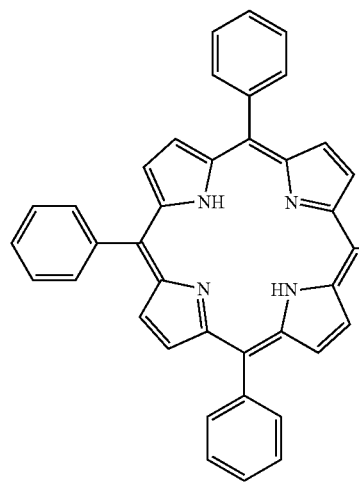
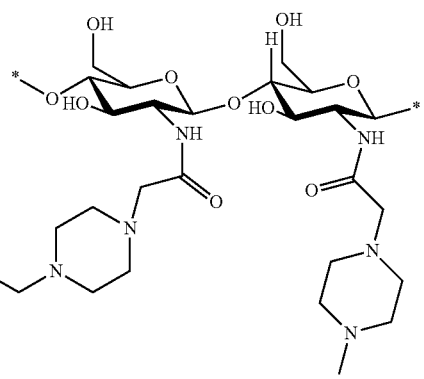
10%, 90% Compound 18,
25%, 75% Compound 19,
Compound 37                                      Compound 38
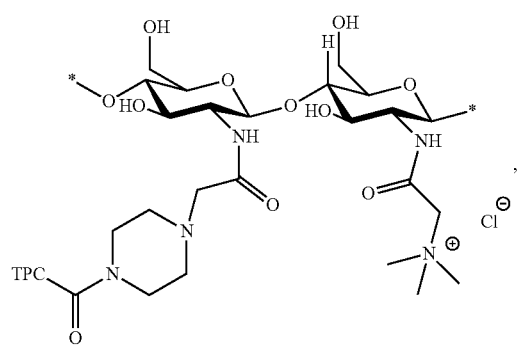
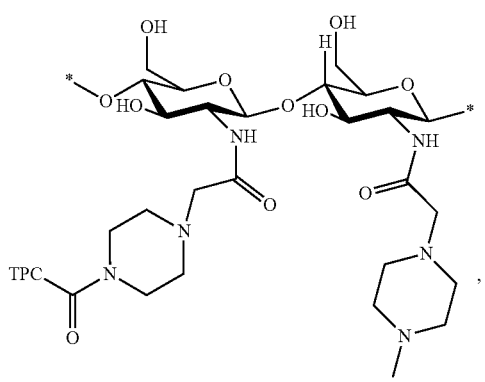
10%    90%                                       10%    90%

-continued
Compound 32
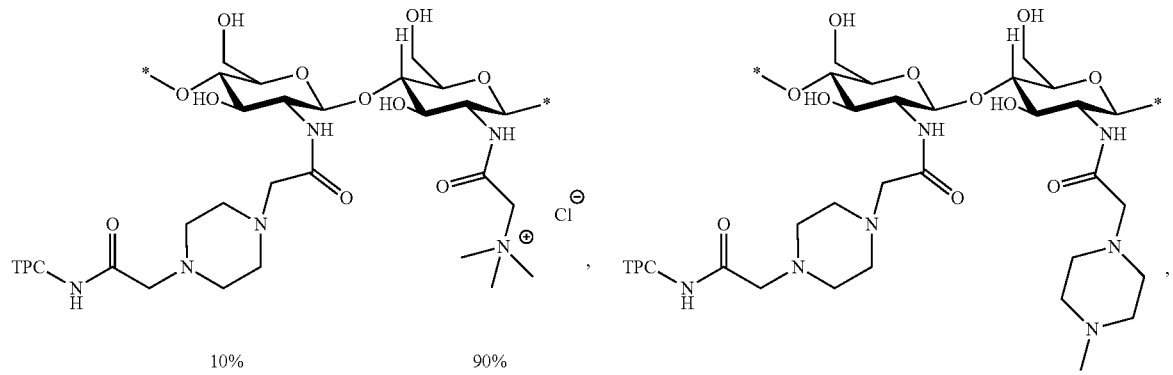
10%  90%
Compound 33
10%  90%
Compound 54
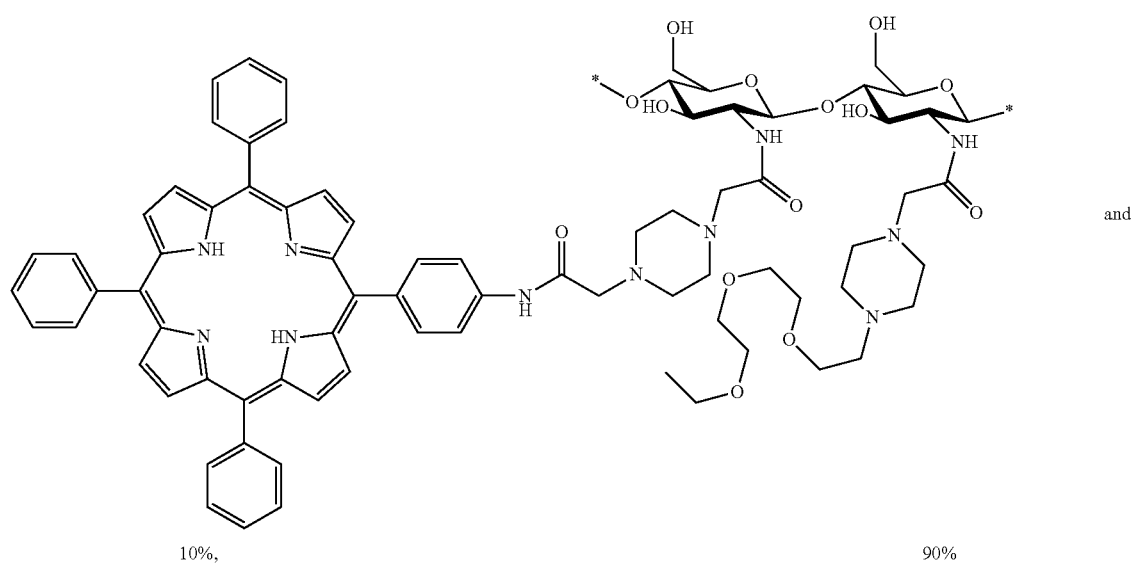
10%,  90%
and
Compound 57
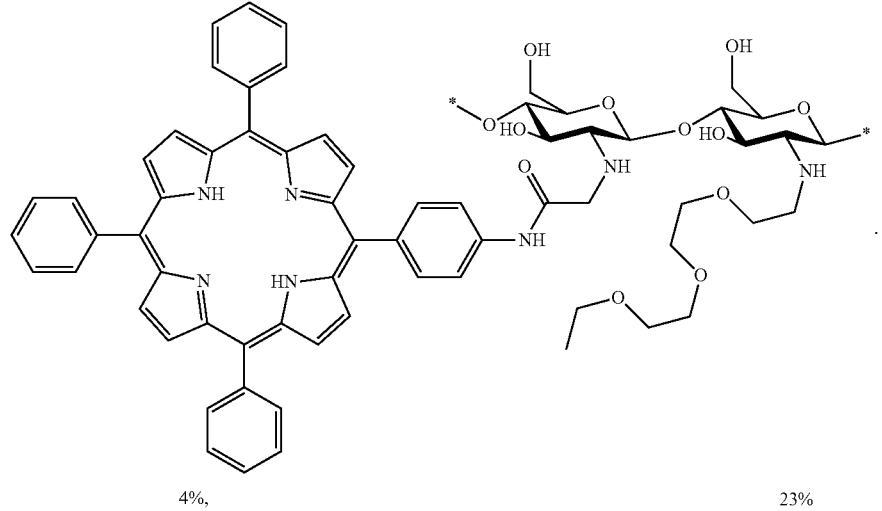
4%,  23%

10. A compound as claimed in claim 4 wherein $R_7$ is $TPCc_1$ or $TPCc_2$.

11. The compound of claim 1, wherein when group A is

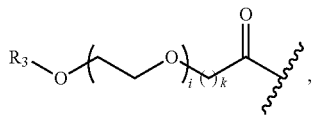

i is an integer from 1-10.

12. The compound of claim 1, wherein when group A is

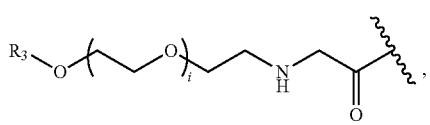

i is an integer from 1-10.

13. The compound of claim 1, wherein when group A is

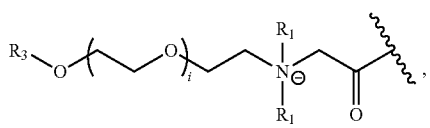

i is an integer from 1-10.

14. The compound of claim 1, wherein when group A is

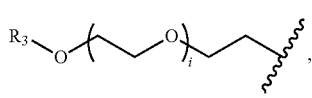

i is an integer from 1-10.

15. The compound of claim 1, wherein when group A is

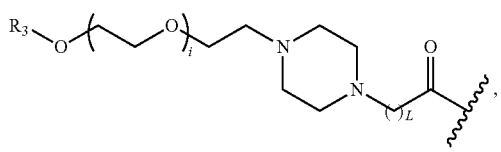

i is an integer from 1-10.

16. A pharmaceutical composition comprising a compound as defined in claim 1 and one or more pharmaceutically acceptable diluents, carriers or excipients, and optionally a molecule to be internalized.

17. A kit comprising a compound as defined in claim 1, or a composition comprising said compound, and a molecule to be internalized.

18. A method for introducing a molecule into the cytosol of a cell, comprising contacting said cell with the molecule to be introduced and a compound as defined in claim 1, and irradiating the cell with light of a wavelength effective to activate the photosensitising agent of the compound thereby releasing the molecule into the cytosol.

19. A method of achieving death of a cell comprising contacting said cell with a compound as defined in claim 1, and irradiating the cell with light of a wavelength effective to activate the photosensitising agent of the compound to generate reactive oxygen species which cause death of said cell.

20. A method of expressing an antigenic molecule or a part thereof on the surface of a cell, comprising contacting said cell with said antigenic molecule and a compound as defined in claim 1, and irradiating the cell with light of a wavelength effective to activate the photosensitising agent of the compound, wherein said antigenic molecule is released into the cytosol of the cell and the antigenic molecule or a part thereof of sufficient size to stimulate an immune response is presented on the cell's surface.

21. A cell or a population of cells obtainable by a method as defined in claim 18.

22. A method of achieving death of a cell in a patient comprising introducing a compound as defined in claim 1, or a composition comprising said compound, and a cytotoxic molecule to be internalized, into one or more cells in vivo by a method comprising contacting said cells with said compound and said cytotoxic molecule to be introduced, and irradiating the cells with light of a wavelength effective to activate the photosensitising agent of the compound thereby generating reactive oxygen species which cause death of the cell and/or releasing said cytotoxic molecule to be introduced into the cytosol.

23. A cell or a population of cells obtainable by a method as defined in claim 20.

24. A method of stimulating an immune response in a subject, comprising introducing a compound as defined in claim 1, or a composition comprising said compound, and an antigenic molecule to be internalized, into one or more cells in vitro, in vivo or ex vivo by a method comprising contacting said cells with said compound and said antigenic molecule to be introduced, and irradiating the cells with light of a wavelength effective to activate the photosensitising agent of the compound thereby releasing said antigenic molecule to be introduced into the cytosol and presenting the antigenic molecule or a part thereof of sufficient size to stimulate an immune response, and where necessary administering said cells to said patient, whereby an immune response is stimulated in said subject.

25. A method as claimed in claim 18 wherein said method is carried out in vivo.

26. A method as claimed in claim 19 wherein said method is carried out in vivo.

27. A method as claimed in claim 20 wherein said method is carried out in vivo.

28. The method of claim 22, wherein the cell is a cancer cell.

* * * * *